(12) United States Patent
Ohashi et al.

(10) Patent No.: US 8,283,104 B2
(45) Date of Patent: Oct. 9, 2012

(54) SULFONATE AND ITS DERIVATIVE, PHOTOSENSITIVE ACID GENERATOR, AND RESIST COMPOSITION AND PATTERNING PROCESS USING THE SAME

(75) Inventors: Masaki Ohashi, Jyoetsu (JP); Takeshi Kinsho, Jyoetsu (JP); Youichi Ohsawa, Jyoetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 250 days.

(21) Appl. No.: 12/706,450

(22) Filed: Feb. 16, 2010

(65) Prior Publication Data
US 2010/0209827 A1 Aug. 19, 2010

(30) Foreign Application Priority Data
Feb. 19, 2009 (JP) ................ 2009-037048

(51) Int. Cl.
*G03F 7/004* (2006.01)
*C07C 309/00* (2006.01)
(52) U.S. Cl. ........ 430/270.1; 430/5; 430/326; 430/330; 430/910; 562/42; 562/100; 562/109; 562/113
(58) Field of Classification Search .......... 430/5, 270.1, 430/326, 330, 910; 560/150; 562/42, 100, 562/109, 113
See application file for complete search history.

(56) References Cited

U.S. PATENT DOCUMENTS

| | | | |
|---|---|---|---|
| 5,585,507 A | 12/1996 | Nakano et al. | |
| 5,650,483 A | 7/1997 | Malik et al. | |
| 5,705,702 A | 1/1998 | Osawa et al. | |
| 5,731,364 A | 3/1998 | Sinta et al. | |
| 5,945,250 A | 8/1999 | Aoai et al. | |
| 6,440,634 B1 | 8/2002 | Ohsawa et al. | |
| 6,723,483 B1 | 4/2004 | Oono et al. | |
| 7,262,321 B2 * | 8/2007 | Harada et al. ............... | 560/129 |
| 2001/0036591 A1 | 11/2001 | Schulz et al. | |
| 2003/0013039 A1 | 1/2003 | Kobayashi et al. | |
| 2004/0033440 A1 | 2/2004 | Maeda et al. | |
| 2004/0260031 A1 | 12/2004 | Takeda et al. | |
| 2006/0228648 A1 | 10/2006 | Ohsawa et al. | |
| 2007/0231738 A1 | 10/2007 | Kaneko et al. | |
| 2008/0026331 A1 | 1/2008 | Hasegawa et al. | |
| 2008/0102407 A1 | 5/2008 | Ohsawa et al. | |
| 2008/0118860 A1 | 5/2008 | Harada et al. | |

FOREIGN PATENT DOCUMENTS

| | | |
|---|---|---|
| CA | 2049772 | 2/1992 |
| JP | A-04-230645 | 8/1992 |
| JP | A-05-222257 | 8/1993 |
| JP | A-07-025846 | 1/1995 |
| JP | A-08-311018 | 11/1996 |
| JP | A-09-015848 | 1/1997 |
| JP | A-09-323970 | 12/1997 |
| JP | A-10-039500 | 2/1998 |
| JP | A-2000-336121 | 12/2000 |
| JP | A-2001-122850 | 5/2001 |
| JP | A-2001-181221 | 7/2001 |
| JP | A-2002-193887 | 7/2002 |
| JP | A-2002-193925 | 7/2002 |
| JP | A-2003-066612 | 3/2003 |
| JP | A-2004-115630 | 4/2004 |
| JP | A-2004-133393 | 4/2004 |
| JP | A-2005-008766 | 1/2005 |
| JP | B2-3613491 | 1/2005 |
| JP | A-2005-084365 | 3/2005 |
| JP | A-2007-145797 | 6/2007 |
| JP | A-2007-297590 | 11/2007 |
| JP | A-2008-031298 | 2/2008 |
| JP | A-2008-111103 | 5/2008 |
| JP | A-2008-133448 | 6/2008 |

OTHER PUBLICATIONS

DeVoc et al., "Photochemistry and Photophysics of 'Onium Salts," *Advanced Photochemistry*, vol. 17, John-Wiley & Sons, (1992), pp. 313-355.
Miller et al., "Deoxygenation of Sulfoxides Promoted by Electrophilic Silicon Reagents; Preparation of Aryl-Substituted Sulfonium Salts," *Journal of Organic Chemistry*, vol. 53 (1988), pp. 5571-5573.
Arimitsu et al., "Sensitivity Enhancement of Chemical-Amplification-Type Photoimaging Materials by Acetoacetic Acid Derivatives," *Journal of Photopolymer Science and Technology*, vol. 8, No. 1 (1995), pp. 43-46.
Arimitsu et al., "Effect of Phenolic Hydroxyl Residues on the Improvement of Acid-Proliferation-Type Photoimaging Materials," *Journal of Photopolymer Science and Technology*, vol. 9, No. 1 (1996), pp. 29-30.
Dammel et al., "193 nm Immersion Lithography—Taking the Plunge," *Journal of Photopolymer Science and Technology*, vol. 17, No. 4 (2004), pp. 587-602.
Lowe, "Synthesis of Sulphonium Salts," *The Chemistry of Sulfonium Group*, John-Wiley & Sons, (1981), pp. 267-312.

\* cited by examiner

*Primary Examiner* — John Chu
(74) *Attorney, Agent, or Firm* — Oliff & Berridge, PLC

(57) ABSTRACT

There is disclosed a sulfonate shown by the following general formula (2).

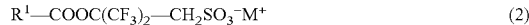

$$R^1-COOC(CF_3)_2-CH_2SO_3^-M^+ \quad (2)$$

(In the formula, $R^1$ represents a linear, a branched, or a cyclic monovalent hydrocarbon group having 1 to 50 carbon atoms optionally containing a hetero atom. $M^+$ represents a cation.) There can be provided: a novel sulfonate which is effective for a chemically amplified resist composition having a sufficiently high solubility (compatibility) in a resist solvent and a resin, a good storage stability, a PED stability, a further wider depth of focus, a good sensitivity, in particular a high resolution and a good pattern profile form; a photosensitive acid generator; a resist composition using this; a photomask blank, and a patterning process.

20 Claims, 12 Drawing Sheets

SULFONATE AND ITS DERIVATIVE, PHOTOSENSITIVE ACID GENERATOR, AND RESIST COMPOSITION AND PATTERNING PROCESS USING THE SAME

BACKGROUND OF THE INVENTION

1. Field of the Invention

The present invention relates to a novel sulfonate and its derivative advantageously usable as a photosensitive acid generator and the like in a resist composition, a photosensitive acid generator, a resist composition using the same, and a patterning process.

2. Description of the Related Art

As LSI progresses toward a higher integration and a further acceleration in speed, a finer pattern rule is being requested. In such a movement, a deep-ultraviolet lithography is drawing an attention as the promising next-generation fine processing technology.

In recent years, technologies utilizing a KrF excimer laser having a high brightness and an ArF excimer laser having a further shorter wavelength have been drawing an attention as the light sources of a far ultraviolet ray. In addition, an ArF immersion lithography, which can be designed to have 1.0 or more of the numerical aperture (NA) of a projection lens by inserting a liquid having a higher refractive index than that of an air, such as water, ethylene glycol, and glycerin between the projection lens and a wafer, thereby attaining a high resolution, is rapidly drawing a growing attention (see, for example, Journal of photopolymer Science and Technology Vol.17, No. 4, p 587 (2004)). A further fine processing technology is sought by shifting toward a shorter wavelength of the exposure light and by attaining a higher resolution in the resist composition.

From this view point, a chemically amplified resist composition catalyzed by an acid, which has been developed recently, has excellent properties in sensitivity, resolution, and dry-etching resistance, and thus is a promising resist composition, particularly for a deep-ultraviolet lithography. In this chemically amplified resist composition, there are a positive type in which an exposed area is removed with leaving an unexposed area unremoved and a negative type in which an unexposed area is removed with leaving an exposed area unremoved.

In a chemically amplified positive resist composition using an alkaline developer, a part or all of a resin and/or a compound whose alkaline-soluble phenol group or carboxylic acid group is protected by an acid-unstable protection group (an acid-labile group) is catalytically decomposed, by an acid generated by an exposure, to form a phenol or a carboxylic acid in the exposed area, thereby removing this exposed area by an alkaline developer. On the other hand, in a chemically amplified negative resist composition, a resin and/or a compound having an alkaline-soluble phenol or carboxylic acid is crosslinked, by an acid generated by an exposure, with a compound (acid-crosslinker) that can link (crosslink) the resin or the compound by the acid to insolubilize the exposed part in an alkaline developer, thereby removing the unexposed part by the alkaline developer.

In the chemically amplified positive resist composition, a base resin having the acid-labile group and a compound generating the acid by radiation irradiation (hereinafter referred to as an photosensitive acid generator for short) are dissolved in a solvent, and the resist solution thus prepared is applied on a substrate by various ways, heated if necessary and then the solvent is removed, to form a resist film. Subsequently, the formed resist film is exposed to a light source such as a far ultraviolet ray by radiation irradiation through a prescribed mask pattern. Further, as appropriate, a post exposure bake (PEB) is done after the exposure to carry out an acid-catalyzed reaction, and the development by an alkaline solution is done to remove the exposed area of the resist film to obtain a positive pattern profile. After the substrate is etched by various ways, the remaining resist film is removed by dissolving in a delaminating solution or by ashing to form a pattern profile on the substrate.

In the chemically amplified positive resist composition for the KrF excimer laser, a resin whose part or all of hydrogen atoms of the phenolic hydroxyl group of a phenolic resin such as polyhydroxy styrene is protected by an acid-unstable protection group is used, and a photosensitive acid generator such as an iodonium salt, a sulfonium salt, a bissulfonyl diazomethane, an N-sulfonyloxy dicarboxyimide compound, an O-arene sulfonyloxime compound has been used. In addition, as appropriate, a dissolution inhibitor and/or a dissolution facilitator having a molecular weight of 3,000 or less formed of a carboxylic acid and/or a phenolic derivative wherein a part of or all of the hydrogen atoms of a carboxylic acid and/or a phenolic hydroxy group is protected by the acid-labile group, a carboxylic acid compound to improve dissolution characteristics, a basic compound to improve a contrast, a surfactant to improve coating characteristics, and the like are added.

Here, a photosensitive acid generator generating 10-camphor sulfonic acid or 2,4,6-triisopropylbenzene sulfonic acid suppresses diffusion not only in a sulfonium salt and an iodonium salt but also in an O-arene sulfonyloxime compound, and thus it is extremely useful for a high resolution resist composition (Japanese Patent Laid-Open No. H05-222257, Japanese Patent Laid-Open No. H10-39500, Japanese Patent Laid-Open No. 2004-133393, and Japanese Patent Laid-Open No. H09-323970). These photosensitive acid generators have a bulky structure thereby suitably suppressing an acid diffusion, and it is assumed that because of this an excellent resist performance is realized.

However, as a further miniaturization of the pattern size is required, there appeared problems of a low resolution, a poor environmental stability, and the like even when these photosensitive acid generators are used. Under such a circumstance, as to the resolution problem, an improvement is being made by making an acid-labile group in the used resin further easily breakable by an acid, and by using a basic additive and selecting a process condition.

The problems in the environmental stability may be classified roughly into two kinds; the one is the problem that the acid generated by light-exposure is inactivated by a base in an air above the resist film and on the substrate underneath the resist film, which is the phenomenon appears often when a photosensitive acid generator generating a highly acidic acid is used. The other problem of the environmental stability is that a generated acid diffuses in the resist film when the time of the light-exposure and the post exposure baking (PEB) after the exposure is prolonged, thereby inactivating the acid in the case when the acid-labile group is not easily breakable or facilitating the acid decomposition reaction in the case when the acid-labile group is easily breakable, and these, in turn, cause change of a pattern profile often. For example, narrowing of the line width of the unexposed area occurs often in the case of a chemically amplified positive resist composition having an acid-labile group such as an acetal group.

In Japanese Patent No. 3613491, an anion-bound PAG polymer is disclosed in a combination with a monomer having an acid-unlabile group. In this case, the effect as PAG is reduced due to the monomer having an acid-unlabile group, and thus resolution and the like are not sufficient.

As discussed above, in order to have an even higher resolution, introduction of a more easily breakable acid-labile group into a resin and use of a relatively weak acid as the photosensitive acid generator are necessary. However, the acid-labile group designed to be more easily breakable has a problem in the storage stability. When an acid-labile group having a good storage stability and an appropriate breakability is introduced, the resolution is insufficient in a further miniaturized patterning by a photosensitive acid generator generating a weak acid such as the 10-camphor sulfonic acid or 2,4,6-triisopropylbenzene sulfonic acid. On the other hand, use of a photosensitive acid generator generating a highly acidic acid such as an α-fluoroalkane sulfonic acid causes an environmental problem. Accordingly, a photosensitive acid generator is required to generate an acid having an appropriate acid strength.

The foregoing is essential also as a mask patterning method especially in an electron beam lithography, which is drawing an attention as an ultra-miniaturization process technology with 0.1 μm or less dimension.

However, drawing by an electron beam takes more time as compared with the conventional one-time light exposure. Accordingly, an even higher sensitivity is required to increase a throughput. In addition, a temporal stability under vacuum during and after the drawing is required as one of its important performances. Furthermore, depending on the substrate, some of a covering layer (such as $SiO_2$, TiN, and $Si_3N_3$) on a silicon wafer, chromium oxide on a mask blanks, and the like, affect the resist form (footing profile) after development. Accordingly, in order to have the high resolution and maintain the form after etching, to keep a rectangular form of the resist pattern profile independent of a kind of the substrate is also one of its important performances.

SUMMARY OF THE INVENTION

A photosensitive acid generator of a resist composition is required to have a sufficiently high solubility (compatibility) in a resist solvent and a resin, a good preservation stability, in particular a good pattern profile form, a PED stability, a high resolution, a further wider depth of focus, and a good sensitivity, but conventional photosensitive acid generators do not satisfy these requirements.

Deterioration of the pattern profile form on a mask blanks becomes a serious problem especially in processing of the photomask blanks, because it is also a cause of a pattern collapse as the integrated circuit pattern progresses toward further miniaturization in recent years.

Namely, an object of the present invention is to provide; a novel sulfonate, effective for a chemically amplified resist composition, giving a chemically amplified resist composition that is especially excellent in resolution and pattern profile form with solving the various problems as mentioned above; a photosensitive acid generator; a resist composition using this; a photomask blank, and a patterning process.

The present invention was made to address the problems as mentioned above and provides a sulfonate represented by the following general formula (1):

  (1)

(In the formula, M⁺ represents a cation.)

The sulfonate represented by the general formula (1) is a novel sulfonate. The sulfonate such as the one shown by the general formula (1) can be used as an intermediate raw material for the synthesis of a sulfonate, useful as a photosensitive acid generator, represented by the general formula (2) which will be described later.

It is preferable that M⁺ of the sulfonate of the present invention represented by the general formula (1) is any of a lithium ion, a sodium ion, a potassium ion, an ammonium ion, an iodonium ion, and a sulfonium ion.

When any of a lithium salt, a sodium salt, a potassium salt, an ammonium salt, an iodonium salt, and a sulfonium salt is used in the sulfonate, its synthesis is simple and isolation of the sulfonate as the intermediate raw material represented by the general formula (1) is easy. Further, when the sulfonium salt or the iodonium salt is used, for example, a sulfonium salt of sulfonic acid represented by the general formula (3) or (4), or an iodonium salt of sulfonic acid represented by the general formula (5), which are useful as the photosensitive acid generators and will be described later, can be easily obtained by acylation. The sodium salt, the lithium salt, the potassium salt, and the ammonium salt can be used as a synthesis intermediate material for the sulfonium salt or the iodonium salt by cation-exchange.

The sulfonate can be manufactured by reacting 2,2-bistrifluoromethyloxirane with a sulfur compound in water.

As mentioned above, when 2,2-bistrifluoromethyloxirane is used as the starting raw material of the sulfonate represented by the general formula (2) which will be described later, and is reacted with a sulfur compound in water, the sulfonate represented by the general formula (1), which is an intermediate raw material, can be synthesized from cheap raw materials and in a simple procedure. In addition, because water is used as the solvent, it is extremely advantageous also from an environmental viewpoint.

The present invention provides a sulfonate represented by the following general formula (2) as the sulfonate that can be synthesized from the novel intermediate raw material.

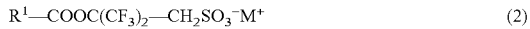  (2)

(In the formula, $R^1$ represents a linear, a branched, or a cyclic monovalent hydrocarbon group having 1 to 50 carbon atoms optionally containing a hetero atom. M⁺ represents a cation.)

The sulfonate of the present invention as represented by the general formula (2) has an ester moiety in the molecule, and thus a group from a less bulky acyl group to a bulky group and the like can be easily introduced, and thus the option of the molecular design can be made wider. In addition, because an electron-withdrawing trifluoromethyl group is present at the β-position of the sulfo group, its acid strength is weaker than an α-fluorosulfonic acid and stronger than an alkanesulfonic acid and an arene sulfonic acid. Accordingly, for example, if it is used as the acid generator, both an excellent resolution and a satisfactory environmental stability may be obtained in a KrF lithography and an electron beam lithography.

It is preferable that M⁺ of the sulfonate of the present invention represented by the general formula (2) is any of a lithium ion, a sodium ion, a potassium ion, an ammonium ion, an iodonium ion, and a sulfonium ion.

When M⁺ in the general formula (2) is any of a lithium ion, a sodium ion, a potassium ion, an ammonium ion, an iodonium ion, and a sulfonium ion, synthesis of the intermediate raw material is easy as mentioned before, and an intended sulfonate represented by the general formula (2) can be obtained easily by the same token. Especially the sulfonium salt and the iodonium salt can be used as the photosensitive acid generator, and the ammonium salt can be used as a thermal acid generator.

Specific examples of the sulfonate of the present invention represented by the general formula (2) include the sulfonium salt of sulfonic acid represented by the following general formula (3) or (4).

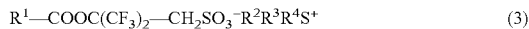

$$R^1-COOC(CF_3)_2-CH_2SO_3^- R^2R^3R^4S^+ \quad (3)$$

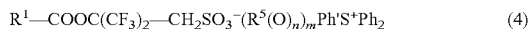

$$R^1-COOC(CF_3)_2-CH_2SO_3^- (R^5(O)_n)_m Ph'S^+Ph_2 \quad (4)$$

(In the formulae, $R^1$ represents the same as before. Each $R^2$, $R^3$, and $R^4$ independently represents a linear or a branched alkyl, alkenyl, or oxoalkyl group, substituted or unsubstituted, having 1 to 10 carbon atoms, a substituted or an unsubstituted aryl, aralkyl, or aryl oxoalkyl group having 6 to 18 carbon atoms, or any two or more of $R^2$, $R^3$, and $R^4$ may be bonded with each other to form a ring together with a sulfur atom in the formula. $R^5$ represents a linear, a branched, or a cyclic alkyl or alkenyl group, substituted or unsubstituted, having 1 to 20 carbon atoms, or a substituted or an unsubstituted aryl group having 6 to 14 carbon atoms. "m" represents an integer of 1 to 5, and "n" represents 0 or 1. Ph represents a phenyl group. Ph' represents a phenyl group whose "m" hydrogen atoms are substituted by a $R^5(O)_n$-group.)

The sulfonium salt of sulfonic acid shown by the general formula (3) or (4) responds to a high energy beam such as a UV ray, a far ultraviolet ray, an electron beam, an X-ray, an excimer laser, a γ-beam, and a synchrotron radiation beam, to generate a sulfonic acid represented by the general formula (6) which will be described later, and thus it can be used, for example, as a useful photosensitive acid generator.

In addition, specific examples of the sulfonate of the present invention represented by the general formula (2) include an iodonium salt of sulfonic acid represented by the following general formula (5).

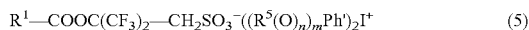

$$R^1-COOC(CF_3)_2-CH_2SO_3^- ((R^5(O)_n)_m Ph')_2I^+ \quad (5)$$

(In the formula, $R^1$ represents the same as before. $R^5$ represents a linear, a branched, or a cyclic alkyl or alkenyl group, substituted or unsubstituted, having 1 to 20 carbon atoms, or a substituted or an unsubstituted aryl group having 6 to 14 carbon atoms. "m" represents an integer of 1 to 5 and "n" represents 0 or 1. Ph' represents a phenyl group whose "m" hydrogen atoms are substituted by a $R^5(O)_n$-group.)

The iodonium salt of sulfonic acid shown by the general formula (5) also responds to a high energy beam such as a UV ray, a far ultraviolet ray, an electron beam, an X-ray, an excimer laser, a γ-beam, and a synchrotron radiation beam to generate the sulfonic acid represented by the general formula (6) which will be described later, and thus it can be used as a useful photosensitive acid generator.

The photosensitive acid generator of the present invention is used for the chemically amplified resist composition generating, by responding to a high energy beam, a sulfonic acid represented by the following general formula (6).

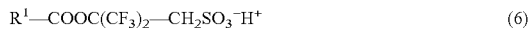

$$R^1-COOC(CF_3)_2-CH_2SO_3^- H^+ \quad (6)$$

(In the formula, $R^1$ represent a linear, a branched, or a cyclic monovalent hydrocarbon group having 1 to 50 carbon atoms, optionally containing a hetero atom.)

As described above, the photosensitive acid generator responding to a high energy beam to generate the sulfonic acid represented by the general formula (6) can be used for a chemically amplified resist composition having an especially excellent resolution and pattern profile form because it has an appropriate acid strength in steps of coating in the device production process, baking before exposure, exposure, baking after exposure, and development.

Further, it is preferable that the photosensitive acid generator include any one of the sulfonate represented by the general formulae (3) to (5).

As described above, the sulfonate of the present invention represented by the general formulae (3) to (5) can generate the sulfonic acid represented by the general formula (6). When this is used as the photosensitive acid generator, both an excellent resolution and a satisfactory environmental stability can be obtained especially in a KrF lithography, an electron beam lithography, and the like because it has an electron-withdrawing trifluoromethyl group at the β-position of the sulfo group thereby giving a weaker acid strength than the α-fluorosulfonic acid and a stronger acid strength than the alkanesulfonic acid and the arene sulfonic acid.

The resist composition of the present invention contains a base resin, an acid generator, and an organic solvent, wherein the acid generator generating the sulfonic acid represented by the general formula (6) can be used. Specifically, the photosensitive acid generator including any one of the sulfonates represented by the general formulae (3) to (5) can be used as the photosensitive acid generator.

The resist composition using these photosensitive acid generators generating the sulfonic acid represented by the general formula (6) by irradiation of a high energy beam has an excellent focus allowance, a small line-width change and form deterioration even in a prolonged PED, an excellent pattern profile form after development, and a high resolution suitable for fine processing.

In the present invention, the resist composition is preferably a chemically amplified positive resist composition containing the base resin that is insoluble or sparingly soluble in the developer but is made soluble in the developer by an acid.

As described above, a high resolution can be obtained with the positive type base resin of the resist composition. In addition, the chemically amplifying type using the acid generator of the present invention can give a high sensitivity and dry etching resistance, and thus a resist composition especially promising for a far-ultraviolet lithography can be obtained.

Here, it is preferable to further add a basic compound to the chemically amplified positive resist composition.

As described above, when the basic compound is added to the resist composition of the present invention, the diffusion rate in the resist film of the acid and the like generated from the acid generator can be suppressed. Further, the resist sensitivity can be controlled more easily, and in addition, because the diffusion rate of the acid in the resist film can be suppressed, the resolution can be improved, the sensitivity change after exposure can be suppressed, the dependence on the substrate and the environment can be reduced, and the exposure margin, the pattern profile, and the like can be improved further.

The present invention provides a patterning process including at least a step of coating the resist composition onto a substrate; a step of pattern-exposing by using a high energy beam via a photomask after a heat-treatment; and, after the heat-treatment as appropriate, a step of developing by using a developer.

As described above, the resist composition of the present invention can be used in the patterning process. Though needless to mention, other various steps such as etching, resist removing, and washing can also be performed.

Further, the present invention provides a photomask blank, wherein the resist composition is formed on a chrome compound film.

As described above, in manufacturing a photomask, when the resist composition of the present invention is used for processing of the photomask blank having the chrome material on its outermost surface, the resist pattern is not easily affected by the substrate dependency, and thus the patterning process of the present invention can be advantageously applied. Accordingly, a photomask blank to manufacture a highly reliable photomask can be obtained because a high resolution and a temporal stability can be obtained.

As explained above, according to the present invention, the sulfonate represented by the general formula (2) can be synthesized from the sulfonate represented by the general formula (1) as the intermediate raw material. Because this sulfonate represented by the general formula (2) has an ester moiety in its molecule, an acyl group from a less bulky group to a bulky group, such as a benzoyl group, a naphthoyl group, and an anthrayl group can be introduced easily, and thus the option of the molecular design as the photosensitive acid generator can be made wider. Using the sulfonate such as those represented by the general formula (2), specifically the sulfonate represented by the general formulae (3) to (5), as a photosensitive acid generator, generates the sulfonic acid represented by the general formula (6), which has an appropriate acid strength in steps of coating in the device production process, baking before exposure, exposure, baking after exposure, and development, and thus these can be used for a chemically amplified resist composition having an especially excellent resolution and pattern profile form. In addition, it has an appropriate acid strength in the resist composition especially for the exposure to a KrF excimer laser and an electron beam. Furthermore, the chemically amplified resist composition using the photosensitive acid generator that generates the sulfonic acid represented by the general formula (6) by irradiation of a high energy beam has an excellent focus allowance, a small line-width change and form deterioration even in a prolonged PED, an excellent pattern profile form after development, and a high resolution suitable for fine processing. In addition, the photosensitive acid generator of the present invention has an electron-withdrawing trifluoromethyl group at the β-position of the sulfo group, and because of this, its acid strength is weaker than an α-fluorosulfonic acid and stronger than an alkanesulfonic acid and an arene sulfonic acid. Accordingly, the photosensitive acid generator of the present invention can give both an excellent resolution and a satisfactory environmental stability in a KrF lithography and an electron beam lithography.

DETAILED DESCRIPTION OF THE PREFERRED EMBODIMENTS

Figure 1:
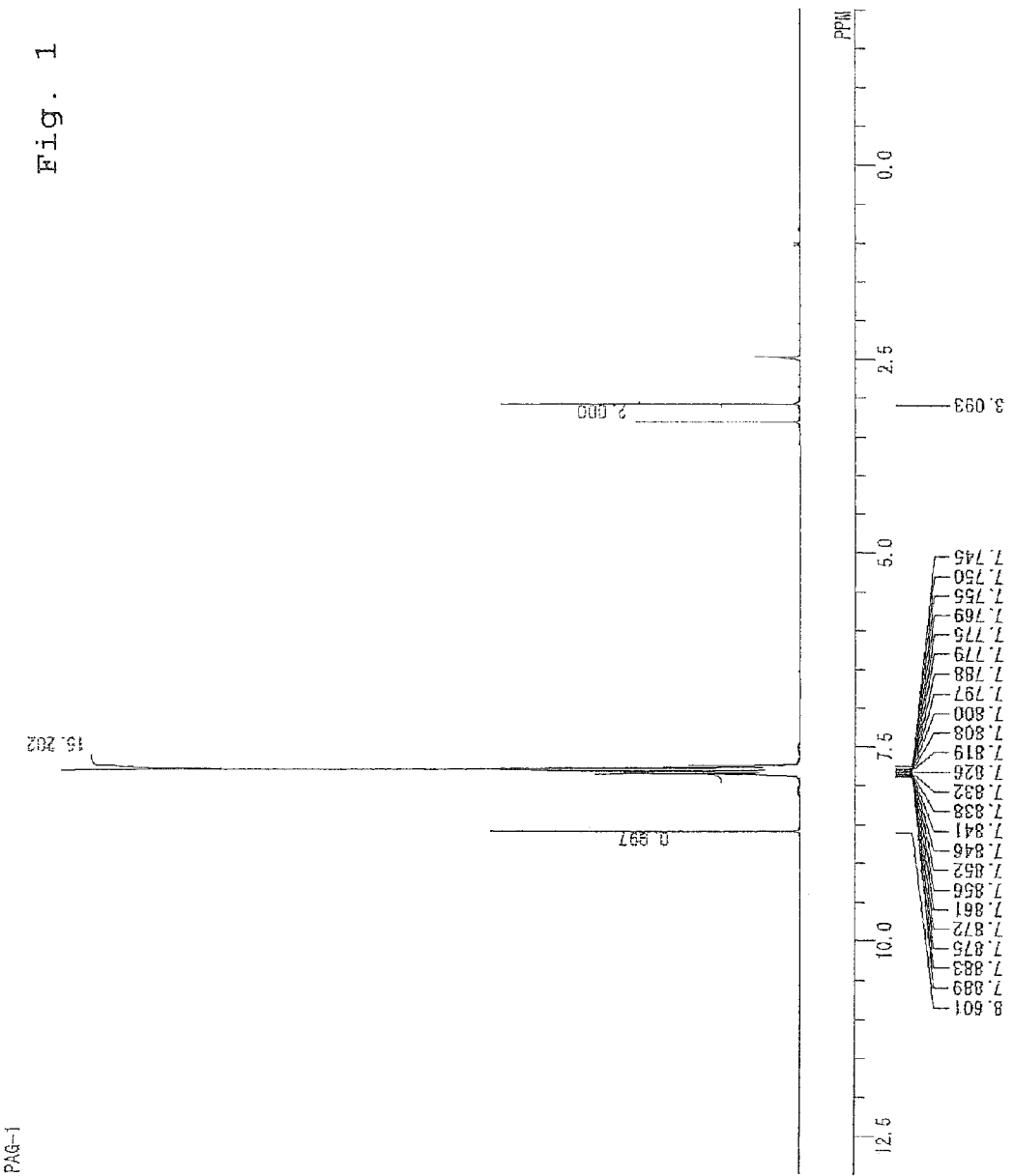
FIG. 1 is a spectrum of $^1$H-NMR/DMSO-$d_6$ of PAG-1 in Synthesis Example 1-9.

Hereinbelow, the present invention will be explained more specifically.

As described above, a photosensitive acid generator of the resist composition needs to have a sufficiently high solubility (compatibility) in a resist solvent and a resin, a good storage stability, in particular a good pattern profile form, a PED stability, a high resolution, a further wider depth of focus, and a good sensitivity, while conventional photosensitive acid generators do not satisfy all of these requirements. Deterioration of the pattern profile form on the mask blanks becomes a serious problem especially in processing of the photomask blanks, because it is also a cause of a pattern collapse as the integrated circuit pattern progresses toward further miniaturization in recent years.

Inventors of the present invention carried out the investigation extensively to achieve the object to provide; a novel sulfonate, effective for a chemically amplified resist composition, giving a chemically amplified resist composition which is especially excellent in resolution and pattern profile form without the problems as mentioned above; a photosensitive acid generator; a resist composition using the same; a photomask blank; and a patterning process. As a result, it was found that a 2-hydroxy-2,2-bistrifluoromethylethane sulfonate could be obtained by reacting 2,2-bistrifluoromethyloxirane, the industrially available starting raw material, with a sulfur compound such as sodium sulfite and sodium hydrogen sulfite, and that the resist composition using, as the acid generator, a compound typically represented by the sulfonium salt of sulfonic acid and the iodonium salt of sulfonic acid that were synthesized from the sulfonate as the intermediate raw material was excellent in properties such as the PED stability, the pattern form, the resolution, and the sensitivity thereby extremely useful as the resist composition for a fine and precision processing. Based on such information, the present invention could be accomplished.

Namely, the sulfonate, an intermediate raw material for the sulfonate represented by the general formula (2) useful for the photosensitive acid generator of the present invention, can be shown by the following general formula (1).

$$HO-C(CF_3)_2-CH_2SO_3^-M^+ \qquad (1)$$

(In the formula, M$^+$ represents a cation.)

Here, M$^+$ is not particularly restricted as far as it can exist as a stable sulfonate, but in view of simplicity in its synthesis and easiness in isolation of the sulfonate, a lithium ion, a sodium ion, a potassium ion, an ammonium ion, an iodonium ion, and a sulfonium ion are preferably used.

When M$^+$ is any of an ammonium ion, a sulfonium ion, and an iodonium ion, they can be shown by the following general formula (7).

$$(R^6)_{m'}A'^+ \qquad (7)$$

(In the formula, A' represents any of a nitrogen atom, a sulfur atom, and an iodine atom. Each R$^6$ independently represents a hydrogen atom, or a linear, a branched, or a cyclic alkyl, alkenyl, or oxoalkyl group, substituted or unsubstituted, having 1 to 10 carbon atoms, a substituted or an unsubstituted aryl, aralkyl, or aryl oxoalkyl group having 6 to 18 carbon atoms, or any two or more of R$^6$ may be bonded with each other to form a ring together with A' in the formula. However, when A' is a sulfur atom or an iodine atom, $R^6$ does not represent a hydrogen atom. "m'" is 4 when A' is a nitrogen atom, 3 when A' is a sulfur atom, and 2 when A' is an iodine atom.)

As a substituent in R6, a hydroxyl group, an alkoxyl group, a halogen atom, a carbonyl group, etc. are given, and specific examples of R6 include the followings.

Examples of an alkyl group include: a methyl group, an ethyl group, a propyl group, an isopropyl group, a n-butyl group, a sec-butyl group, a tert-butyl group, a pentyl group, a hexyl group, a heptyl group, an octyl group, a cyclopentyl group, a cyclohexyl group, a cycloheptyl group, a cyclopropylmethyl group, a 4-methylcyclohexyl group, a cyclohexylmethyl group, a norbornyl group, an adamantyl group, etc. Examples of an alkenyl group may include: a vinyl group, an allyl group, a propenyl group, a butenyl group, a hexenyl group, a cyclohexenyl group, etc. Examples of an oxoalkyl group may include: 2-oxocyclopentyl group, 2-oxocyclohexyl group, 2-oxopropyl group, 2-oxoethyl group, 2-cyclopentyl-2-oxoethyl group, 2-cyclohexyl-2-oxoethyl group, 2-(4-methylcyclohexyl)-2-oxoethyl group, etc. Examples of an aryl group may include: a phenyl group, a naphthyl group, thienyl group, an alkoxy phenyl groups such as 4-hydroxyphenyl group, p-methoxyphenyl group, m-methoxyphenyl group, o-methoxyphenyl group, an p-ethoxyphenyl group, p-tert-butoxyphenyl group, and m-tert-butoxy phenyl group, an alkyl phenyl group such as 2-methylphenyl group, 3-methylphenyl group, 4-methylphenyl group, an ethylphenyl group, 4-tert-butylphenyl group, 4-butylphenyl group, and a 2,4-dimethyl phenyl group, an alkyl naphthyl group such as a methylnaphthyl group, and an ethyl naphthyl group, an alkoxy naphthyl group such as a methoxy naphthyl group, and an ethoxy naphthyl group, a dialkyl naphthyl group such as a dimethyl naphthyl group, and a diethyl naphthyl group, and a dialkoxy naphthyl group such as a dimethoxy naphthyl group, and a diethoxy naphthyl group, etc. Examples of the aralkyl group may include: a benzyl group, a 1-phenylethyl group, a 2-phenethyl group, etc. Examples of the aryl oxoalkyl group may include: 2-aryl-2-oxoethyl group such as 2-phenyl-2-oxoethyl group, 2-(1-naphthyl)-2-oxoethyl group, 2-(2-naphthyl)-2-oxoethyl group, etc.

When A' is a nitrogen atom and any two or more of $R^6$ connect are bonded with each other to form a ring together with a nitrogen atom, a structure such as piperidine, morpholine, pyridine, quinoline, acridine, imidazole, benzimidazole, may be exemplified, and its nitrogen atom may be protonated or alkylated. Further, aryl group having a polymerizable substituent group such as an acryloyloxy group or a methacryloyloxy group may be exemplified, specifically, 4-(acryloyloxy)phenyl group, 4-(methacryloyloxy)phenyl group, 4-vinyloxyphenyl group, 4-vinylphenyl group, and so on.

In addition, when A' is a sulfur atom and any two of $R^6$ connect are bonded with each other to form a ring together with a sulfur atom, a structure such as tetrahydrothiophene, 1,4-thioxane, dibenzo thiofuran, phenoxthine, may be exemplified.

As an example of more specific $(R^6)_m{'}A'^+$, when A' is a nitrogen atom, ammonium, trimethyl ammonium, tetramethyl ammonium, triethyl ammonium, tributyl ammonium, tetrabutyl ammonium, trioctyl ammonium, anilinium, 2,6-dimethyl anilinium, N,N-dimethyl anilinium, benzyltrimethylammonium, benzyltriethylammonium, benzyltripropylammonium, N-benzyl-N,N-dimethyl anilinium, N-(p-methoxy)benzyl-N,N-dimethyl anilinium, etc. may be exemplified. When A' is a sulfur atom, triphenylsulfonium, 4-hydroxyphenyl diphenylsulfonium, bis(4-hydroxyphenyl) phenylsulfonium, tris(4-hydroxyphenyl)sulfonium, (4-tert-butoxyphenyl)diphenylsulfonium, bis(4-tert-butoxyphenyl) phenylsulfonium, tris(4-tert-butoxyphenyl)sulfonium, (3-tert-butoxyphenyl)diphenylsulfonium, bis(3-tert-butoxyphenyl)phenylsulfonium, tris(3-tert-butoxyphenyl)sulfonium, (3,4-ditert-butoxyphenyl)diphenylsulfonium, bis(3,4-ditert-butoxyphenyl)phenylsulfonium, tris(3,4-ditert-butoxyphenyl)sulfonium, diphenyl(4-thiophenoxyphenyl) sulfonium, (4-tert-butoxycarbonylmethyloxyphenyl) diphenylsulfonium, tris(4-tert-butoxycarbonylmethyloxyphenyl)sulfonium, (4-tert-butoxyphenyl)bis(4-dimethylaminophenyl)sulfonium, tris(4-dimethylaminophenyl)sulfonium, 2-naphthyl diphenylsulfonium, dimethyl-2-naphthylsulfonium, 4-hydroxyphenyl dimethylsulfonium, 4-methoxyphenyl dimethylsulfonium, trimethylsulfonium, 2-oxocyclohexyl cyclohexyl methylsulfonium, trinaphthylsulfonium, tribenzylsulfonium, diphenyl methylsulfonium, dimethyl phenylsulfonium, 2-oxo-2-phenylethylthiacyclopentanium, diphenyl 2-thienylsulfonium, 4-n-butoxynaphthyl-1-thiacyclopentanium, 2-n-butoxynaphthyl-1-thiacyclopentanium, 4-methoxy naphthyl-1-thiacyclopentanium, 2-methoxynaphthyl-1-thiacyclopentanium, 4-methylphenyl diphenylsulfonium, 4-ethylphenyl diphenylsulfonium, 4-tert-butylphenyl diphenylsulfonium, 4-cyclohexylphenyl diphenylsulfonium, 4-n-hexylphenyl diphenylsulfonium, 4-n-octylphenyl diphenylsulfonium, 4-methoxyphenyl diphenylsulfonium, 4-ethoxyphenyl diphenylsulfonium, 4-cyclohexyloxyphenyl diphenylsulfonium, 4-n-hexyloxyphenyl diphenylsulfonium, 4-n-octyloxyphenyl diphenylsulfonium, 4-dodecyloxyphenyl diphenylsulfonium, 4-trifluoromethylphenyl diphenylsulfonium, 4-trifluoromethyloxyphenyl diphenylsulfonium, 4-tert-butoxycarbonylmethyloxyphenyl diphenylsulfonium, 10-phenyl phenoxthinium may be exemplified.

More preferably triphenylsulfonium, 4-tert-butylphenyl diphenylsulfonium, 4-tert-butoxyphenyl diphenylsulfonium, tris(4-tert-butylphenyl)sulfonium, (4-tert-butoxycarbonylmethyloxyphenyl)diphenyl sulfonium, diphenyl methyl sulfonium, dimethylphenylsulfonium, 2-oxo-2-phenylethylthiacyclopentanium, 10-phenyl phenoxthinium, etc. are given. When A' is an iodine atom, bis(4-methylphenyl)iodonium, bis(4-ethylphenyl)iodonium, bis(4-tert-butylphenyl)iodonium, bis(4-(1,1-dimethylpropyl)phenyl)iodonium, 4-methoxyphenylphenyliodonium, 4-tert-butoxyphenylphenyliodonium, 4-acryloyloxyphenylphenyliodonium, 4-methacryloyloxyphenylphenyliodonium, etc. may be exemplified.

Then, a synthetic method in the sulfonate represented by the general formula (1), the intermediate raw material of the present invention, will be described.

The intermediate raw material sulfonate represented by the general formula (1) can be conveniently synthesized by reacting 2,2-bistrifluoromethyloxirane as the starting raw material with a sulfur compound such as a sulfite and a hydrogensulfite in water. The reaction temperature is 0 to 50° C., or preferably 20 to 50° C. The salt to react with 2,2-bistrifluoromethyloxylane is preferably sodium hydrogensulfite because it is cheap and can be easily handled.

By the method as described above, the sulfonate represented by the general formula (1), the intermediate raw material of the present invention, can be produced from cheap raw materials and in a convenient procedure. In addition, the method is extremely advantageous from the environmental view point because water is used as the solvent.

As to the sulfonate represented by the general formula (1) as the intermediate raw material of the present invention, its sodium salt, potassium salt, ammonium salt, and the like may be the useful synthesis intermediates. Namely, by the cationic exchange and acylation method which will be described later, they can be easily transformed to the sulfonium salt of sulfonic acid represented by the general formula (3) or (4) of the present invention or to the iodonium salt of sulfonic acid represented by the general formula (5) of the present invention, which is usable as the photosensitive acid generator. In addition, the ammonium salt can be used also as a precursor to a thermal acid generator, and thus it can be that, as a whole, the sulfonate represented by the general formula (1) has an extremely high application value as the intermediate raw material of the present invention.

In the present invention, the intended sulfonate represented by the following general formula (2) useful as the photosensitive acid generator can be synthesized by acylating the intermediate raw material sulfonate represented by the general formula (1).

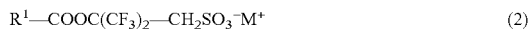

$$R^1-COOC(CF_3)_2-CH_2SO_3^- M^+ \quad (2)$$

(In the formula, $R^1$ represents a linear, a branched, or a cyclic monovalent hydrocarbon group having 1 to 50 carbon atoms optionally containing a hetero atom. $M^+$ represents the same as before.)

For the acylation reaction, heretofore known ester-production methods, such as a reaction with an acylating agent and a reaction with a carboxylic acid, can be applied, but the reaction with an acylating agent is particularly preferable. In the reaction using the acylating agent, the sulfonate represented by the general formula (1) is reacted in a solvent, singly or in a mixture of two or more kinds, selected preferably from chlorinated solvents such as methylene chloride, chloroform, and trichloroethylene, hydrocarbons such as hexane, heptane, benzene, toluene, xylene, and cumene, ethers such as dibutyl ether, diethyleneglycol diethyl ether, diethyleneglycol dimethyl ether, tetrahydrofurane, and 1,4-dioxane, nitriles such as acetonitrile, ketones such as acetone and 2-butanone, esters such as ethyl acetate and n-butyl acetate, and non-protonic polar solvents such as N,N-dimethylformamide, dimethyl sulfoxide, and hexamethylphosphoric triamide, with an acylating agent, such as a carboxyl chloride or a carboxylic anhydride, a mixed onium acid anhydride of a carboxylic acid and trifluoroacetic acid, and a mixed acid anhydride of a carboxylic acid and pivalic acid, and with a basic compound such as triethylamine, diisopropyl ethyl amine, N,N-dimethylaniline, pyridine, and 4-dimethylaminopyridine, by adding them successively or simultaneously. In the reaction using the acylating agents such as an acid anhydride, the reaction can also be done in the presence of an acid catalyst, instead of a basic compound, selected from inorganic acids such as hydrochloric acid, hydrobromic acid, sulfuric acid, and nitric acid, and organic acids such as oxalic acid, trifluoroacetic acid, methanesulfonic acid, benzene sulfonic acid, and p-toluene sulfonic acid. Temperature of the acylation reaction can be selected appropriately according to a kind of the acylating agent and reaction conditions, but generally it is preferably from about −50° C. to about boiling point of the solvent, or more preferably from about −20° C. to about room temperature. The amount of the acylating agent is in the range of 1 to 40 moles, or preferably 1 to 5 moles, relative to 1 mole of the alcoholic compound, though depending on their structures. The reaction with a carboxylic acid is a dehydration reaction from a corresponding carboxylic acid and sulfonate, and is usually carried out in the presence of an acid catalyst. The amount of the carboxylic acid is in the range of 1 to 40 moles, or preferably 1 to 5 moles, relative to 1 mole of the alcoholic compound, though depending on their structures. Examples of the acid catalysts include inorganic acids such as hydrochloric acid, hydrobromic acid, sulfuric acid, and nitric acid, and organic acids such as oxalic acid, trifluoroacetic acid, methanesulfonic acid, benzene sulfonic acid, and p-toluene sulfonic acid, and they can be used singly or in a mixture thereof. The amount of the acid catalyst to be used is 0.001 to 1 mole, or preferably 0.01 to 0.05 mole, relative to 1 mole of the alcoholic compound. The solvent may be exemplified by the same solvents as those mentioned in the reaction with the esterification agents, and the reaction temperature is generally from about −50° C. to about boiling point of the solvent. The reaction may also be done with removing generated water outside the system by an azeotropic distillation in a solvent including hydrocarbons such as hexane, heptane, benzene, toluene, xylene, and cumene. In this case, water may be distilled out under reflux at a normal pressure and a boiling point of the solvent, but the water removal may also be done under reduced pressure at the temperature below a boiling point of the solvent.

In the step of obtaining the sulfonate represented by the general formula (2) from the intermediate raw material sulfonate represented by the general formula (1), $M^+$ is preferably any of an ammonium ion, a sulfonium ion, and an iodonium ion in view of the solubility into the reaction solvent. When $M^+$ is a sulfonium ion or an iodonium ion, they can be used as the subsequent photosensitive acid generator. When $M^+$ is an ammonium ion, it can be used as a thermal acid generator.

In the sulfonate represented by the general formula (2), the option of a molecular design can be made wider by selecting the acylating agent. Accordingly, a thermal acid generator or a photosensitive acid generator suitable for various conditions can be prepared, and thus it can be that its application value is extremely high.

Here, as a substituent in $R^1$, specific examples of $R^1$ include the followings.

Example of the alkyl group may include: methyl group, an ethyl group, propyl group, isopropyl group, n-butyl group, sec-butyl group, tert-butyl group, pentyl group, hexyl group, heptyl group, octyl group, cycloheptyl group, cyclohexyl group, cycloheptyl group, cyclopropylmethyl group, 4-methylcyclohexyl group, cyclohexylmethyl group, norbornyl group, 1-adamantyl group, 1-adamantylmethyl group, steroid structure component group, etc. Example of the oxoalkyl group may include: 2-oxocyclopentyl group, 2-oxocyclohexyl group, 4-oxocyclohexyl group, 2-oxopropyl group, 2-oxoethyl group, 2-cyclopentyl-2-oxoethyl group, 2-cyclohexyl-2-oxoethyl group, 2-(4-methylcyclohexyl)-2-oxoethyl group, 4-oxa-tricyclo[4.2.1.0$^{3,7}$]nonane-5-one-9-yl group, 4-oxo-1-adamantyl group, etc. Example of the aryl group may include: phenyl group, 1-naphthyl group, 2-naphthyl group, anthranil group, thienyl group, alkoxyphenyl group such as 4-hydroxyphenyl group, 4-methoxyphenyl group, 3-methoxyphenyl group, 2-methoxyphenyl group, 4-ethoxyphenyl group, 4-tert-butoxyphenyl group, and 3-tert-butoxyphenyl group, alkylphenyl group such as 2-methylphenyl group, 3-methylphenyl group, 4-methylphenyl group, 4-ethylphenyl group, 4-tert-butylphenyl group, 4-n-butylphenyl group, and 2,4-dimethylphenyl group, alkylnaphthyl group such as methylnaphthyl group, and ethylnaphthyl group, alkoxynaphthyl group such as methoxynaphthyl group, and ethoxynaphthyl group, dialkylnaphthyl group such as dimethylnaphthyl group, and diethylnaphthyl group, and dialkoxynaphthyl group such as dimethoxynaphthyl group, and diethoxynaphthyl group, etc. Example of the aralkyl group may include: benzyl group, 1-phenylethyl group, and 2-phenylethyl group, etc. Example of the aryloxoalkyl group may include: 2-aryl-2-oxoethyl group such as 2-phenyl-2-oxoethyl group, 2-(1-naphthyl)-2-oxoethyl group, 2-(2-naphthyl)-2-oxoethyl group, etc. In addition, vinyl group, isopropenrl group, etc. are given.

Groups which are preferably used in $R^1$ in particular include: tert-butyl group, cyclohexyl group, 1-adamantyl group, 1-adamantyl methyl group, 4-oxa-tricyclo[4.2.1.0$^{3,7}$] nonane-5-one-9-yl group, 4-oxo-1-adamantyl group, steroid structure-containing group, phenyl group, 1-naphthyl group, isopropenyl group, etc.

As a specific example of sulfonic acid salt shown in the general formula (2), a sulfonium salt of sulfonic acid shown in the following general formula (3) can be given.

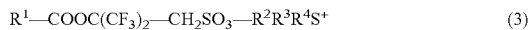

$$R^1\text{---COOC}(CF_3)_2\text{---}CH_2SO_3\text{---}R^2R^3R^4S^+ \quad (3)$$

(In the formula, $R^1$ represents the same as before. Each $R^2$, $R^3$, and $R^4$ independently represents a linear or a branched alkyl, alkenyl, or oxoalkyl group, substituted or unsubstituted, having 1 to 10 carbon atoms, a substituted or an unsubstituted aryl, aralkyl, or aryl oxoalkyl group having 6 to 18 carbon atoms, or any two or more of $R^2$, $R^3$, and $R^4$ may be bonded with each other to form a ring together with a sulfur atom in the formula.)

Specific examples of $R^2$, $R^3$, and $R^4$ in the general formula (3) include the followings.

Examples of the alkyl group include: a methyl group, an ethyl group, a propyl group, an isopropyl group, a n-butyl group, a sec-butyl group, a tert-butyl group, a pentyl group, a hexyl group, a heptyl group, an octyl group, a cyclopentyl group, a cyclohexyl group, a cycloheptyl group, a cyclopropylmethyl group, a 4-methylcyclohexyl group, a cyclohexylmethyl group, a norbornyl group, an adamantyl group, etc. Examples of the alkenyl group may include: a vinyl group, an allyl group, a propenyl group, a butenyl group, a hexenyl group, a cyclohexenyl group, etc. Examples of an oxoalkyl group may include: 2-oxocyclopentyl group, 2-oxocyclohexyl group, 2-oxopropyl group, 2-oxoethyl group, 2-cyclopentyl-2-oxoethyl group, 2-cyclohexyl-2-oxoethyl group, 2-(4-methylcyclohexyl)-2-oxoethyl group, etc. Examples of the aryl group may include: a phenyl group, a naphthyl group, thienyl group, 4-hydroxyphenyl group, an alkoxy phenyl groups such as 4-methoxyphenyl group, 3-methoxyphenyl group, 2-methoxyphenyl group, an 4-ethoxyphenyl group, 4-tert-butoxyphenyl group, and 3-tert-butoxy phenyl group, an alkyl phenyl group such as 2-methylphenyl group, 3-methylphenyl group, 4-methylphenyl group, an 4-ethylphenyl group, 4-tert-butylphenyl group, 4-n-butylphenyl group, and a 2,4-dimethyl phenyl group, an alkyl naphthyl group such as a methylnaphthyl group, and an ethyl naphthyl group, an alkoxy naphthyl group such as a methoxy naphthyl group, and an ethoxy naphthyl group, a dialkyl naphthyl group such as a dimethyl naphthyl group, and a diethyl naphthyl group, and a dialkoxy naphthyl group such as a dimethoxy naphthyl group, a diethoxy naphthyl group, and etc. Examples of the aralkyl group may include: a benzyl group, a 1-phenylethyl group, a 2-phenethyl group, and etc. Examples of an aryl oxoalkyl group may include: 2-aryl-2-oxoethyl group such as 2-phenyl-2-oxoethyl group, 2-(1-naphthyl)-2-oxoethyl group, 2-(2-naphthyl)-2-oxoethyl group, and etc. In addition, when any two or more of $R^2$, $R^3$, and $R^4$ may be bonded with each other to form a ring together with a sulfur atom in the formula, as a group which forms these ring structures, bivalent organic groups such as 1,4-butylene, 3-oxa-1,5-penylene are given. Further, as a substituent, aryl group having a polymerizable substituent such as acryloyloxy group and methacryloyloxy group, more specifically, 4-acryloyloxyphenyl group, 4-methacryloyloxyphenyl group, 4-acryloyloxy-3,5-dimethylphenyl group, 4-methacryloyloxy-3,5-dimethylphenyl group, 4-vinyloxyphenyl group, 4-vinylphenyl group etc. are given.

In addition, specific examples of sulfonium cation include: triphenylsulfonium, 4-hydroxyphenyldiphenylsulfonium, bis(4-hydroxyphenyl)phenylsulfonium, tris(4-hydroxyphenyl)sulfonium, 4-tert-butoxyphenyldiphenylsulfonium, bis(4-tert-butoxyphenyl)phenylsulfonium, tris(4-tert-butoxyphenyl)sulfonium, 3-tert-butoxyphenyldiphenylsulfonium, bis(3-tert-butoxyphenyl)phenylsulfonium, tris(3-tert-butoxyphenyl)sulfonium, 3,4-di-tert-butoxyphenyldiphenylsulfonium, bis(3,4-di-tert-butoxyphenyl)phenylsulfonium, tris(3,4-di-tert-butoxyphenyl)sulfonium, diphenyl(4-thiophenoxyphenyl)sulfonium, 4-tert-butoxycarbonylmethyloxyphenyldiphenylsulfonium, tris(4-tert-butoxycarbonylmethyloxyphenyl)sulfonium, (4-tert-butoxyphenyl)bis(4-dimethylaminophenyl)sulfonium, tris(4-dimethylaminophenyl)sulfonium, 2-naphthyldiphenylsulfonium, (4-hydroxy-3,5-dimethylphenyl)diphenylsulfonium, (4-n-hexyloxy-3,5-dimethylphenyl)diphenylsulfonium, dimethyl(2-naphthyl)sulfonium, 4-hydroxyphenyldimethylsulfonium, 4-methoxyphenyldimethylsulfonium, trimethylsulfonium, 2-oxocyclohexylcyclohexylmethylsulfonium, trinaphthylsulfonium, tribenzylsulfonium, diphenylmethylsulfonium, dimethylphenylsulfonium, 2-oxo-2-phenylethylthiacyclopentanium, diphenyl2-thienylsulfonium, 4-n-butoxynaphthyl-1-thiacyclopentanium, 2-n-butoxynaphthyl-1-thiacyclopentanium, 4-methoxynaphthyl-1-thiacyclopentanium, 2-methoxynaphthyl-1-thiacyclopentanium, and etc. More preferably triphenylsulfonium, 4-tert-butylphenyldiphenylsulfonium, 4-tert-butoxyphenyldiphenylsulfonium, tris(4-tert-butylphenyl)sulfonium, 4-tert-butoxycarbonylmethyloxyphenyldiphenylsulfonium, and etc. are given. Further, 4-methacryloyloxyphenyldiphenylsulfonium, 4-acryloyloxyphenyldiphenylsulfonium, 4-methacryloyloxyphenyldimethylsulfonium, 4-acryloyloxyphenyldimethylsulfonium, (4-methacryloyloxy-3,5-dimethylphenyl)diphenylsulfonium, (4-acryloyloxy-3,5-dimethylphenyl)diphenylsulfonium, etc. are given. As for these polymerizable sulfonium cations, a Japanese Patent Laid-Open No. H04-230645, a Japanese Patent Laid-Open No. 2005-84365 etc. may be reffered, and these polymerizable sulfonium salts may be used as a monomer of a constitution ingredient of a polymer described later.

In this case, as a more specific example of a sulfonium salt of sulfonic acid shown in the general formula (3), a sulfonium salt of sulfonic acid shown in the following general formula (4) can be given.

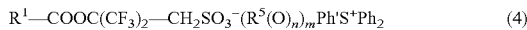

$$R^1\text{---COOC}(CF_3)_2\text{---}CH_2SO_3^-(R^5(O)_n)_m Ph'S^+Ph_2 \quad (4)$$

(In the formula, $R^1$ represents the same as before. $R^5$ represents a linear, a branched, or a cyclic alkyl or alkenyl group, substituted or unsubstituted, having 1 to 20 carbon atoms, or a substituted or an unsubstituted aryl group having 6 to 14 carbon atoms. "m" represents an integer of 1 to 5 and "n" represents 0 or 1. Ph represents a phenyl group. Ph' represents a phenyl group whose "m" hydrogen atoms are substituted by a $R^5(O)_n$— group.)

In the general formula (4), a position to be substituted of $R^5(O)_n$— group is not particularly restricted, but the fourth place or the third place of the phenyl group is preferable. More preferably it is the fourth place. As $R^5$, methyl group, ethyl group, n-propyl group, sec-propyl group, cyclopropyl group, n-butyl group, sec-butyl group, isobutyl group, tert-butyl group, n-pentyl group, cyclopentyl group, n-hexyl group, cyclohexyl group, n-octyl group, n-decyl group, n-dodecyl group, trifluoromethyl group, phenyl group, 4-methoxyphenyl group, 4-tert-butylphenyl group, further when n=1, acryloyl group, methacryloyl group, vinyl group, allyl group are given. "m" represents an integer of 1 to 5, preferably 1, and "n" represents 0 or 1.

In addition, specific examples of sulfonium cation include: 4-methylphenyldiphenylsulfonium, 4-ethylphenyl diphenylsulfonium, 4-tert-butylphenyldiphenylsulfonium, 4-cyclohexylphenyldiphenylsulfonium, 4-n-hexylphenyldiphenylsulfonium, 4-n-octylphenyldiphenylsulfonium, 4-methoxyphenyldiphenylsulfonium, 4-ethoxyphenyldiphenylsulfonium, 4-tert-butoxyphenyldiphenylsulfonium, 4-cyclohexyloxyphenyldiphenylsulfonium, 4-n-hexyloxyphenyldiphenylsulfonium, 4-n-octyloxyphenyldiphenylsulfonium, 4-dodecyloxyphenyldiphenylsulfonium, 4-trifluoromethylphenyldiphenylsulfonium, 4-trifluoromethyloxyphenyldiphenylsulfonium, 4-tert-butoxycarbonylmethyloxyphenyldiphenylsulfonium, 4-methacryloyloxyphenyldiphenylsulfonium, 4-acryloyloxyphenyldiphenylsulfonium, (4-n-hexyloxy-3,5-dimethylphenyl)diphenylsulfonium, (4-methacryloyloxy-3,5-dimethylphenyl)diphenylsulfonium, (4-acryloyloxy-3,5-dimethylphenyl)diphenylsulfonium, etc.

As a specific example of sulfonic acid salt shown in the general formula (2), an iodonium salt of sulfonic acid shown in the following general formula (5) can be given.

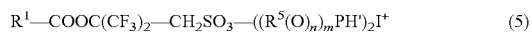

(In the formula, $R^1$ represents the same as before. $R^5$ represents a linear, a branched, or a cyclic alkyl or alkenyl group, substituted or unsubstituted, having 1 to 20 carbon atoms, or a substituted or an unsubstituted aryl group having 6 to 14 carbon atoms. "m" represents an integer of 1 to 5 and "n" represents 0 or 1. Ph' represents a phenyl group whose "m" hydrogen atoms are substituted by a $R^5(O)$— group.)

In the general formula (5), a position to be substituted of $R^5(O)_n$— group is not particularly restricted, but the fourth place or the third place of the phenyl group is preferable.

More preferably it is the fourth place. As $R^5$, methyl group, ethyl group, n-propyl group, sec-propyl group, cyclopropyl group, n-butyl group, sec-butyl group, isobutyl group, tert-butyl group, n-pentyl group, cyclopentyl group, n-hexyl group, cyclohexyl group, n-octyl group, n-decyl group, n-dodecyl group, trifluoromethyl group, phenyl group, 4-methoxyphenyl group, 4-tert-butylphenyl group, further when n=1, acryloyl group, methacryloyl group, vinyl group, allyl group are given. "m" represents an integer of 1 to 5, preferably 1, and "n" represents 0 or 1.

In addition, specific examples of iodonium cation include: diphenyliodonium, bis(4-methylphenyl)iodonium, bis(4-(1,1-dimethylethyl)phenyl)iodonium, bis(4-(1,1-dimethylpropyl)phenyl)iodonium, (4-(1,1-dimethylethoxy)phenyl)phenyliodonium, etc.

The sulfonium salt of sulfonic acid represented by the general formula (3) or (4) and the iodonium salt of sulfonic acid represented by the general formula (5) can be used for a resist composition as the photosensitive acid generator generating a sulfonic acid represented by the general formula (6) of the present invention, and this resist composition can be applied to the patterning.

Meanwhile, an ammonium salt and the like useful as an intermediate of the sulfonate represented by the general formula (2) giving the photosensitive acid generator of the present invention can be synthesized from the sulfonate represented by the general formula (1), the intermediate raw material of the present invention, by the method that will be described later. Examples of the ammonium salt include a salt of the tertiary ammonium such as trimethyl ammonium, triethyl ammonium, tributyl ammonium, and N,N-dimethylanilinium, and a salt of the quaternary ammonium such as tetramethyl ammonium, tetraethyl ammonium, and tetrabutyl ammonium.

Here, as one example of the synthetic methods of the sulfonate of the present invention represented by the general formula (2), one example of the synthetic methods of the sulfonium salt of sulfonic acid represented by the general formula (3) will be described.

Firstly, as described above, the intermediate raw material sulfonate represented by the general formula (1) is synthesized by reacting 2,2-bistrifluoromethyloxylane with a sulfur compound such as a sulfite and a hydrogen sulfite. Here, sodium hydrogen sulfite is used as the reaction sulfur compound agent to synthesize the sodium sulfonate, because it is inexpensive and can be easily handled and thus is preferable, but the agent is not limited to it.

Then, the obtained sodium sulfonate is ion-exchanged with a sulfonate such as a sulfonium halide to synthesize the compound whose $M^+$ in the general formula (1) is a sulfonate. Meanwhile, the ion-exchange reaction is elaborated in Japanese Patent Application Laid-Open No. 2007-145797 and so on. For example, a mixture containing the sulfonium halide is reacted in a bilayer system of dichloromethane-water, the water layer is removed, and then the organic layer is concentrated. In this way, the intended sulfonate can be synthesized and recovered. The sulfonate may be ion-exchanged after once isolated or as a crude substance.

Subsequently, the intended sulfonium salt of sulfonic acid represented by the general formula (3) can be obtained by acylating the obtained sulfonium salt of sulfonic acid. The acylation may be done in the way as mentioned before.

The steps are shown in the following scheme.

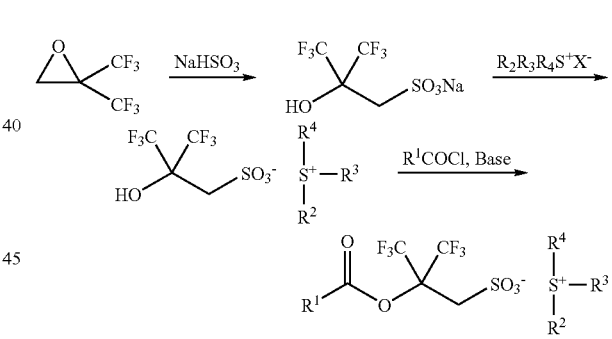

(In the formulae, $R^1$, $R^2$, $R^3$, and $R^4$ represent the same as before. $X^-$ represents an anion such as $I^-$, $Br^-$, $Cl^-$, and $MeOSO_3^-$.)

As described above, the intermediate raw material sulfonate of the present invention represented by the general formula (1) and the intended sulfonate represented by the general formula (2) useful as the photosensitive acid generator can be synthesized without including complicated steps and expensive raw materials.

In addition, a sulfonium salt of sulfonic acid other than triphenyl sulfonium, an iodonium salt of sulfonic acid, and the like can also be synthesized by using other sulfonium halides and iodonium halides in a similar manner.

A sulfonate such as a sulfonium halide and an iodonium salt such as an iodonium halide, which are used in the cation-exchange, can be synthesized with referring to; The Chemistry of Sulfonium Group, Part 1, John-Wiley & Sons (1981) Chap. 11. 267-312; Advanced Photochemistry, Vol. 17, John- Wiley & Sons (1992) 313-355; J. Org. Chem., 1988, 53, 5571-5573; Japanese Patent Application Laid-Open No. H08-311018; Japanese Patent Application Laid-Open No. H09-15848; Japanese Patent Application Laid-Open No. 2001-122850; Japanese Patent Application Laid-Open No. H07-25846; Japanese Patent Application Laid-Open No. 2001-181221; Japanese Patent Application Laid-Open No. 2002-193887; Japanese Patent Application Laid-Open No. 2002-193925, and so on. In addition, an onium cation containing an acryloyloxy group or a methacryloyloxy group as the polymerizable substituent group can be synthesized by reacting an existing hydroxyphenyl diphenylsulfonium halide with acryloyl chloride or methacryloyl chloride under a basic condition according to the methods described in Japanese Patent Application Laid-Open No. H04-230645, Japanese Patent Application Laid-Open No. 2005-84365, and so on.

The photosensitive acid generator of the present invention is the sulfonate represented by the general formula (2) that is synthesized from an intermediate raw material sulfonate represented by the general formula (1). Specifically, the generator is the compound typically represented by the sulfonium salt of sulfonic acid represented by the general formula (3) or (4) and the iodonium salt of sulfonic acid represented by the general formula (5). These respond to a high energy beam such as a UV ray, a far ultraviolet ray, an electron beam, an X-ray, an excimer laser, a γ-beam, and a synchrotron radiation beam to generate the sulfonic acid represented by the following general formula (6), and are used as the photosensitive acid generator for a chemically amplified resist composition.

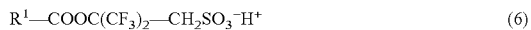

(6)

(In the formula, $R^1$ represents a linear, a branched, or a cyclic monovalent hydrocarbon group having 1 to 50 carbon atoms optionally containing a hetero atom.)

$R^1$ in the general formula (6) is the same as $R^1$ in the general formula (2), and the specific sulfonic acids are shown below. However, the photosensitive acid generator of the present invention is not limited to them.

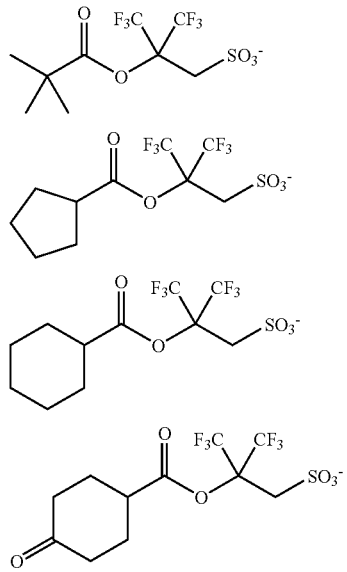

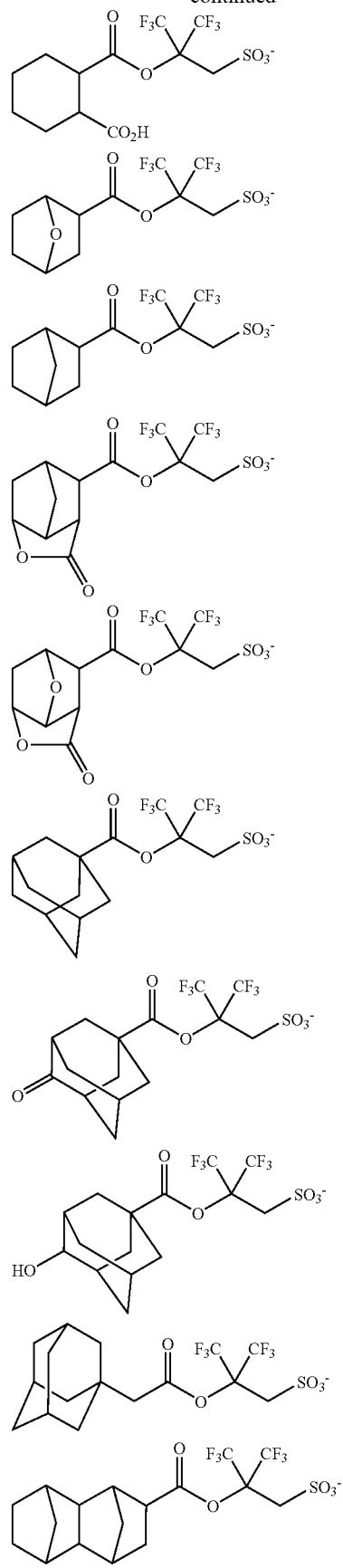

-continued

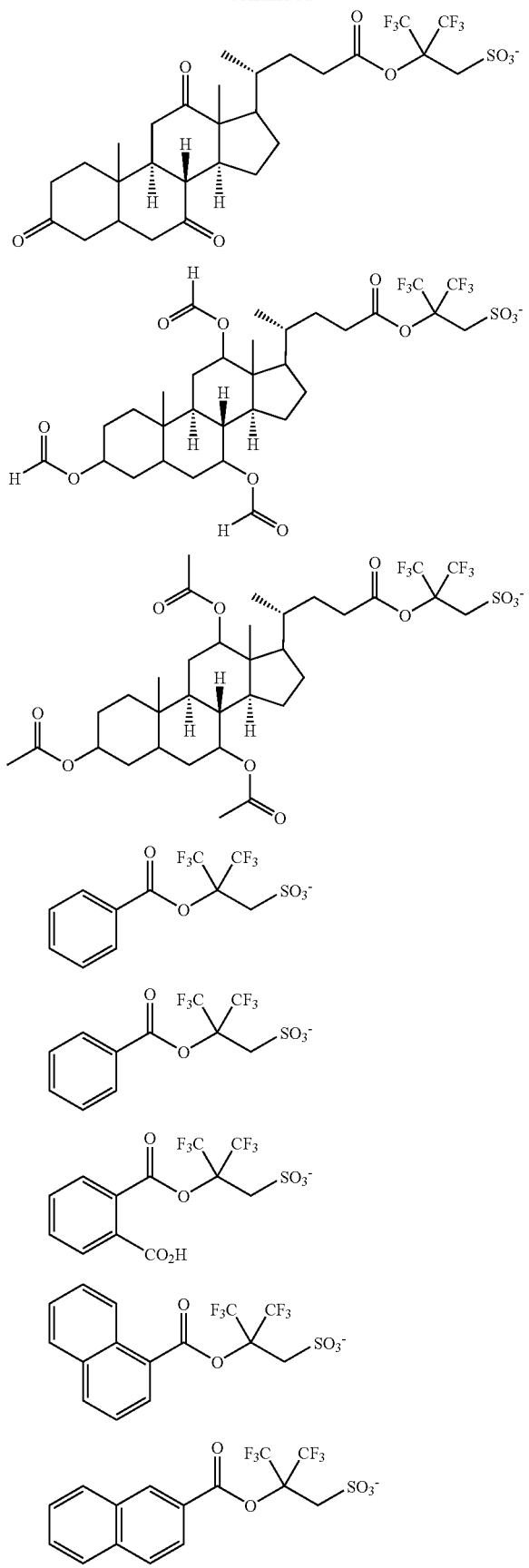

-continued

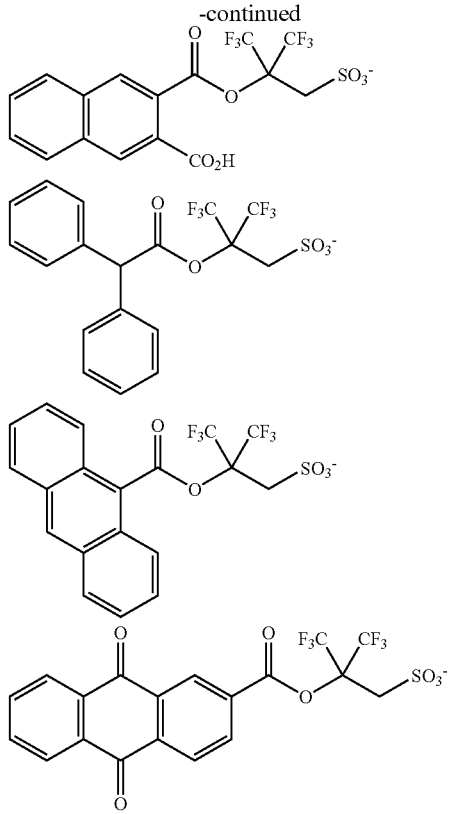

Examples of particularly preferably used $R^1$ include a tert-butyl group, a cyclohexyl group, a 1-adamantyl group, a 1-adamantylmethyl group, a 4-oxa-tricyclo[4.2.1.0$^{3,7}$] nonane-5-one-9-yl group, a 4-oxo-1-adamantyl group, a steroid structure-containing group, a phenyl group, a 1-naphthyl group, and the like.

For example, when $R^1$ contains a cycloalkyl group, the acid diffusion is suppressed as compared with a linear structure, thereby improving resolution, exposure margin, and the like. Particularly preferable case is in that $R^1$ is an adamantly group, and in this case the acid diffusion can be appropriately controlled because of its rigid structure and appropriate molecular size. As a result, a resist composition containing this shows a high dissolution contrast and a good pattern profile after development.

When $R^1$ contains an aromatic ring like a benzene ring or a naphthalene ring, not only the acid diffusion can be controlled because of its bulky structure similar to the alicyclic hydrocarbon structure but also the transmittance and the acid generating efficiency can be controlled because of the light absorption by it. Further, in a polymer matrix based on an aromatic ring like polyhydoroxy styrene in a KrF and an electron beam lithography, the photosensitive acid generator having an aromatic ring in the present invention has an affinity with the polymer, suggesting that it can be dispersed easily and uniformly. Owing to the uniform dispersion of the acid, a rectangular pattern form can be obtained after development.

When the ratio of an acid-labile group contained in a base polymer of a resist composition is high or it has such a structure so as to facilitate an acid diffusion (for example, in the case when a protection group has a non-alicyclic or a non-rigid structure), a high dissolution contrast can be obtained by using the photosensitive acid generator having a steroid structure in its $R^1$. This is owing to a high suppression effect of the acid diffusion caused by an extremely large molecular size of the steroid structure. In particular, a dehydrocholic acid derivative and the like are preferable in view of availability of their raw materials, easy purification, and the like.

When $R^1$ further contains a polar group such as a carbonyl group, a hydroxy group, or a carboxylic acid, an excellent exposure margin and depth of focus are obtained. It is assumed that this is caused by uniform dispersion of PAG in a polymer matrix because of its affinity with many polar units contained in a base resin of a resist composition. Especially, when $R^1$ has a norbornane lactone structure, it shows a good pattern profile because a high suppression effect of the diffusion and a uniform dispersibility can be assumed due to both effects of the rigid skeleton and the polar group in it.

In the ArF lithography using a (meth)acrylic acid resin, a photosensitive acid generator generating a strong acid such as $\alpha,\alpha'$-difluorosulfonic acid is usually used. In this case, when a considerably unstable group, such as a tertiary ester or an acetal group, is used as the acid-labile group contained in the resin, there may be the case that a deprotection reaction proceeds excessively thereby leading to an insufficient contrast. Accordingly, in such a case, the photosensitive acid generator of the present invention can be used. In this highly reactive protection group as mentioned above, the deprotection reaction can take place sufficiently even with the acid strength of the photosensitive acid generator of the present invention, while the deprotection reaction does not proceed excessively because the acid strength is not so high as $\alpha,\alpha'$-difluorosulfonic acid.

One big feature of the photosensitive acid generator of the present invention including the sulfonate represented by the general formula (2), specifically the sulfonate represented by the general formulae (3) to (5), lies in that the structure represented by $R^1$ can be easily changed to various structures by the acylation method as described before. In other words, freedom of the structural change is large, and thus each property can be controlled easily by changing the acyl group. Therefore, the photosensitive acid generator having the $R^1$ structure most suitable for the intended purpose can be selected according to an exposure condition, a kind of a polymer, a composition, and the like. Especially when $R^1$ has a bulky structure like an alicyclic hydrocarbon and an aromatic ring, an excellent pattern form with a little sparse/dense dependency can be obtained because diffusion of the generated acid can be appropriately suppressed.

Further, the photosensitive acid generator of the present invention using the sulfonate represented by the general formula (2), specifically represented by the general formulae (3) to (5), has an electron-withdrawing trifluoromethyl group at the $\beta$-position of the sulfo group, and because of this its acid strength is weaker than an $\alpha$-fluorosulfonic acid and stronger than an alkanesulfonic acid and an arene sulfonic acid. Accordingly, both an excellent resolution and a satisfactory environmental stability can be obtained in the KrF lithography and the electron beam lithography. In addition, as mentioned above, when $R^1$ has a bulky structure, an excellent pattern form with a little sparse/dense dependency can be obtained because diffusion of the generated acid can be appropriately suppressed. Namely, a resist composition using the photosensitive acid generator of the present invention shows excellent resist characteristics satisfying both a high resolution and an appropriate diffusion control. Furthermore, as mentioned before, an excellent pattern form can be obtained even in the ArF lithography by combining the photosensitive acid generator of the present invention with a photosensitive acid generator generating a strong acid like an $\alpha$-fluorosulfonic acid.

The present invention provides the photosensitive acid generator using the sulfonate represented by the general formula (2) that generates the sulfonic acid represented by the general formula (6), specifically the generator using the sulfonate represented by the general formulae (3) to (5). Further, the present invention provides a resist composition containing the photosensitive acid generator generating the sulfonic acid represented by the general formula (6), namely the chemically amplified resist composition for manufacturing an integrated circuit containing the photosensitive acid generator generating the sulfonic acid represented by the general formula (6) by responding to radial rays such as a UV ray, a far ultraviolet ray, an electron beam, an X-ray, an excimer laser, a $\gamma$-beam, and a synchrotron radiation beam. These resist compositions may be used as a positive type or as a negative type. In view of the resolution, especially a positive resist composition is used more preferably.

In this case, it is preferable that the positive resist composition contain, in addition to the photosensitive acid generator including the sulfonate represented by the general formula (2) generating the sulfonic acid represented by the general formula (6), specifically the sulfonium salt of sulfonic acid represented by the general formula (3) or (4), or the iodonium salt of sulfonic acid represented by the general formula (5) (hereinafter, these are referred to as collectively the photosensitive acid generator of the present invention), (A) a base resin whose solubility in an alkaline developer is changed by action of an acid, (B) an organic solvent, and in addition, as appropriate, (C) an acid generator other than the photosensitive acid generator of the present invention, (D) a quencher, and (E) a surfactant.

It is preferable that the negative resist composition contain, in addition to the photosensitive acid generator of the present invention, (A') a base resin that is soluble in an alkaline developer, (B) an organic solvent, and in addition, as appropriate, (C) an acid generator other than the photosensitive acid generator of the present invention, (D) a quencher, (E) a surfactant, and (F) a crosslinker crosslinked by an acid.

Hereinbelow, each component will be described in detail.

It is preferable that the amount of the photosensitive acid generator of the present invention be 0.1 to 10 parts by mass, in particular, 0.1 to 5 parts by mass, relative to 100 parts by mass of the component (A) or (A').

The component (A) resin whose solubility in an alkaline developer is changed by the action of an acid is not particularly restricted, but may contain, in the case of the chemically amplified positive resist composition, one or more of any repeating unit represented by the following general formulae (11) to (15).

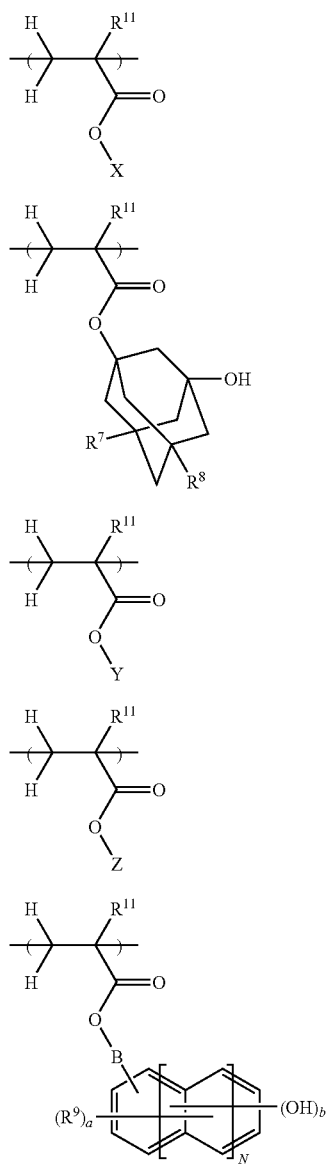

(In the formulae, $R^{11}$ represents a hydrogen atom, a fluorine atom, a methyl group, or a trifluoromethyl group. Each $R^7$ and $R^8$ independently represents a hydrogen atom or a hydroxyl group. X represents an acid-labile group. Y represents a substituent group having a lactone structure. Z represents a hydrogen atom, a fluoroalkyl group having 1 to 15 carbon atoms, or a fluoroalcohol-containing substituent group having 1 to 15 carbon atoms. N represents an integer of 0 to 2. $R^9$ represents a hydrogen atom, or an alkyl group having 1 to 10 carbon atoms. B represents a single bond or a divalent organic group having 1 to 10 carbon atoms, which may be substituted by an oxygen atom. "a" represents an integer of 0 to 3, and "b" represents an integer of 1 to 3.)

The polymer containing the repeating unit represented by the general formula (11) generates a carboxylic acid by action of an acid thereby giving an alkaline-soluble polymer.

As the acid-labile X group, various kinds can be used. Specifically, a group represented by the following general formulae (L1) to (L4) and (L2-2), a tertiary alkyl group having 4 to 20, preferably 4 to 15 carbon atoms, a trialkylsilyl group whose each alkyl group has 1 to 6 carbon atoms, an oxoalkyl group having 4 to 20 carbon atoms, and the like may be exemplified.

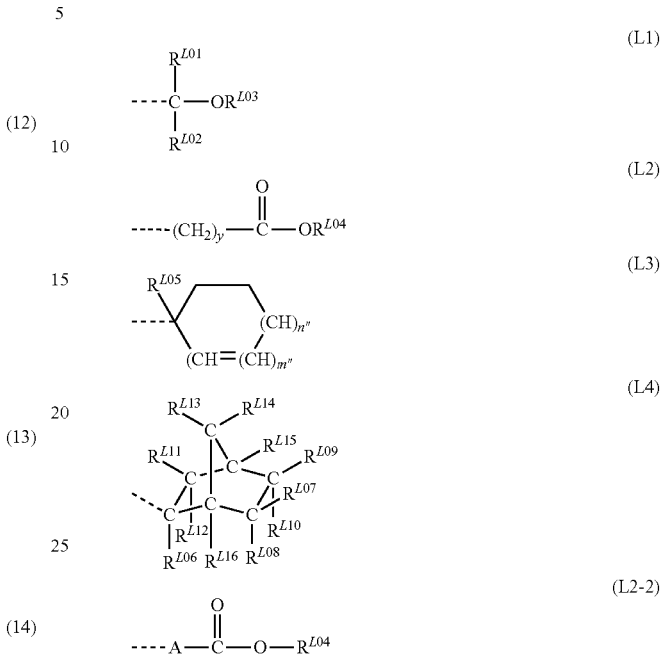

Here, the broken lines denote bond (hereinafter same as this).

In addition, in the formula (L1), $R^{L01}$ and $R^{L02}$ represent a hydrogen atom, or a linear, a branched, or a cyclic alkyl group having 1 to 18 preferably 1 to 10 carbon atoms, specifically such as methyl group, an ethyl group, propyl group, isopropyl group, n-butyl group, sec-butyl group, tert-butyl group, cyclopentyl group, cyclohexyl group, 2-ethylhexyl group, n-octyl group, norbornyl group, tricyclodecanyl group, tetracyclododecanyl group, adamantyl group. $R^{L03}$ represents a monovalent hydrocarbon group having 1 to 18 preferably 1 to 10 carbon atoms, optionally containing a hetero atom such as oxygen. A linear, a branched, or a cyclic alkyl group, and a compound in which part of hydrogen atoms thereof is substituted by hydroxyl group, an alkoxy group, an oxo group, an amino group, an alkylamino group, etc. are given, and specifically, following substituted alkyl groups are exemplified.

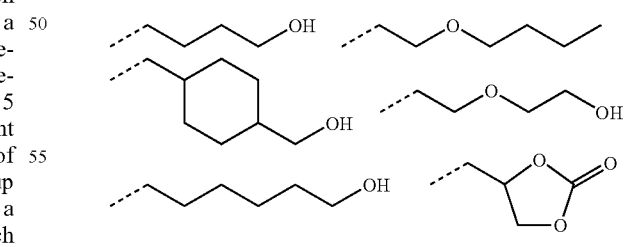

$R^{L01}$ and $R^{L02}$, $R^{L01}$ and $R^{L03}$ and $R^{L02}$ and $R^{L03}$ may be bonded with each other to form a ring together with a carbon atom or oxygen atom to which they are bonded. When they form a ring, each $R^{L01}$, $R^{L02}$ and $R^{L03}$ represent a linear or a branched alkylene group having 1 to 18 preferably 1 to 10 carbon atoms.

In the formula (L2), $R^{L04}$ represents tertiary alkyl group having 4 to 20 preferably 4 to 15 carbon atoms, a trialkylsilyl group whose each alkyl group has 1 to 6 carbon atoms, an oxoalkyl group having 4 to 20 carbon atoms, or the group represented by the general formula (L1). As the tertiary alkyl group, specifically, tert-butyl group, tert-amyl group, 1,1-diethyl propyl group, 2-cyclopentylpropane-2-yl group, 2-cyclohexylpropane-2-yl group, 2-(bicyclo[2.2.1]heptane-2-yl)propane-2-yl group, 2-(adamantane-1-yl)propane-2-yl group, 1-ethylcyclopentyl group, 1-butylcyclopentyl group, 1-ethylcyclohexyl group, 1-butylcyclohexyl group, 1-ethyl-2-cyclopentenyl group, 1-ethyl-2-cyclohexenyl group, 2-methyl-2-adamantyl group, 2-ethyl-2-adamantyl group, etc. are exemplified. As the trialkylsilyl group, specifically, trimethylsilyl group, triethylsilyl group, dimethyl-tert-butylsilyl group, etc. are exemplified. As an oxoalkyl group, specifically, 3-oxocyclohexyl group, 4-methyl-2-oxooxane-4-yl group, 5-methyl-2-oxooxolane-5-yl group, etc. are exemplified. "y" represents an integer of 0 to 6.

In the formula (L2-2),

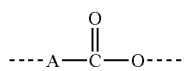

is the following groups, and RL04 represents the same as before.

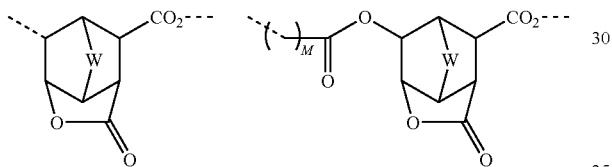

(In the formula, the broken lines denote bond. W represents an oxygen atom or $CH_2$, M represents an integer of 1 to 3.)

In the formula (L3), $R^{L05}$ represents a linear, a branched, or a cyclic alkyl group having 1 to 8 carbon atoms, optionally substituted, or an aryl group having 6 to 20 carbon atoms, optionally substituted. As the optionally substituted alkyl group, specifically, a linear, branched or cyclic alkyl group such as methyl group, ethyl group, propyl group, isopropyl group, n-butyl group, sec-butyl group, tert-butyl group, tert-amyl group, n-pentyl group, n-hexyl group, cyclopentyl group, and cyclohexyl group, and a compound in which part of hydrogen atoms thereof is substituted by hydroxyl group, an alkoxy group, a carboxyl group, alkoxycarbonyl group, oxo group, amino group, an alkylamino group, a cyano group, mercapto group, alkylthio group, sulfo group, etc. are exemplified. As the optionally substituted aryl group, specifically, phenyl group, methylphenyl group, naphthyl group, anthryl group, phenanthryl group, pyrenyl group, etc. are exemplified. "m"" represents 0 or 1, "n"" is any of 0, 1, 2 or 3, which satisfy 2m"+n"=2 or 3.

In the formula (L4), Each $R^{L06}$ represents a linear, a branched, or a cyclic alkyl group having 1 to 8 carbon atoms, optionally substituted, or aryl group having 6 to 20 carbon atoms, optionally substituted, specifically the same as $R^{L05}$, etc. Each $R^{L07}$ to $R^{L16}$ independently represents hydrogen atom or a monovalent hydrocarbon group having 1 to 15 carbon atoms, specifically, a linear, branche or cyclic alkyl group such as methyl group, ethyl group, propyl group, isopropyl group, n-butyl group, sec-butyl group, tert-butyl group, tert-amyl group, n-pentyl group, n-hexyl group, n-octyl group, n-nonyl group, n-decyl group, cyclopentyl group, cyclohexyl group, cyclopentylmethyl group, cyclopentylethyl group, cyclopentylbutyl group, cyclohexylmethyl group, cyclohexylethyl group, and cyclohexylbutyl group, and a compound in which part of hydrogen atoms thereof is substituted by hydroxyl group, an alkoxy group, a carboxyl group, an alkoxycarbonyl group, oxo group, amino group, alkylamino group, cyano group, mercapto group, alkylthio group, sulfo group, etc. Each two of $R^{L07}$ to $R^{L16}$ may be bonded with each other to form a ring together with a carbon atom (for example, $R^{L07}$ and $R^{L08}$, $R^{L07}$ and $R^{L09}$, $R^{L08}$ and $R^{L10}$, $R^{L09}$ and $R^{L10}$, $R^{L11}$ and $R^{L12}$, $R^{L13}$ and $R^{L14}$, etc.) In this case, a thing which is related to the combination represents a divalent hydrocarbon group having 1 to 15 carbon atoms, specifically, a thing whose one hydrogen atom is removed from the examples of a monovalent hydrocarbon group etc. In addition, each two of $R^{L07}$ to $R^{L16}$ which are located adjacently may be bonded without anything and form a double bond (for example, $R^{L07}$ and $R^{L09}$, $R^{L09}$ and $R^{L15}$, $R^{L13}$ and $R^{L15}$, etc.).

As linear or branched one among the acid-labile group shown by the formula (L1), specifically following groups are exemplified.

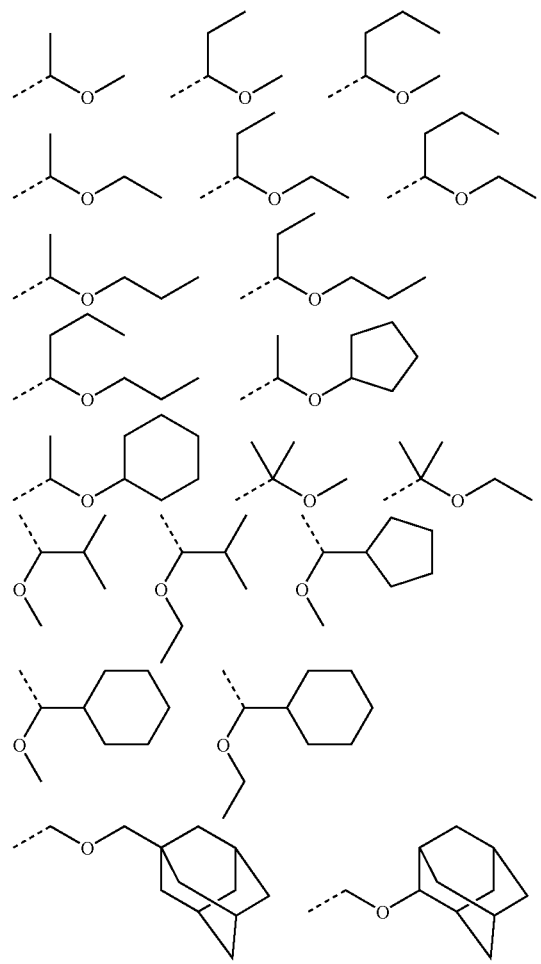

As cyclic one among the acid-labile group shown by the formula (L1), specifically tetrahydrofuran-2-yl group, 2-methyl tetrahydrofuran-2-yl group, tetrahydropyran-2-yl group, 2-methyltetrahydropyran-2-yl group, etc. are exemplified.

As the acid-labile group of the formula (L2), specifically tert-butoxycarbonyl group, tert-butoxycarbonylmethyl group, tert-amyloxycarbonyl group, tert-amyloxycarbonylmethyl group, 1,1-diethylpropyloxycarbonyl group, 1,1-diethylpropyloxycarbonylmethyl group, 1-ethylcyclopentyloxycarbonyl group, 1-ethylcyclopentyloxycarbonylmethyl group, 1-ethyl-2-cyclopentenyloxycarbonyl group, 1-ethyl-2-cyclopentenyloxycarbonylmethyl group, 1-ethoxyethoxycarbonylmethyl group, 2-tetrahydropyranyloxycarbonylmethyl group, 2-tetrahydrofuranyloxycarbonylmethyl group, etc. are exemplified.

As acid-labile group of the formula (L2-2), specifically 9-(tert-butyloxycarbonyl)-5-oxo-4-oxatricyclo[4.2.1.0$^{3,7}$]nonane-2-yl group, 9-(tert-amyloxycarbonyl)-5-oxo-4-oxatricyclo[4.2.1.0$^{3,7}$]nonane-2-yl group, 9-(2-(adamantane-1-yl)propane-2-yloxycarbonyl)-5-oxo-4-oxatricyclo[4.2.1.0$^{3,7}$]nonane-2-yl group, 9-(1-ethylcyclopentyloxycarbonyl)-5-oxo-4-oxatricyclo[4.2.1.0$^{3,7}$]nonane-2-yl group, 9-(1-butylcyclopentyloxycarbonyl)-5-oxo-4-oxatricyclo[4.2.1.0$^{3,7}$]nonane-2-yl group, 9-(1-ethylcyclohexyloxycarbonyl)-5-oxo-4-oxatricyclo[4.2.1.0$^{3,7}$]nonane-2-yl group, 9-(1-butylcyclohexyloxycarbonyl)-5-oxo-4-oxatricyclo[4.2.1.0$^{3,7}$]nonane-2-yl group, 9-(2-methyl-2-adamantyloxycarbonyl)-5-oxo-4-oxatricyclo[4.2.1.0$^{3,7}$]nonane-2-yl group, 9-(2-ethyl-2-adamantyloxycarbonyl)-5-oxo-4-oxatricyclo[4.2.1.0$^{3,7}$]nonane-2-yl group, 9-(4-ethyltetracyclo[6.2.1.1$^{3,6}$.0$^{2,7}$]dodecane-4-yloxycarbonyl)-5-oxo-4-oxatricyclo[4.2.1.0$^{3,7}$]nonane-2-yl group, 2-(9-(tert-butyloxycarbonyl)-5-oxo-4-oxatricyclo[4.2.1.0$^{3,7}$]nonane-2-yloxy)-2-oxoethyl group, 2-(9-(tert-amyloxycarbonyl)-5-oxo-4-oxatricyclo[4.2.1.0$^{3,7}$]nonane-2-yloxy)-2-oxoethyl group, 2-(9-(2-(adamantane-1-yl)propane-2-yloxycarbonyl)-5-oxo-4-oxatricyclo[4.2.1.0$^{3,7}$]nonane-2-yloxy)-2-oxoethyl group, 2-(9-(1-ethylcyclopentyloxycarbonyl)-5-oxo-4-oxatricyclo[4.2.1.0$^{3,7}$]nonane-2-yloxy)-2-oxoethyl group, 2-(9-(1-butylcyclopentyloxycarbonyl)-5-oxo-4-oxatricyclo[4.2.1.0$^{3,7}$]nonane-2-yloxy)-2-oxoethyl group, 2-(9-(1-ethylcyclohexyloxycarbonyl)-5-oxo-4-oxatricyclo[4.2.1.0$^{3,7}$]nonane-2-yloxy)-2-oxoethyl group, 2-(9-(1-butylcyclohexyloxycarbonyl)-5-oxo-4-oxatricyclo[4.2.1.0$^{3,7}$]nonane-2-yloxy)-2-oxoethyl group, 2-(9-(2-methyl-2-adamantyloxycarbonyl)-5-oxo-4-oxatricyclo[4.2.1.0$^{3,7}$]nonane-2-yloxy)-2-oxoethyl group, 2-(9-(2-ethyl-2-adamantyloxycarbonyl)-5-oxo-4-oxatricyclo[4.2.1.0$^{3,7}$]nonane-2-yloxy)-2-oxoethyl group, 2-(9-(4-ethyltetracyclo[6.2.1.1$^{3,6}$.0$^{2,7}$]dodecane-4-yloxycarbonyl)-5-oxo-4-oxatricyclo[4.2.1.0$^{3,7}$]nonane-2-yloxy)-2-oxoethyl group, 4-(9-(tert-butyloxycarbonyl)-5-oxo-4-oxatricyclo[4.2.1.0$^{3,7}$]nonane-2-yloxy)-4-oxobutyl group, 4-(9-(tert-amyloxycarbonyl)-5-oxo-4-oxatricyclo[4.2.1.0$^{3,7}$]nonane-2-yloxy)-4-oxobutyl group, 4-(9-(2-(adamantane-1-yl)propane-2-yloxycarbonyl)-5-oxo-4-oxatricyclo[4.2.1.0$^{3,7}$]nonane-2-yloxy)-4-oxobutyl group, 4-(9-(1-ethylcyclopentyloxycarbonyl)-5-oxo-4-oxatricyclo[4.2.1.0$^{3,7}$]nonane-2-yloxy)-4-oxobutyl group, 4-(9-(1-butylcyclopentyloxycarbonyl)-5-oxo-4-oxatricyclo[4.2.1.0$^{3,7}$]nonane-2-yloxy)-4-oxobutyl group, 4-(9-(1-ethylcyclohexyloxycarbonyl)-5-oxo-4-oxatricyclo[4.2.1.0$^{3,7}$]nonane-2-yloxy)-4-oxobutyl group, 4-(9-(1-butylcyclohexyloxycarbonyl)-5-oxo-4-oxatricyclo[4.2.1.0$^{3,7}$]nonane-2-yloxy)-4-oxobutyl group, 4-(9-(2-methyl-2-adamantyloxycarbonyl)-5-oxo-4-oxatricyclo[4.2.1.0$^{3,7}$]nonane-2-yloxy)-4-oxobutyl group, 4-(9-(2-ethyl-2-adamantyloxycarbonyl)-5-oxo-4-oxatricyclo[4.2.1.0$^{3,7}$]nonane-2-yloxy)-4-oxobutyl group, 4-(9-(4-ethyltetracyclo[6.2.1.1$^{3,6}$.0$^{2,7}$]dodecane-4-yloxycarbonyl)-5-oxo-4-oxatricyclo[4.2.1.0$^{3,7}$]nonane-2-yloxy)-4-oxobutyl group, etc. are exemplified.

As acid-labile group of the formula (L3), specifically 1-methylcyclopentyl, 1-ethylcyclopentyl, 1-n-propylcyclopentyl, 1-isopropylcyclopentyl, 1-n-butylcyclopentyl, 1-sec-butylcyclopentyl, 1-cyclohexylcyclopentyl, 1-(4-methoxy-n-butyl)cyclopentyl, 1-methylcyclohexyl, 1-ethylcyclohexyl, 3-methyl-1-cyclopentene-3-yl, 3-ethyl-1-cyclopentene-3-yl, 3-methyl-1-cyclohexene-3-yl, 3-ethyl-1-cyclohexene-3-yl, etc. are exemplified.

As acid-labile group of the formula (L4), groups shown in the following formulae (L4-1) to (L4-4) are particularly preferable.

(L4-1)

(L4-2)

(L4-3)

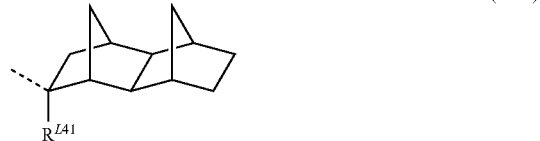

(L4-4)

In the formulae (L4-1) to (L4-4), the broken lines denote bond and combination direction. Each $R^{L41}$ independently represents a linear, a branched, or a cyclic alkyl group having 1 to 8 carbon atoms, optionally substituted, or aryl group having 6 to 20 carbon atoms, optionally substituted, specifically the same as $R^{L05}$ etc. can be exemplified.

There are possibilities a presence of an enantiomer and a diastereomer in the general formulae (L4-1) to (L4-4). The general formulae (L4-1) to (L4-4) represent all of these stereoisomers. These stereoisomers may be used singly or as a mixture of them.

For example, the general formula (L4-3) is intended to represent one or a mixture of two selected from the groups represented by the following general formulae (L4-3-1) and (L4-3-2).

(L4-3-1)

-continued (L4-3-2)

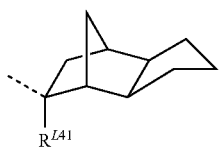

(In the formulae, $R^{L41}$ represents the same as before.)

In addition, the formula (L4-4) is intended to represents one, or two or more selected from groups represented the following general formulae (L4-4-1) to (L4-4-4).

(L-4-4-1)

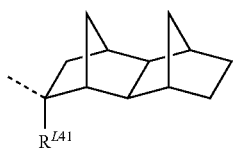

(L4-4-2)

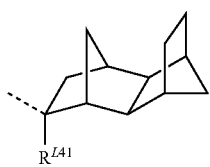

(L4-4-3)

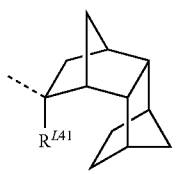

(L-4-4-4)

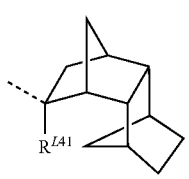

(In the formulae, $R^{L41}$ represents the same as before.)

The general formulae (L4-1) to (L4-4), (L4-3-1), (L4-3-2), and (L4-4-1) to (L4-4-4) are intended to also represent all of these stereoisomers and a mixture of the stereoisomers.

Meanwhile, a high reactivity in the acid-catalyzed elimination reaction is realized when each of the bonding directions of (L4-1) to (L4-4), (L4-3-1), (L4-3-2), and (L4-4-1) to (L4-4-4) is to the exo-position of the bicyclo[2.2.1]heptane ring (refer to Japanese Patent Application Laid-Open No. 2000-336121). In the preparation of a monomer containing a tertiary exo-alkyl group having these bicyclo[2.2.1]hepatane skeletons as the substituent group, there is a case to include a monomer that is substituted with an endo-alkyl group represented by the following general formulae (L4-1-endo) to (L4-4-endo). In such a case, to accomplish a good reactivity the exo-ratio is preferably 50% or more by mol, or more preferably 80% or more by mol.

(L4-1-endo)

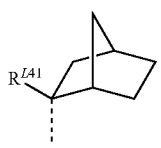

(L4-2-endo)

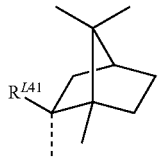

(L4-3-endo)

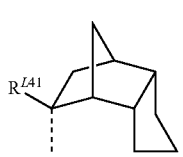

(L4-4-endo)

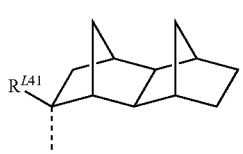

(In the formulae, $R^{L41}$ represents the same as before.)

As acid-labile group of the formula (L4), specifically the following groups are exemplified.

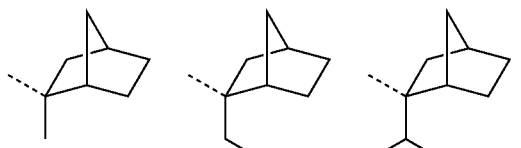

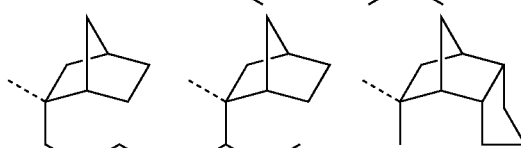

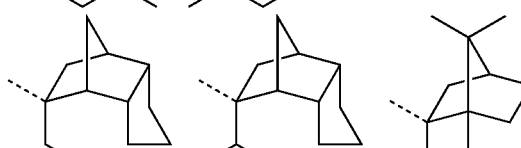

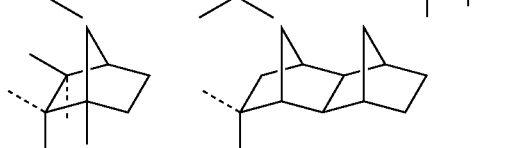

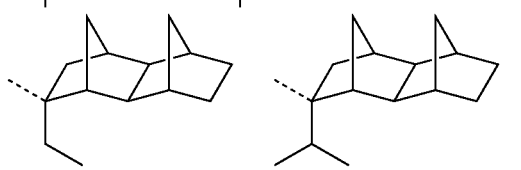

In addition, as a tertiary alkyl group having 4 to 20 carbon atoms, a trialkylsilyl group whose each alkyl group has 1 to 6 carbon atoms, and an oxoalkyl group having 4 to 20 carbon atoms, specifically the same as $R^{L05}$ etc. are exemplified.

Specifically, the repeating unit represented by the general formula (11) can be exemplified by the followings, but is not limited to them. Although only a (meth)acrylate ester is shown, the one intervened by a divalent connector represented by the formula (L-2) or (L-2-2) may also be used.
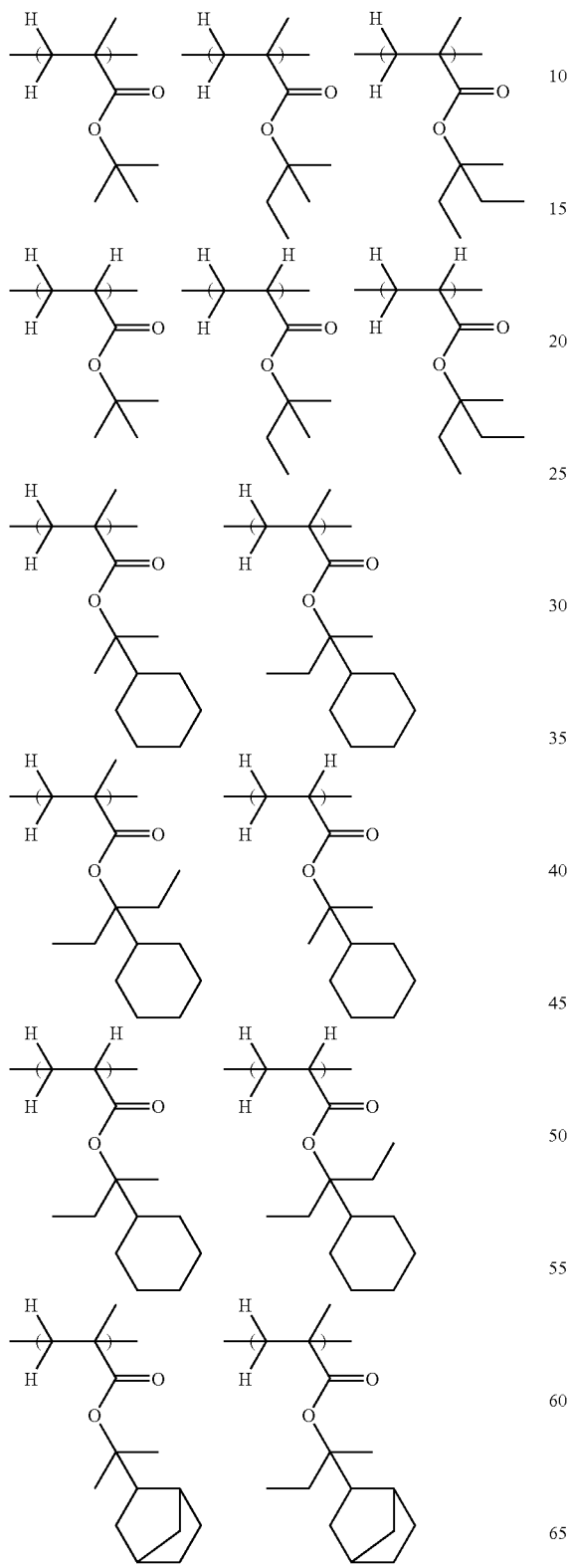
-continued
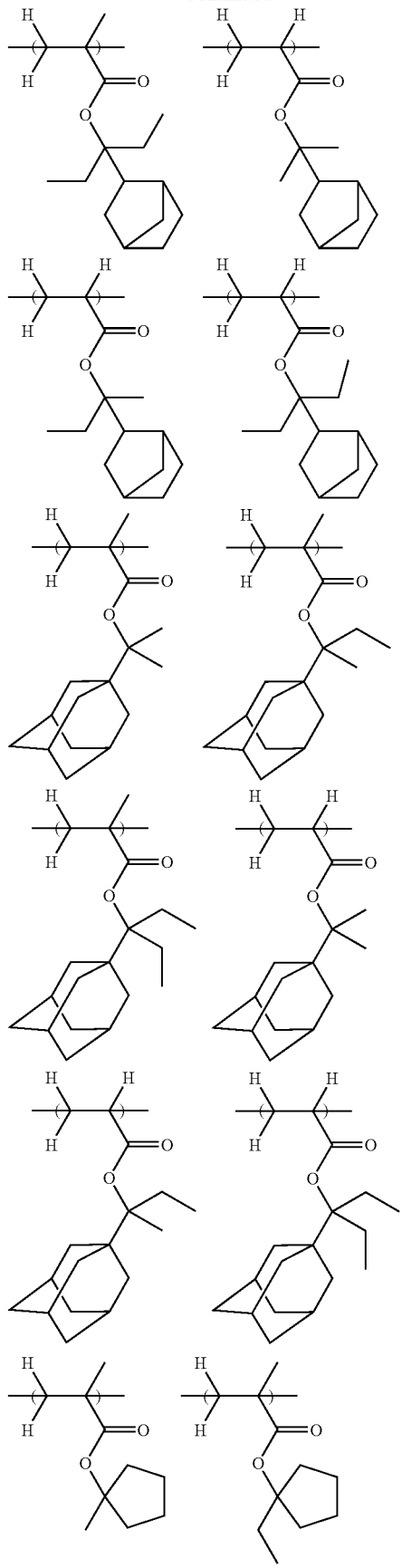

-continued
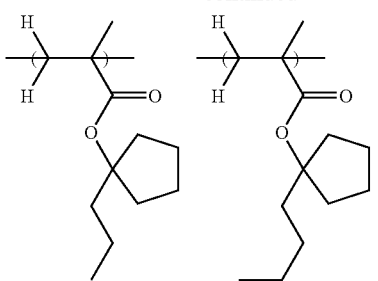
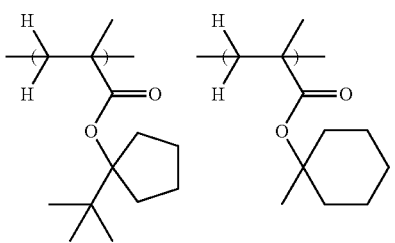
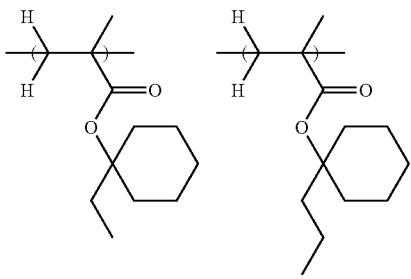
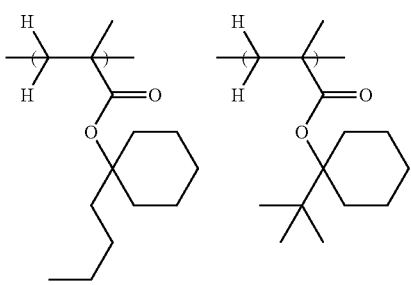
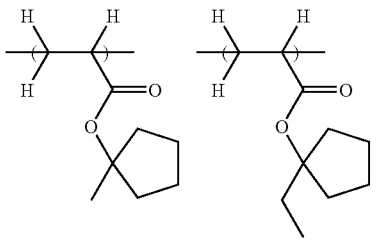
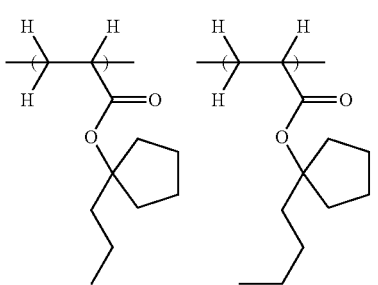
-continued
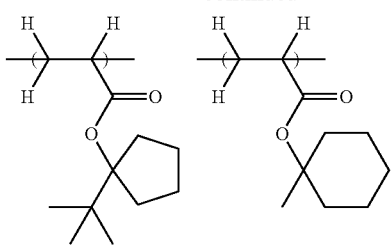
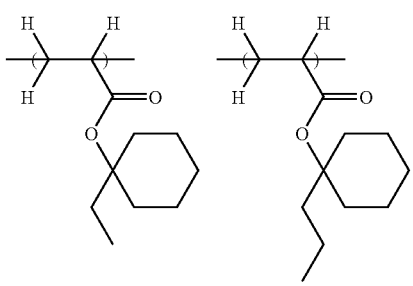
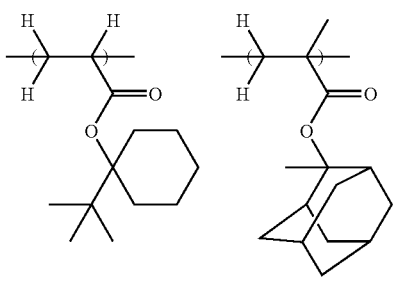
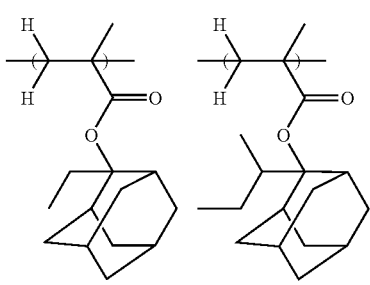
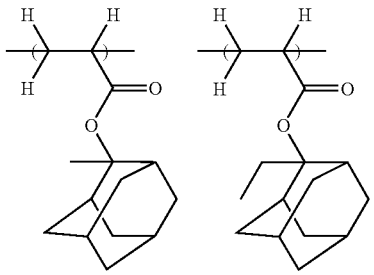
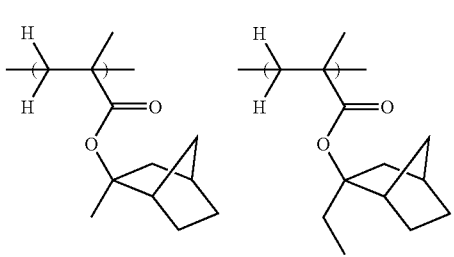

-continued
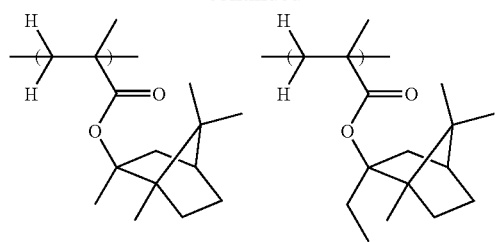
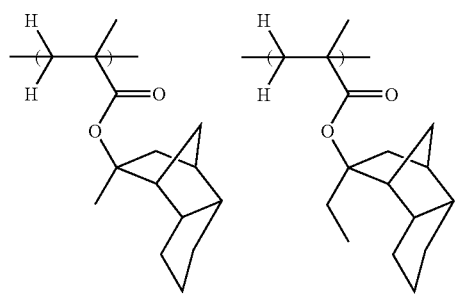
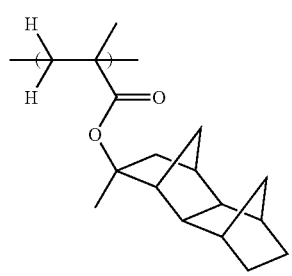
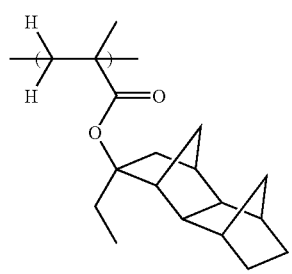
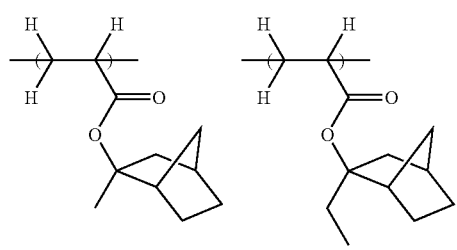
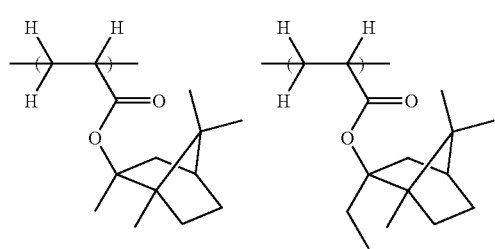
-continued
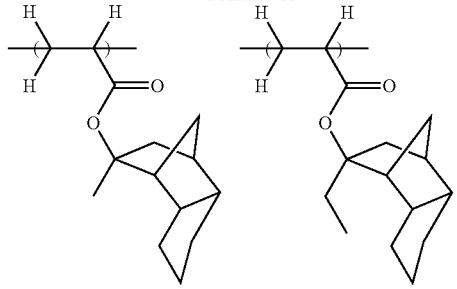
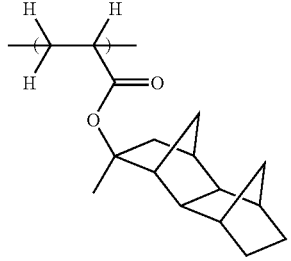
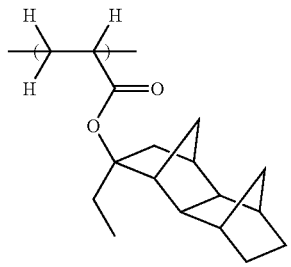
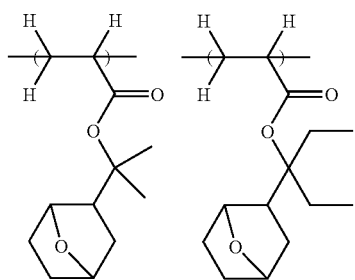
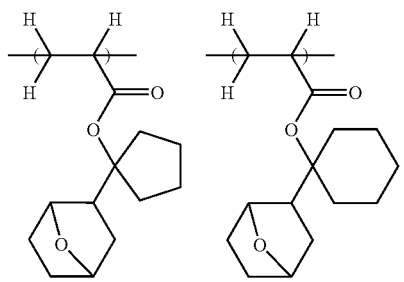
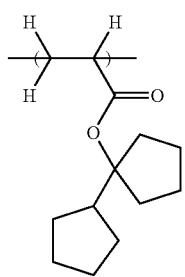

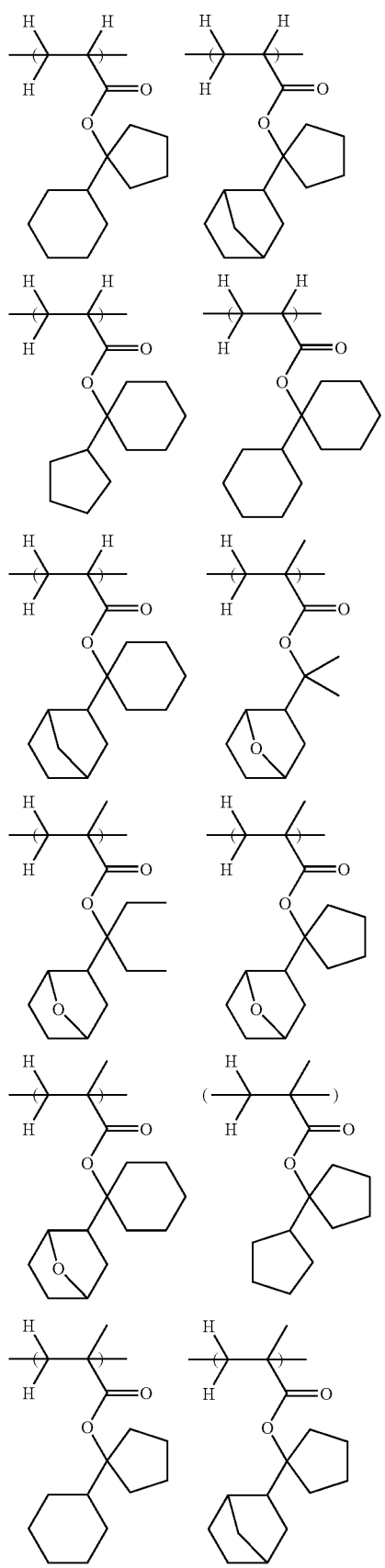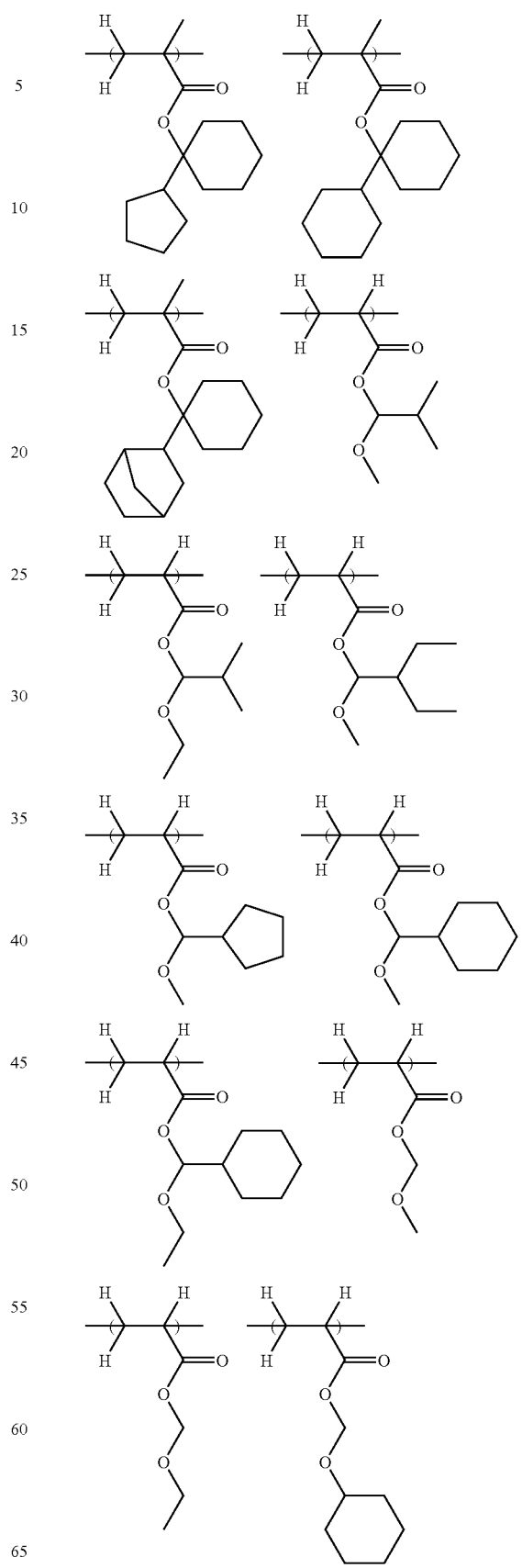

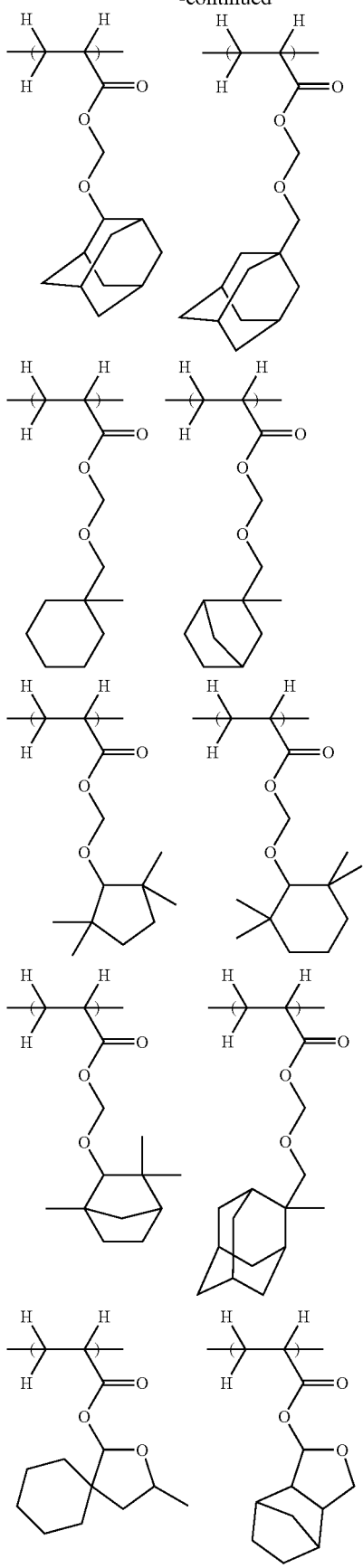
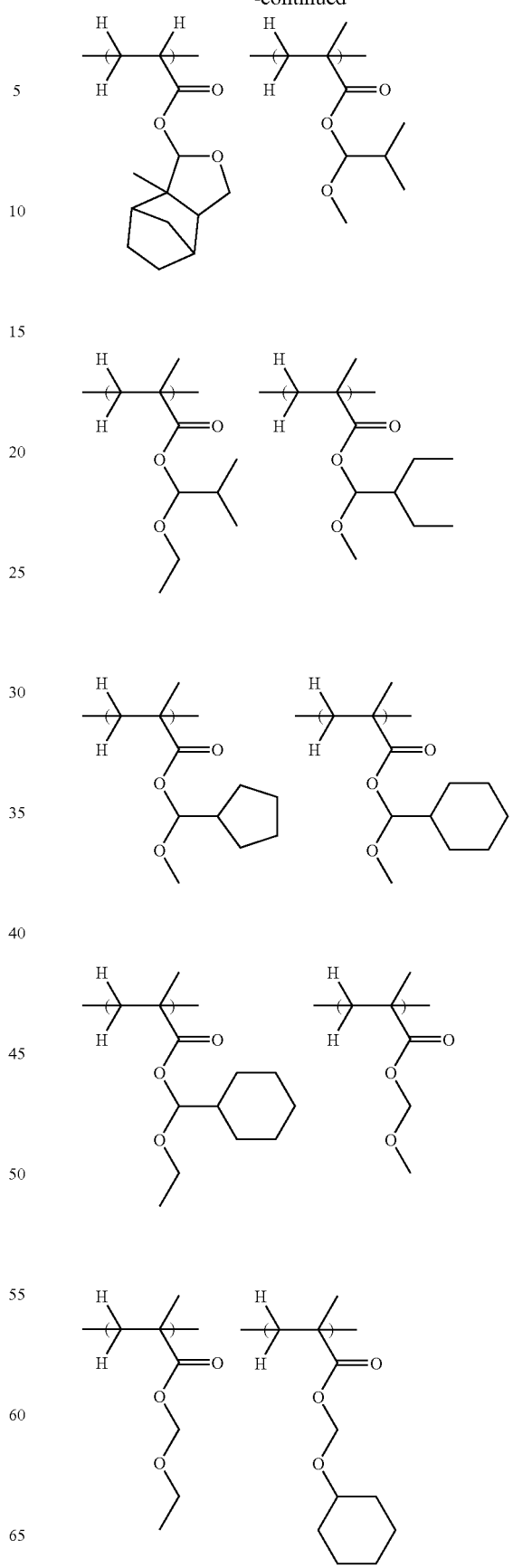

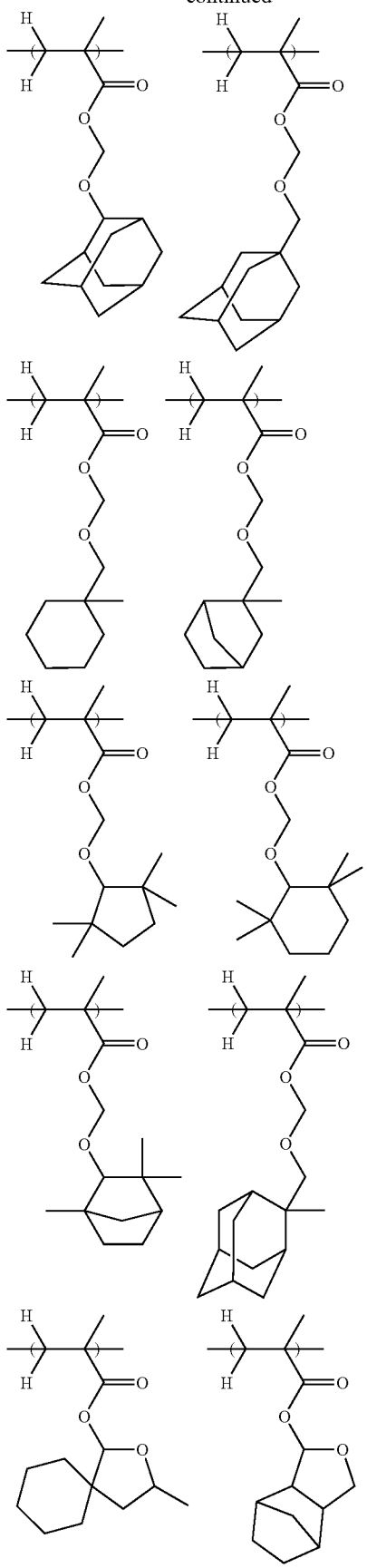

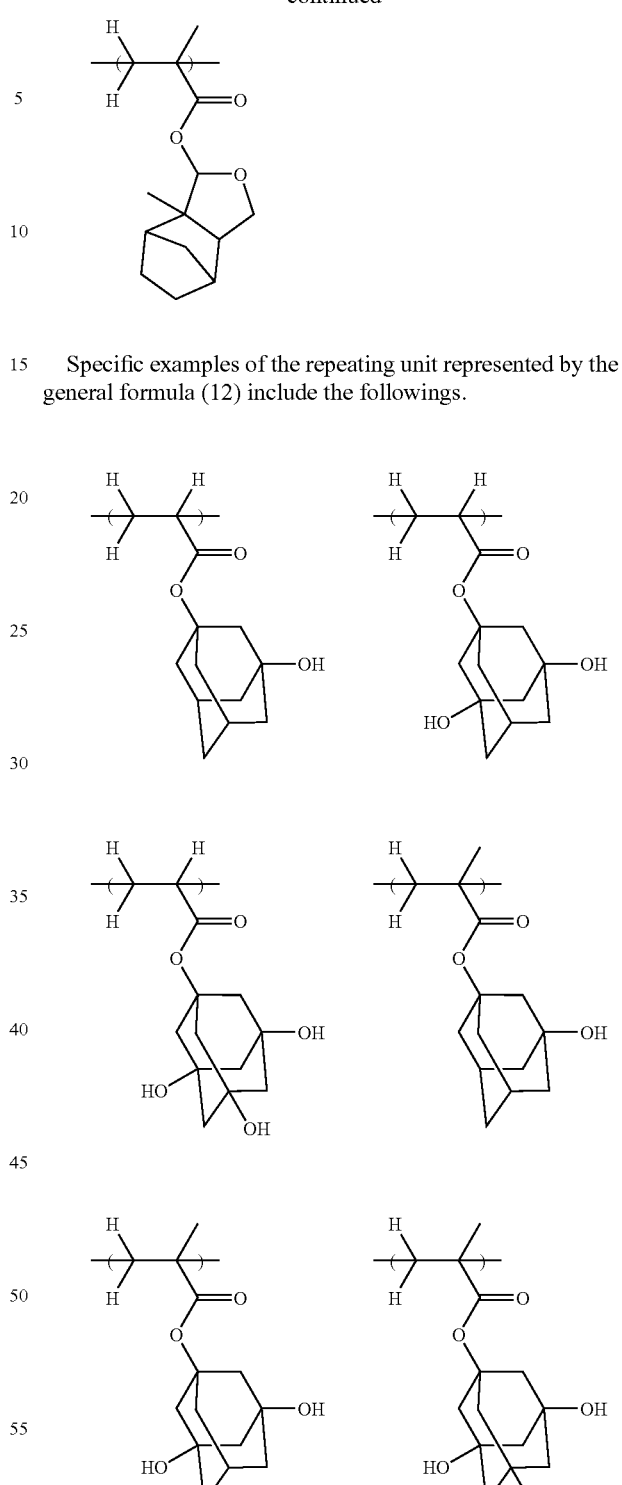

Specific examples of the repeating unit represented by the general formula (12) include the followings.

Specific examples of the repeating unit represented by the general formula (13) include the followings. Meanwhile, there also exists the repeating unit containing the acid-labile group. Specifically, they are overlapped with the general formula (L2-2), which was described as the acid-labile group, but they may be used as the lactone units and as the units containing the acid-labile group as well.

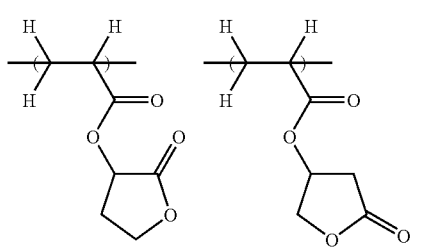
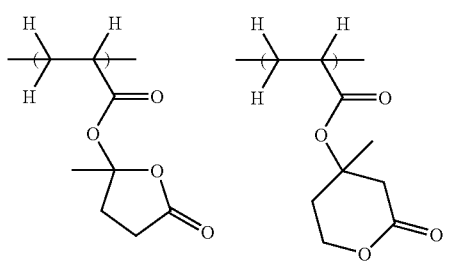
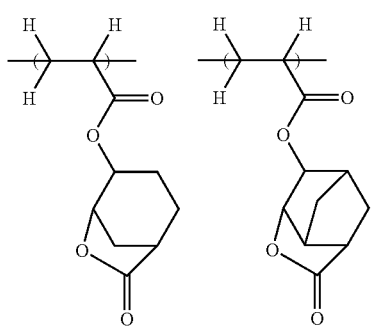
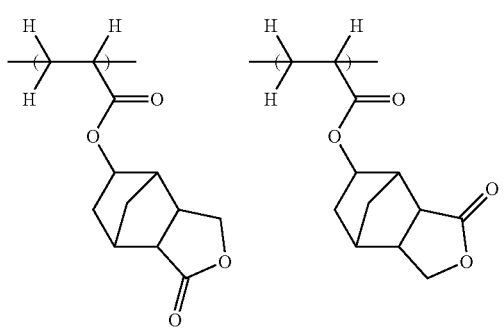
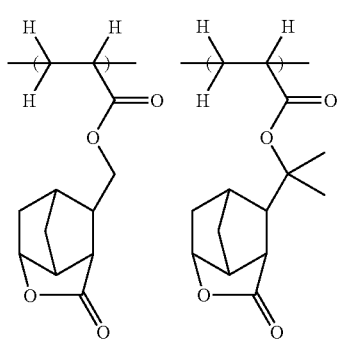
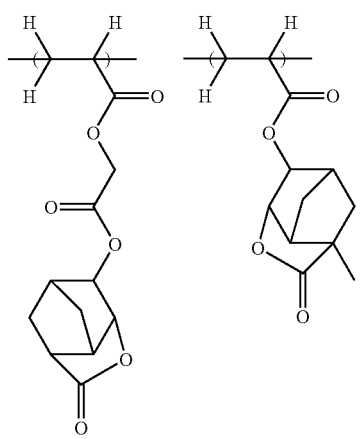
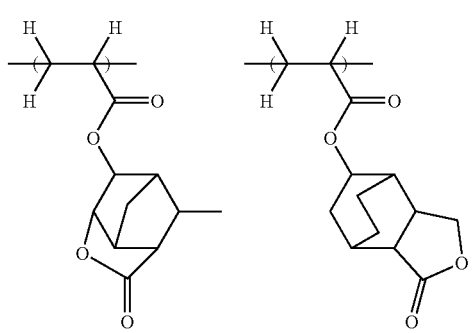
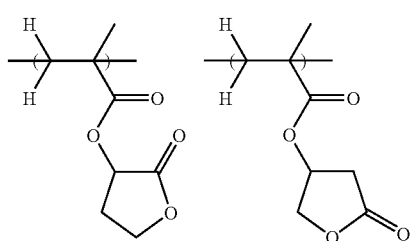
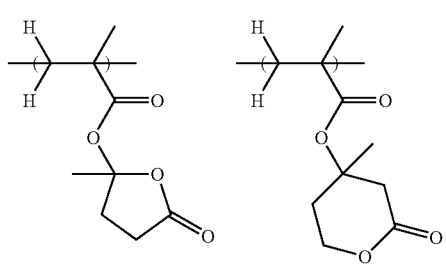
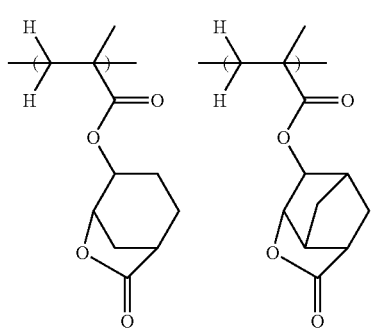

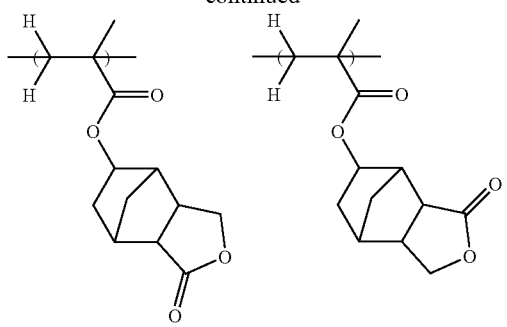
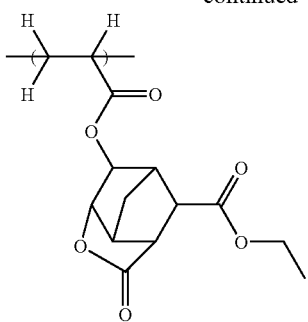
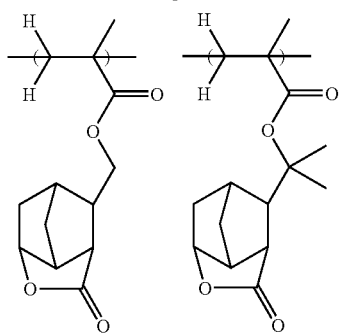
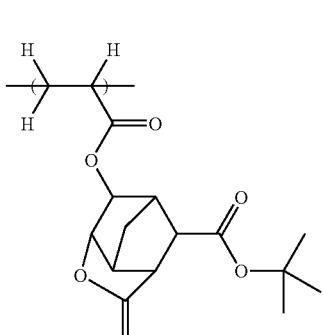
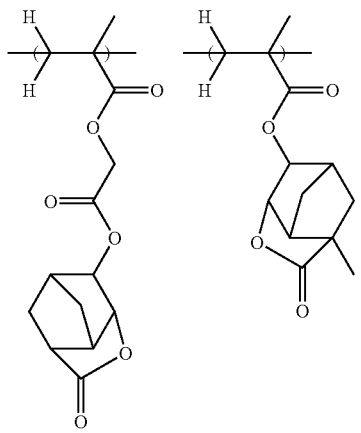
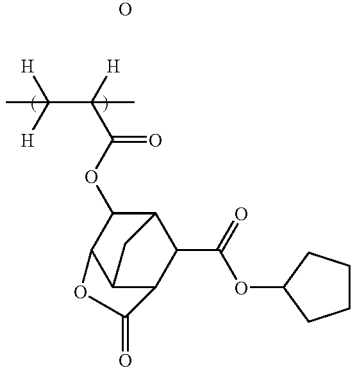
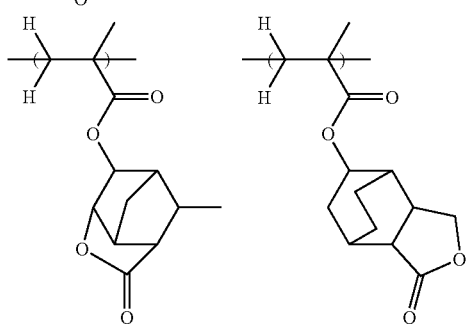
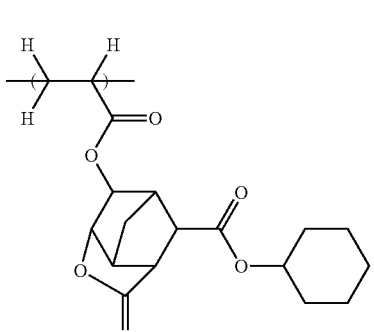
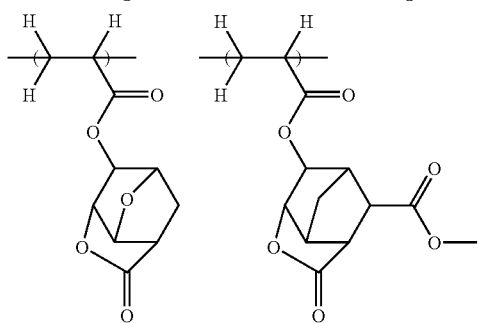
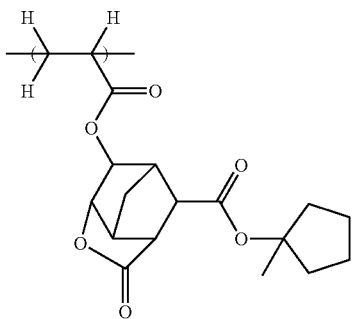

-continued
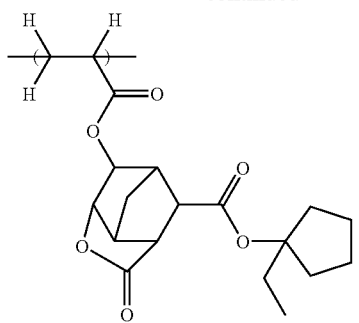
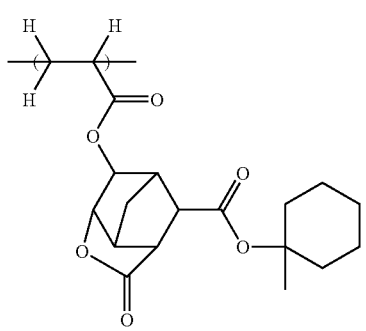
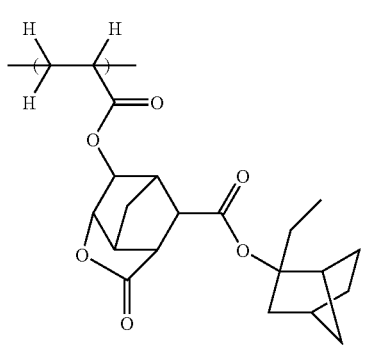
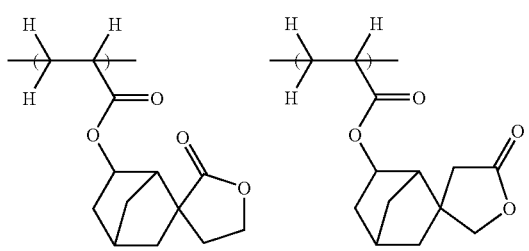
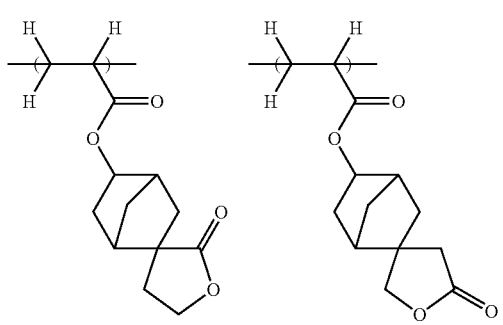
-continued
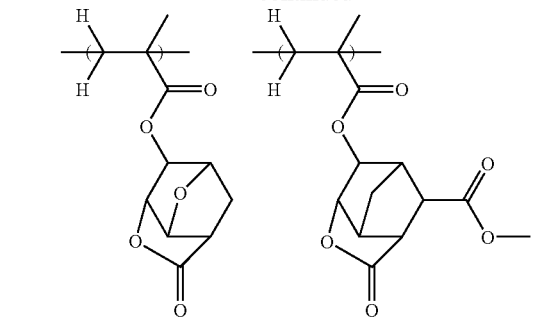
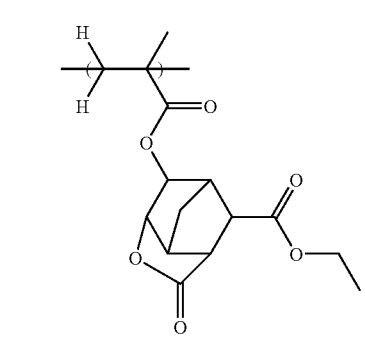
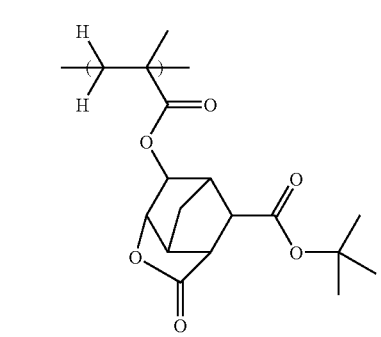
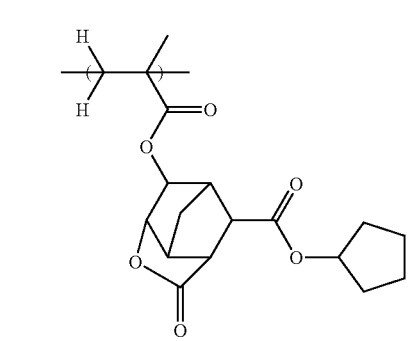
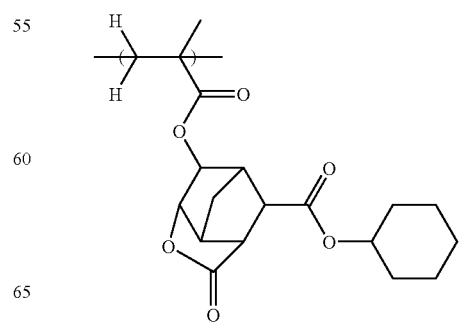

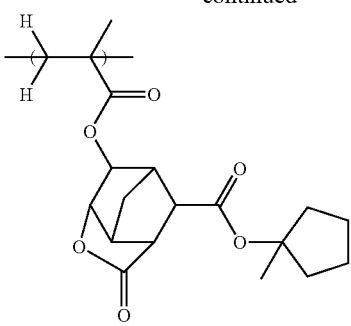
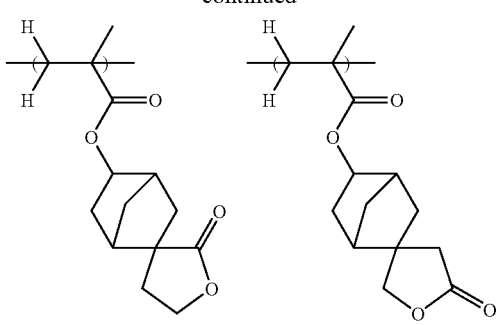

In addition, a thing shown by the following general formula (5L-1) can also be used preferably.

(5L-1)

Here, $R^{111}$ in the general formula (5L-1) represents hydrogen atom, fluorine atom, methyl group or trifluoromethyl group. More preferably it is methyl group.

$R^{5'}$ represents hydrogen atom or $CO_2 R^{5''}$. $R^{5''}$ represents a linear, a branched, or a cyclic monovalent hydrocarbon group having 1 to 15, optionally containing hydrogen atom, halogen atom or oxygen atom. W' represents $CH_2$, O, or S.

M' represents an integer of 1 to 3.

As $R^{5''}$, specifically hydrogen atom, methyl group, ethyl group, n-propyl group, isopropyl group, n-butyl group, sec-butyl group, isobutyl group, tert-butyl group, cyclopentyl group, a cyclohexyl group, 1-methylcyclopentyl group, 1-ethylcyclopentyl group, 1-methylcyclohexyl group, 1-ethylcyclohexyl group, 2-ethylhexyl group, n-octyl group, 2-methylbicyclo[2.2.1]heptane-2-yl group, 2-ethylbicyclo[2.2.1]heptane-2-yl group, 2-methyladamantane-2-yl group, 2-ethyladamantane-2-yl group, 8-methyltricyclo[5.2.1.0$^{2,6}$]decane-8-yl group, 8-ethyltricyclo[5.2.1.0$^{2,6}$]decane-8-yl group, 4-methyltetracyclo[6.2.1.1$^{3,6}$.0$^{2,7}$]dodecane-4-yl group, 4-ethyltetracyclo[6.2.1.1$^{3,6}$.0$^{2,7}$]dodecane-4-yl group, methoxymethyl group, ethoxymethyl group, methoxyethyl group, ethoxyethyl group, methoxyethoxyethyl group, the following groups, etc. are exemplified.

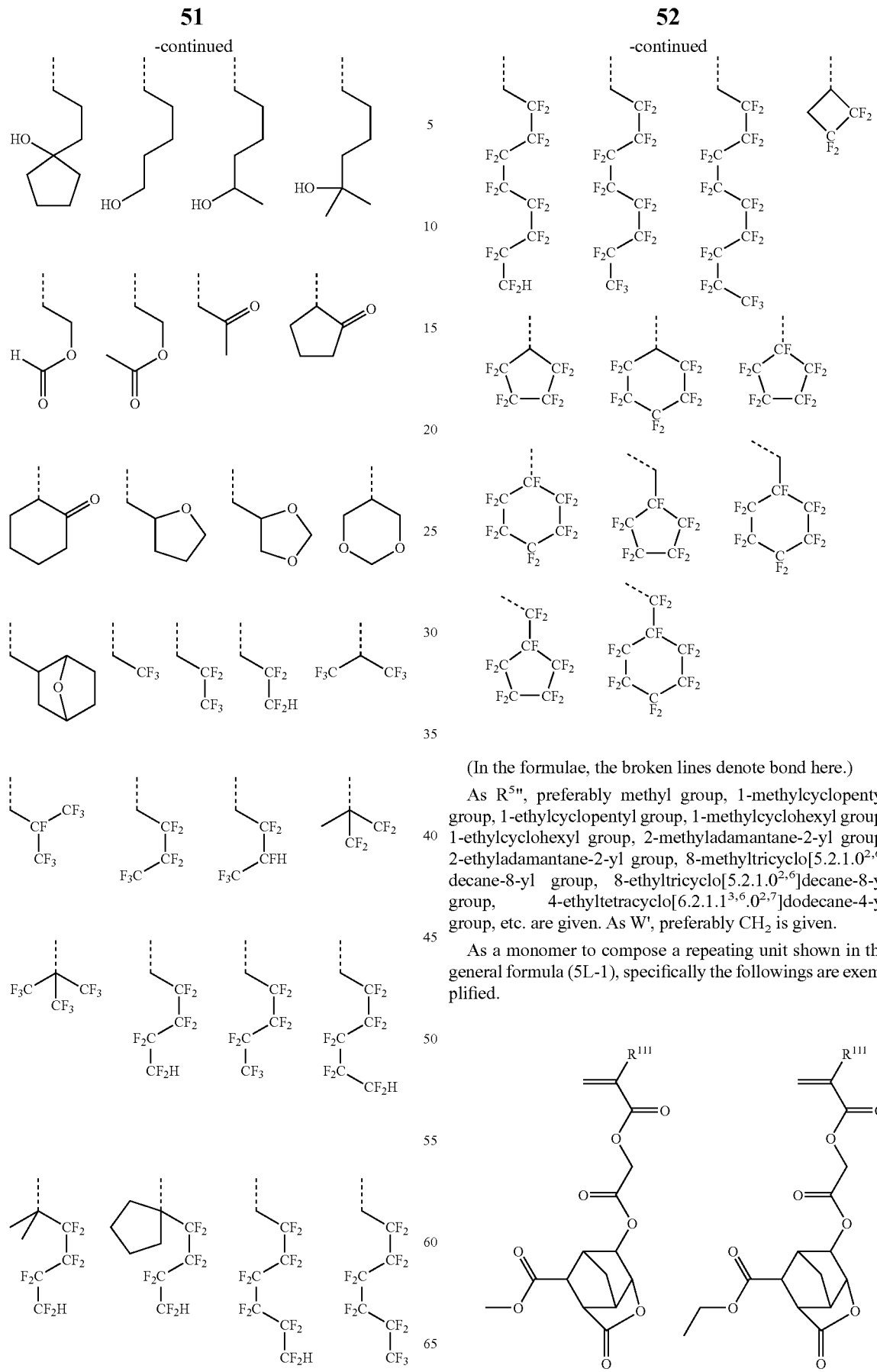

(In the formulae, the broken lines denote bond here.)

As $R^{5''}$, preferably methyl group, 1-methylcyclopentyl group, 1-ethylcyclopentyl group, 1-methylcyclohexyl group, 1-ethylcyclohexyl group, 2-methyladamantane-2-yl group, 2-ethyladamantane-2-yl group, 8-methyltricyclo[5.2.1.0$^{2,6}$] decane-8-yl group, 8-ethyltricyclo[5.2.1.0$^{2,6}$]decane-8-yl group, 4-ethyltetracyclo[6.2.1.1$^{3,6}$.0$^{2,7}$]dodecane-4-yl group, etc. are given. As W', preferably $CH_2$ is given.

As a monomer to compose a repeating unit shown in the general formula (5L-1), specifically the followings are exemplified.

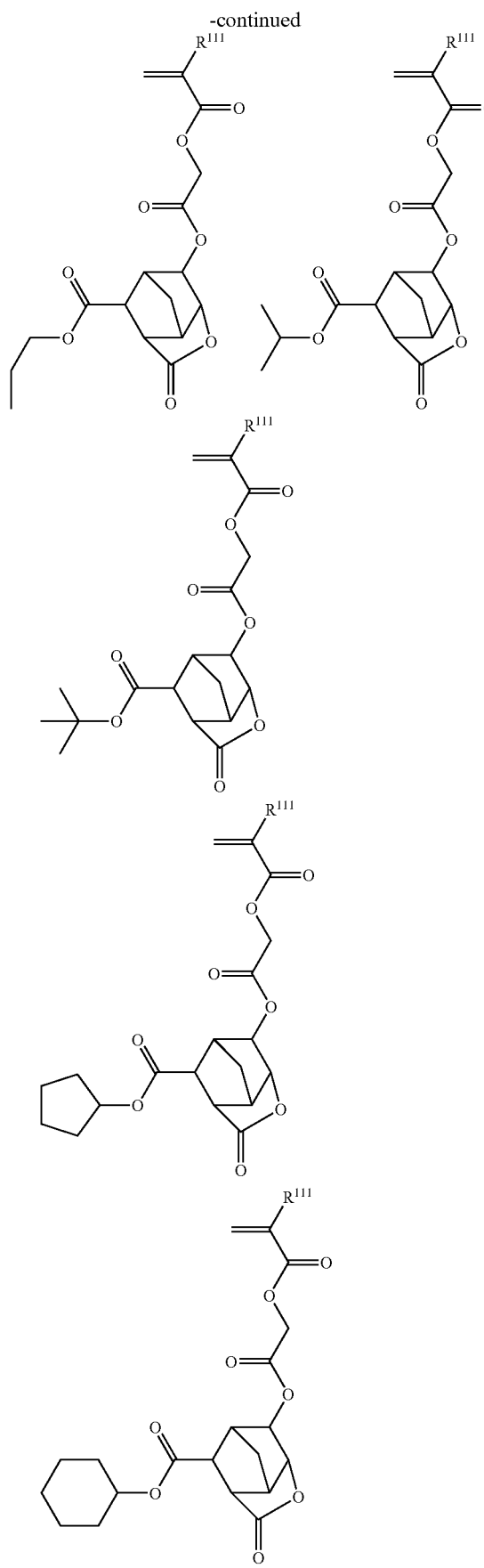
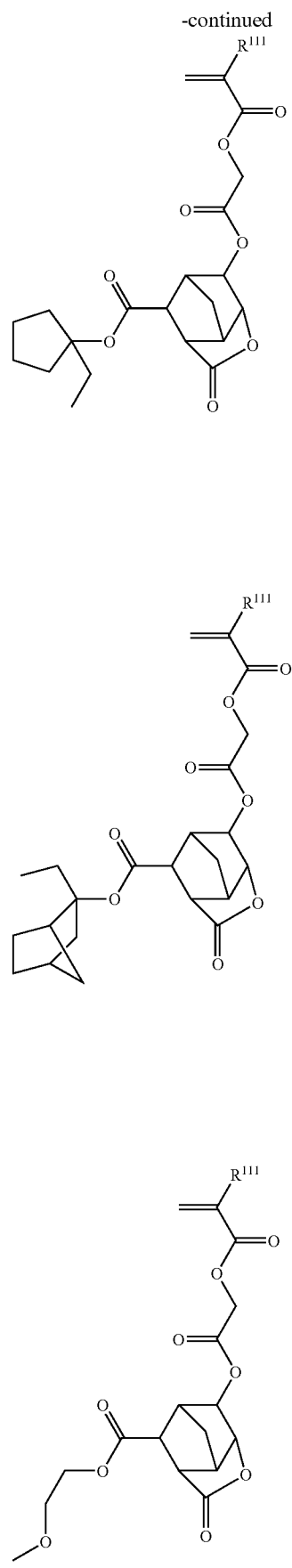

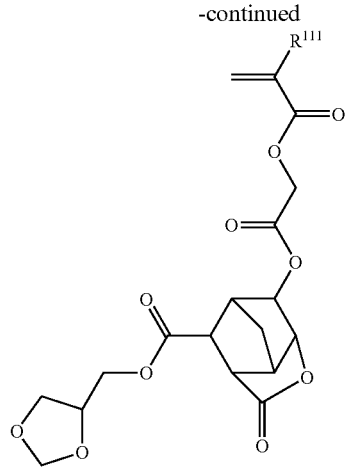
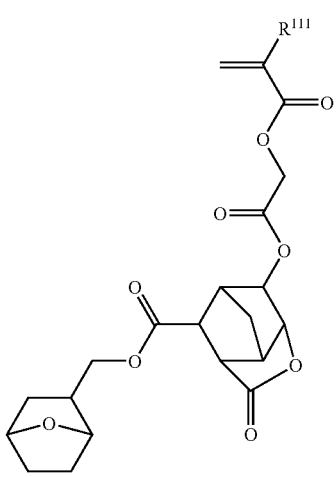
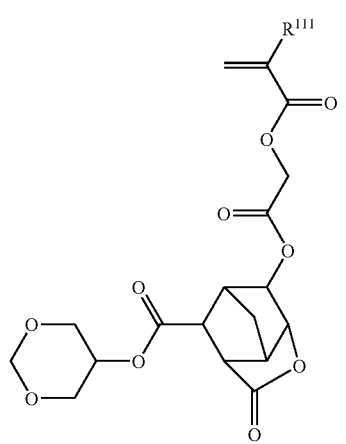
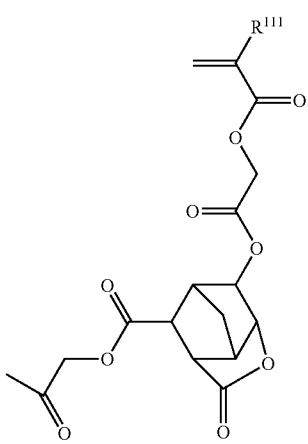
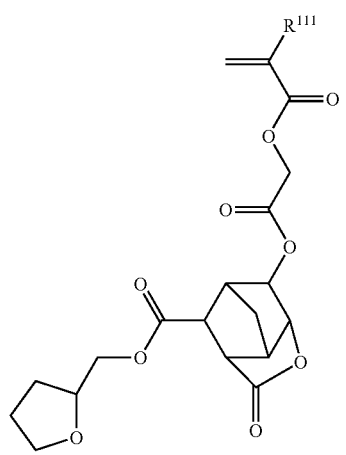
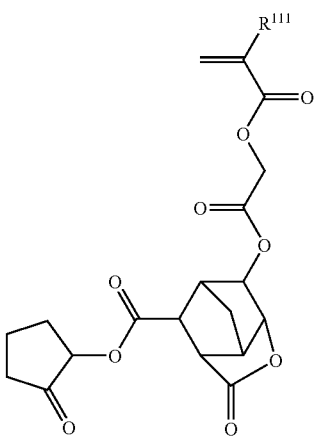
(In the formulae, R$^{111}$ represents the same as before.)

57
-continued
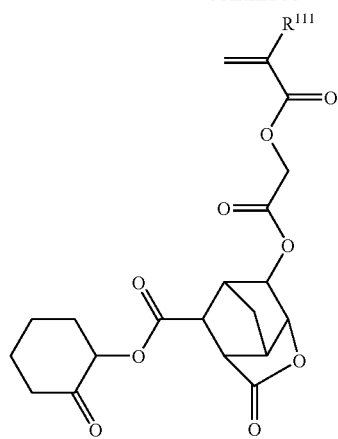
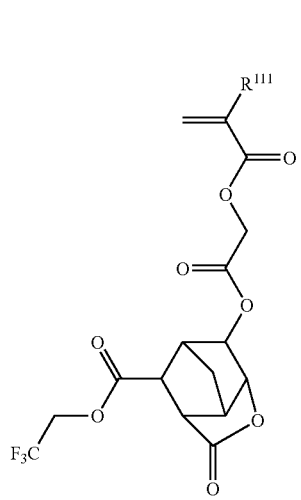
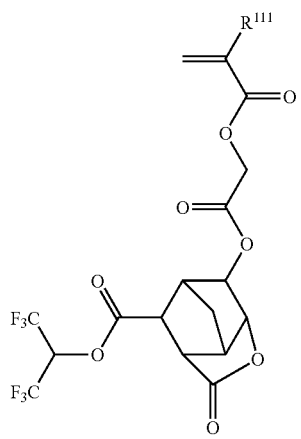
58
-continued
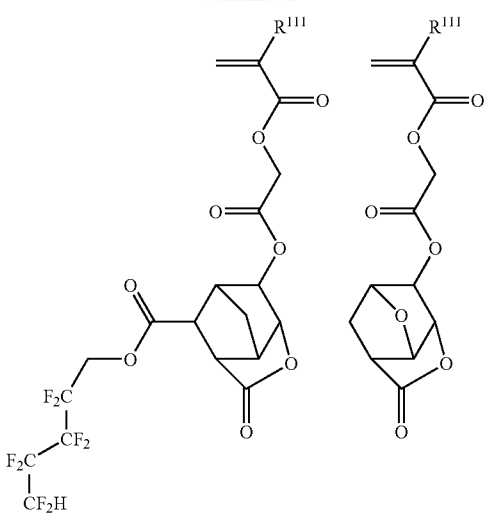
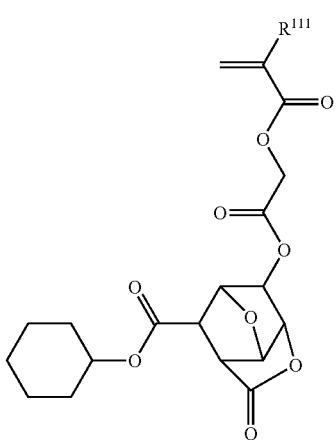

-continued
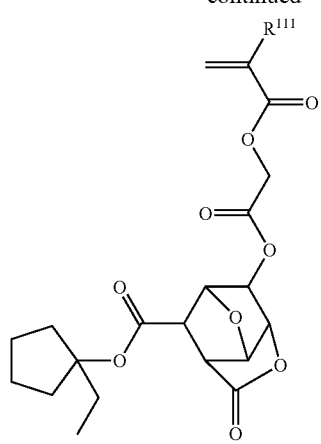
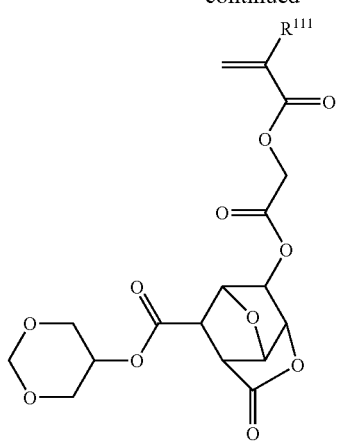
(In the formulae, R$^{111}$ represents the same as before.)
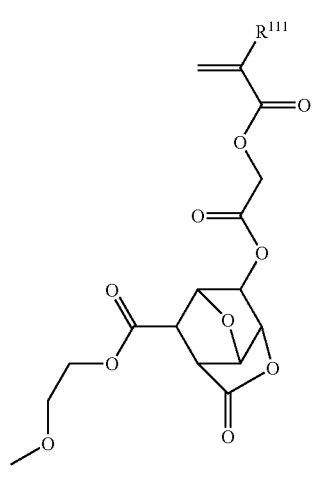
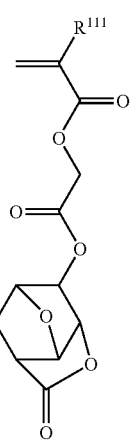
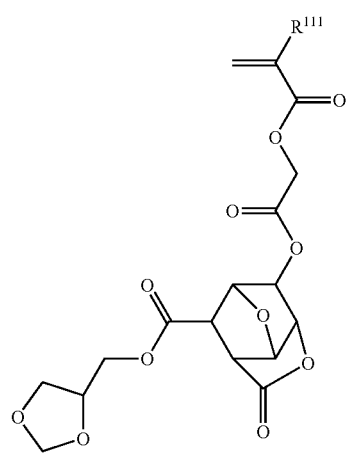
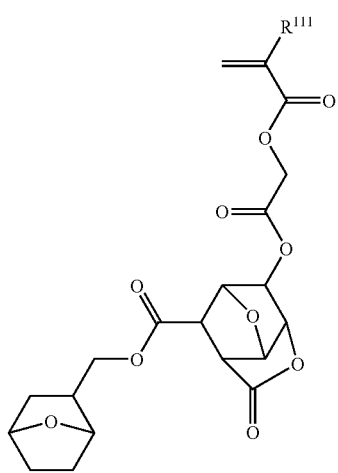

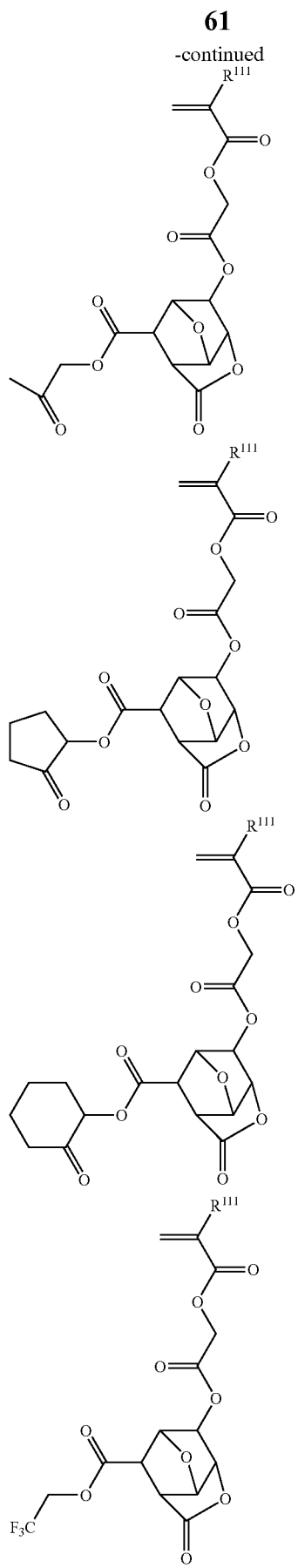

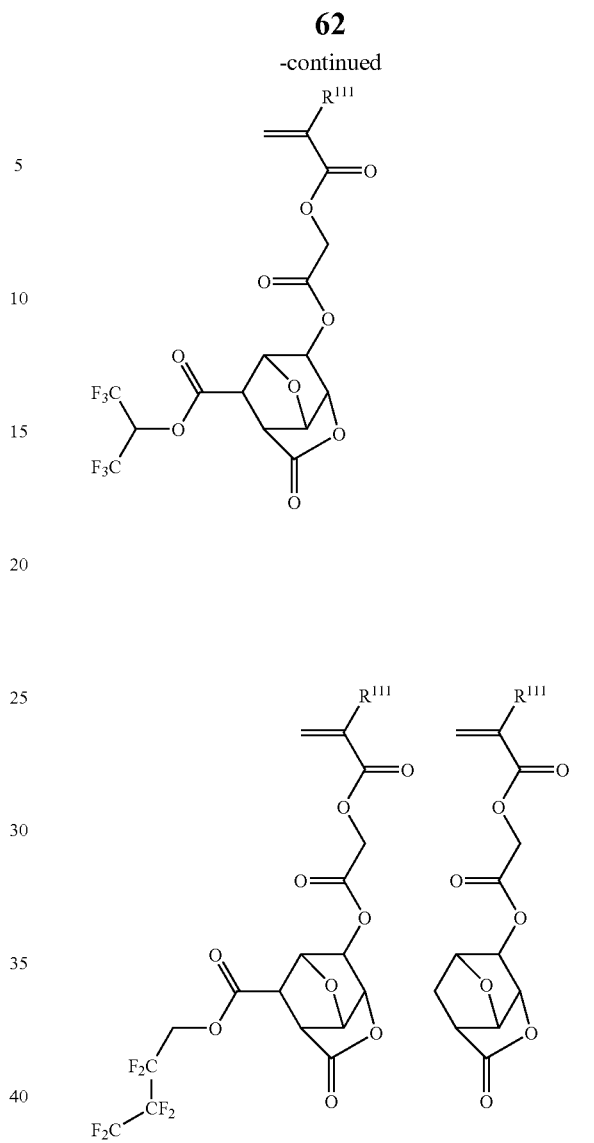

(In the formula, $R^{111}$ represents the same as before.)

Among the monomers to compose the repeating unit represented by the general formula (5L-1), details of the compound with M'=1 are described in Japanese Patent Application Laid-Open No. 2008-031298. The compound with M'=3 can be synthesized in a similar manner by changing the raw material chloroacetyl chloride in the compound with M'=1 to chlorobutyryl chloride.

Specific examples of the repeating unit represented by the general formula (14) include the followings.

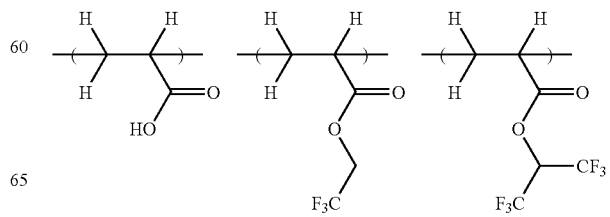

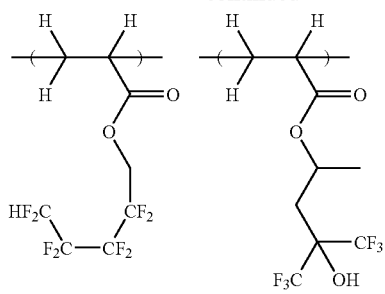
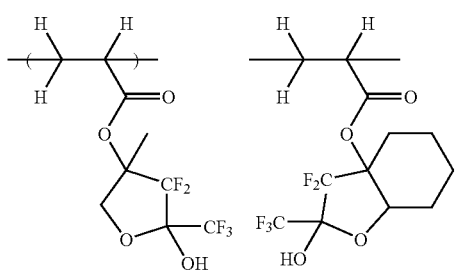
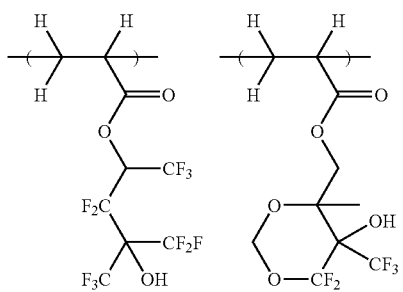
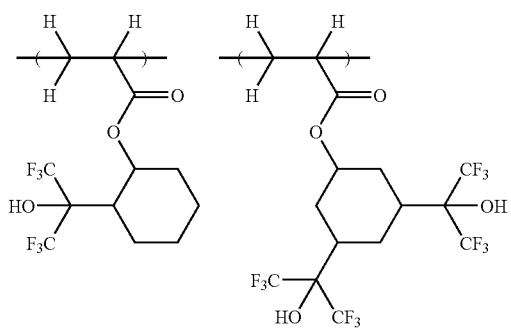
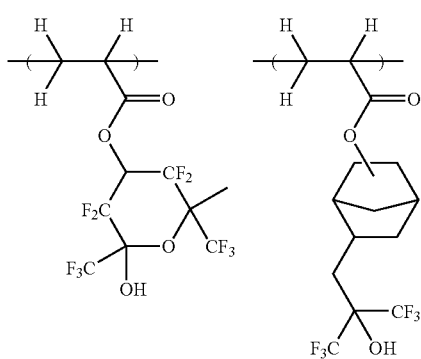
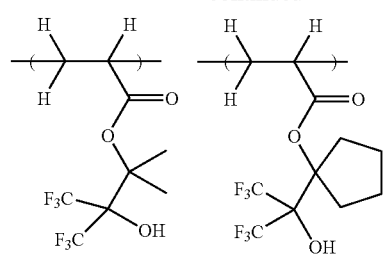
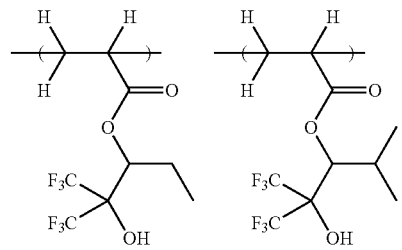
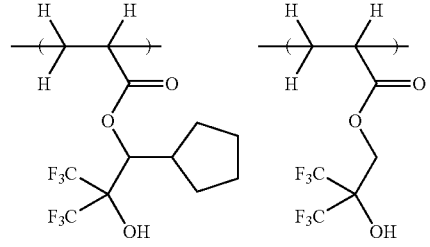
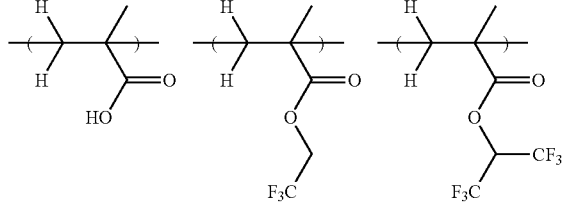
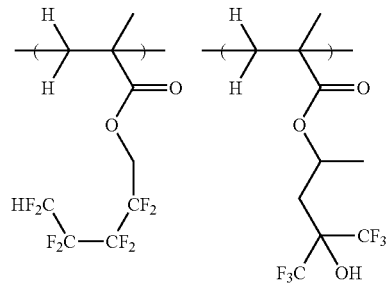
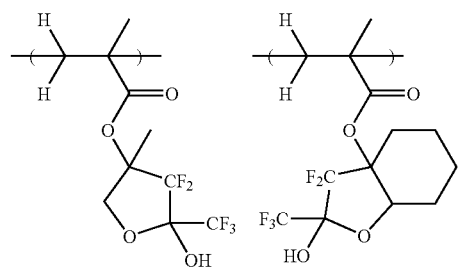

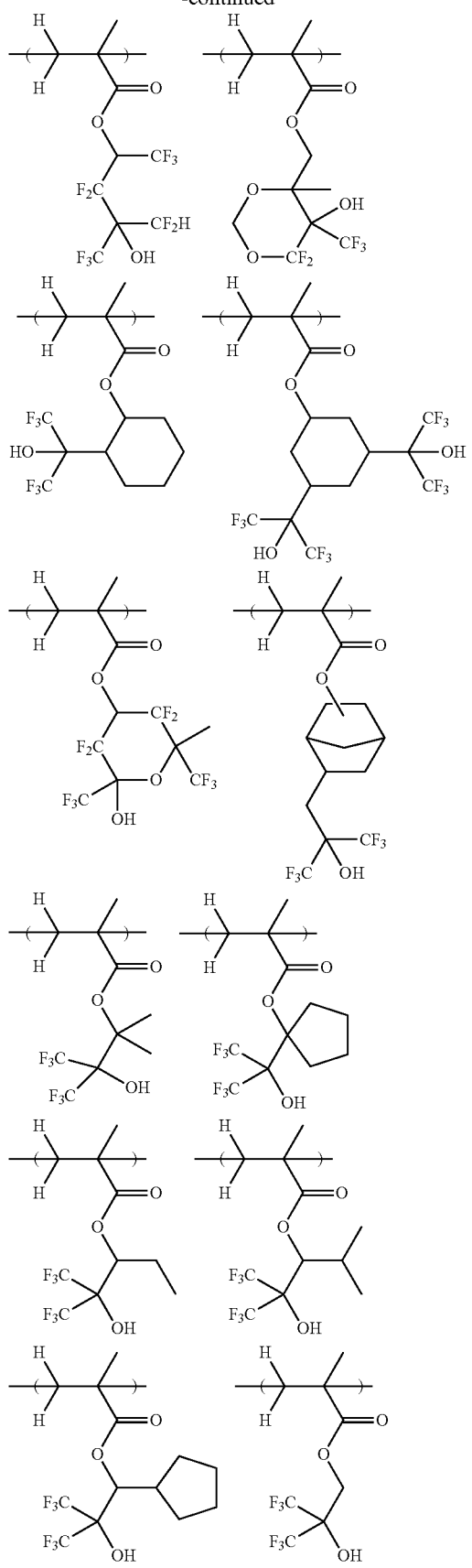
Specific examples of the repeating unit represented by the general formula (15) include the followings.
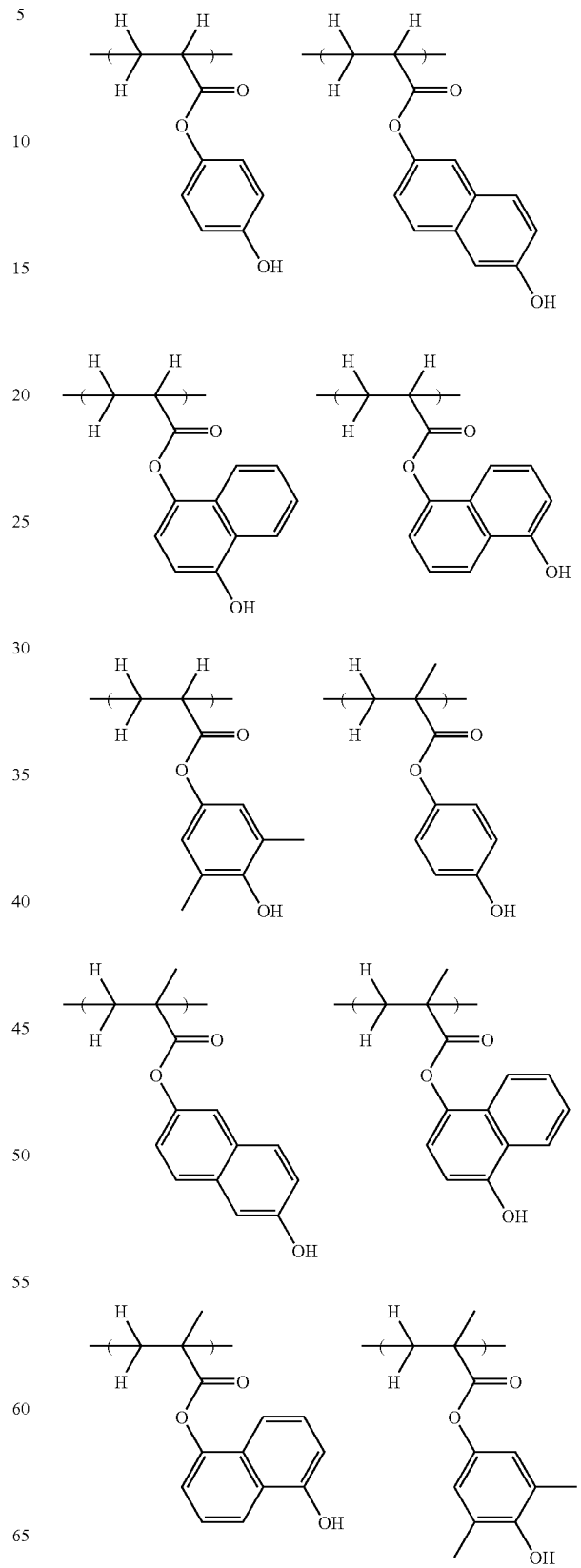

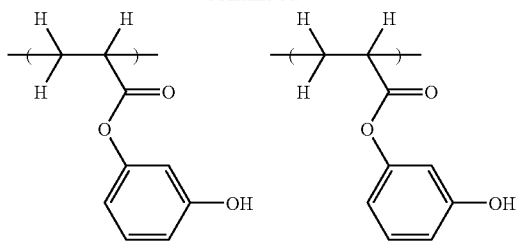
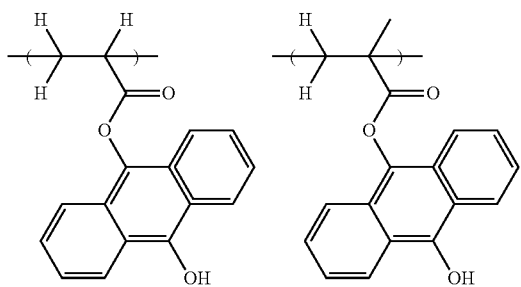
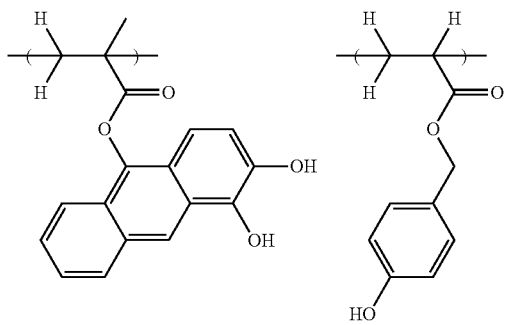
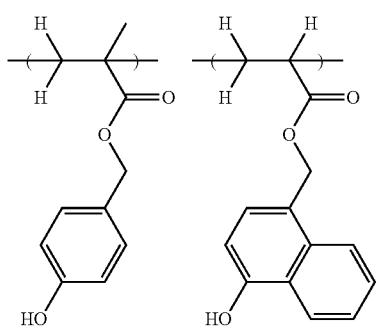
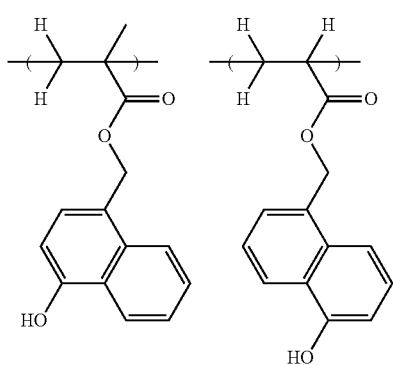

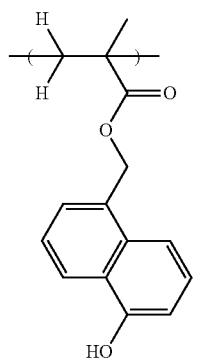

The polymer used as a base resin of the resist composition of the present invention may contain a repeating unit derived from a monomer having a C—C double bond other than those described above. For example, it may contain a repeating unit derived from substituted acrylate esters such as methyl methacrylate, methyl crotonate, dimethyl maleate, and diemethyl itaconate; unsaturated carboxylic acids such as maleic acid, fumaric acid, and itaconic acid; cyclic olefins such as norbornene, a norbornene derivative, and a tetracyclo[6.2.1.1$^{3,6}$.0$^{2,7}$]dodecene derivative; unsaturated acid anhydrides such as itaconic anhydride; and other monomers.

Meanwhile, the polymers used as a base resin of the resist composition of the present invention are preferably used in lithography of an ArF or a EUV lithography exposure, but can also be used in a KrF lithography, an electron beam lithography, and the like.

When the resist composition of the present invention is used in a KrF or an electron beam lithography, a preferable base resin may contain any one or more of the repeating units represented by the following general formulae (21) to (25), and in addition, any one or more of the repeating units represented by the general formulae (11) to (15).

(21)

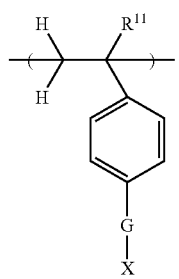

(22)

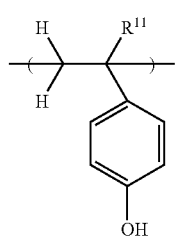

(23)

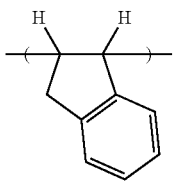

(24)

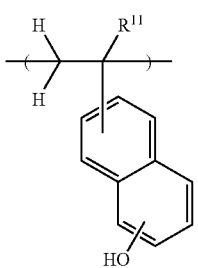

(25)

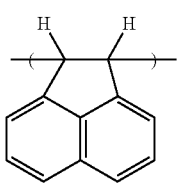

(In the formulae, $R^{11}$ and X represent the same as before. G represents an oxygen atom or a carbonyloxy group (—C(=O)O—)).

The polymer containing the repeating unit represented by the general formula (21) is decomposed by action of an acid to generate a phenolic hydroxyl group and/or a carboxylic acid thereby giving an alkaline-soluble polymer. Various kinds of the acid-labile group X may be used, wherein specific examples of them include the group represented by the general formulae (L1) to (L4), a tertiary alkyl group having 4 to 20, or preferably 4 to 15 carbon atoms, a trialkylsilyl group whose each alkyl group has 1 to 6 carbon atoms, and an oxoalkyl group having 4 to 20 carbon atoms.

Specific examples of the repeating units represented by the general formula (21) include the followings, but are not limited to them.

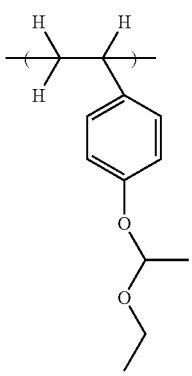 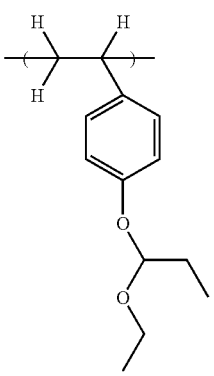

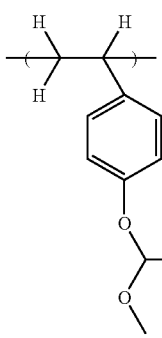 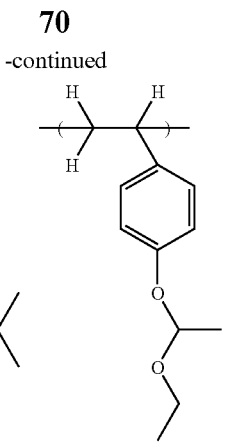

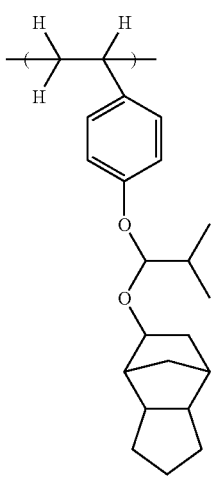 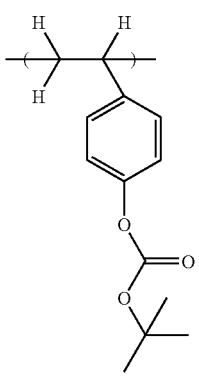

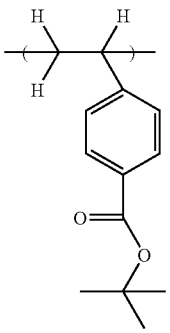 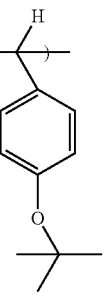 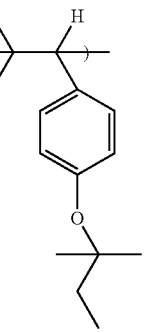

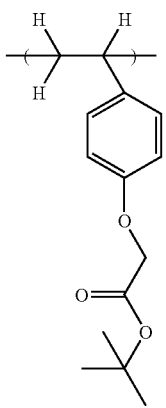 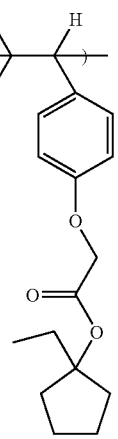

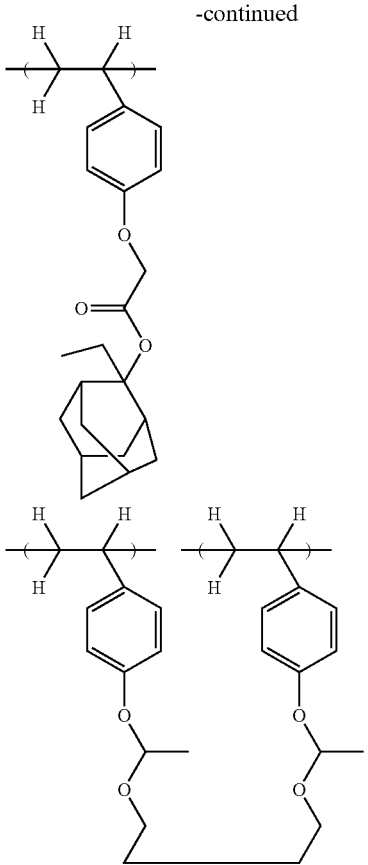

The position of substitution in the hydroxyvinylnaphthalene represented by the general formula (24) is arbitrary, but 6-hydroxy-2-vinylnaphthalene, 4-hydroxy-1-vinylnaphthalene, and the like may be used, while especially 6-hydroxy-2-vinylnaphthalene is preferably used.

In addition to any one of the repeating units represented by the general formulae (21) to (25), especially the one containing the repeating unit represented by the general formula (11) may be preferably used among the repeating units represented by the general formulae (11) to (15).

The polymer having any one or more of the repeating units represented by the general formulae (21) to (25) may contain a repeating unit derived from a monomer having a C—C double bond other than those described above. For example, it may contain a repeating unit derived from substituted acrylate esters such as methyl methacrylate, methyl crotonate, dimethyl maleate, and diemethyl itaconate; unsaturated carboxylic acids such as maleic acid, fumaric acid, and itaconic acid; cyclic olefins such as norbornene, a norbornene derivative, and a tetracyclo[6.2.1.1$^{3,6}$.0$^{2,7}$]dodecene derivative, norvornadiene; unsaturated acid anhydrides such as itaconic anhydride; styrene, acenaphthylene, vinyl naphthalene, and other monomers.

Meanwhile, the weight-average molecular weight of the polymer used as the base resin of the present invention is 1,000 to 500,000, or preferably 3,000 to 100,000. Outside this range, there may be the cases that the etching resistance is extremely deteriorated and the difference in dissolution rates before and after the exposure cannot be secured, thereby eroding the resolution. As to the measurement method of the molecular weight, a gel permeation chromatography (GPC) with the polystyrene conversion may be mentioned.

In the polymer used as the base resin of the resist composition of the present invention, the preferable ratio of each repeating unit derived from respective monomers can be made, for example, in the following ranges (% by mol), but is not limited to them.

(I) One kind, or two or more kinds of the composition units represented by the formulae (11) to (15) and/or (21) to (25) may be contained in the range of more than 0% by mol to 100% or less by mol, preferably 70 to 100% by mol, or more preferably 80 to 100% by mol, and as appropriate.

(II) One kind, or two or more kinds of the composition units derived from other monomers may be contained in the range of 0 to less than 100% by mol, preferably 0 to 30% by mol, or more preferably 0 to 20% by mol.

Here, as the base resin used in the chemically amplified positive resist composition of the present invention, the polymer having the repeating unit represented by the formula (11) or (21) is particularly preferable. The polymer having, in addition to the repeating units represented by the formulae (11), (12), and (13), or the formulae (21) and (22), the repeating unit represented by the formula (23) or (25) is further more preferable.

The polymer used as the base resin in the resist composition of the present invention is manufactured by copolymerizing a compound having a polymerizable double bond as the second monomer and the monomers following thereafter.

Although various copolymerization methods can be used for manufacturing the polymer used as the base resin in the resist composition of the present invention, a radical polymerization, an anionic polymerization, or a coordination polymerization is preferable.

Preferable reaction conditions of the radical polymerization are as follows, though outside these ranges are not excluded:
(a) solvent: hydrocarbons such as benzene, ethers such as tetrahydrofurane, alcohols such as ethanol, or ketones such as methyl isobutyl ketone,
(b) polymerization initiator: an azo compound such as 2,2'-azobisisobutyronitrile, or a peroxide such as benzoyl peroxide and lauroyl peroxide,
(c) reaction temperature: about 0° C. to about 100° C., and
(d) reaction time: about 0.5 hour to about 50 hours.

Preferable reaction conditions of the anionic polymerization are as follows, though outside these ranges are not excluded:
(a) solvent: hydrocarbons such as benzene, ethers such as tetrahydrofurane, or liquid ammonia,
(b) polymerization initiator: a metal such as sodium and potassium, an alkyl metal such as n-butyl lithium and sec-butyl lithium, a ketyl, or a Grignard reagent,
(c) reaction temperature: about −78° C. to about 0° C.,
(d) reaction time: about 0.5 hour to about 50 hours, and
(e) terminator: a proton-donating compound such as methanol, a halogen compound such as methyl iodide, and other electrophilic substances.

Preferable reaction conditions of the coordination polymerization are as follows, though outside these ranges are not excluded:
(a) solvent: hydrocarbons such as n-heptane and toluene,
(b) catalyst: a Ziegler-Natta catalyst containing a transition metal such as titanium and an alkyl aluminum, a Philips catalyst having a chromium and a nickel compound supported on a metal oxide, an olefin-metathesis mixed catalyst represented by the mixed catalyst of tungsten and rhenium, and the like, (c) reaction temperature: about 0° C. to about 100° C., and
(d) reaction time: about 0.5 hour to about 50 hours.

All or a part of the acid-labile groups in the polymer prepared by the polymerization methods are deprotected, and then it can be used for a negative-type material which will be described later. In addition, the acid-labile group can be introduced again into the polymer whose acid-labile group was deprotected thereby enabling to introduce the substituent group that is different from the acid-labile group introduced at the time of polymerization.

For example, 4-ethoxyethoxystyrene and other polymerizable compound are polymerized by a radical polymerization to give a polymer, and then the ethoxyethyoxy group is removed by acetic acid, pyridinium tosylate, and the like to obtain a copolymer with polyhydroxy styrene. This can be used as a base resin for the negative resist composition. Further, by reacting the hydroxy styrene unit of the copolymer with di-tert-butyl dicarbonate, tert-butyl chloroacetate, various vinyl ethers, and the like, an acid-labile group different from the acid-labile group attached at the time of the polymerization (the ethoxyethoxy group) can be introduced.

In addition to the polymers, other resin whose dissolution rate in an alkaline developer is increased by action of an acid may also be added as appropriate. Examples of the resin include (i) a poly(meth)acrylic acid derivative, (ii) a copolymer of a norbornene derivative and maleic anhydride, (iii) a hydrogenated substance of a ring-opening methathesis polymer, (iv) a copolymer of a vinyl ether, maleic anhydride, and a (meth)acrylic acid derivative, and (v) a polyhydroxy styrene derivative, though are not limited to them.

The poly(meth)acrylic acid derivative in (i) is a polymer formed of a combination of the general formulae (11) to (15), and the like, and the polyhydroxy styrene derivative in (v) is a polymer formed of a combination of the formulae (21) to (25) and a combination of the formulae (11) to (15) and (21) to (25). The ratio of the units relating to the acid-labile group in the polymer, for example, the ratio of one kind or two or more kinds of the monomer units represented by the general formula (11) and/or (21) is in the range of more than 0% by mol to 80% or less by mol, preferably 1 to 50% by mol, or more preferably 10 to 40% by mol. The ratio of the units relating to the group other than the acid-labile group in the polymer, for example, the ratio of one kind or two or more kinds of the monomer units represented by the general formulae (12) to (15) and/or (22) to (25), is in the range of 0% or more by mol to less than 100% by mol, and when containing it, preferably 20% or more by mol to less than 100% by mol, more preferably 50 to 99% by mol, and particularly preferably 60 to 90% by mol.

Among them, a synthetic method for the hydrogenated substance of a ring-opening methathesis polymer is specifically disclosed in Example of Japanese Patent Application Laid-Open No. 2003-66612. Specific examples of the polymer are those having the following repeating units, but not limited to them.

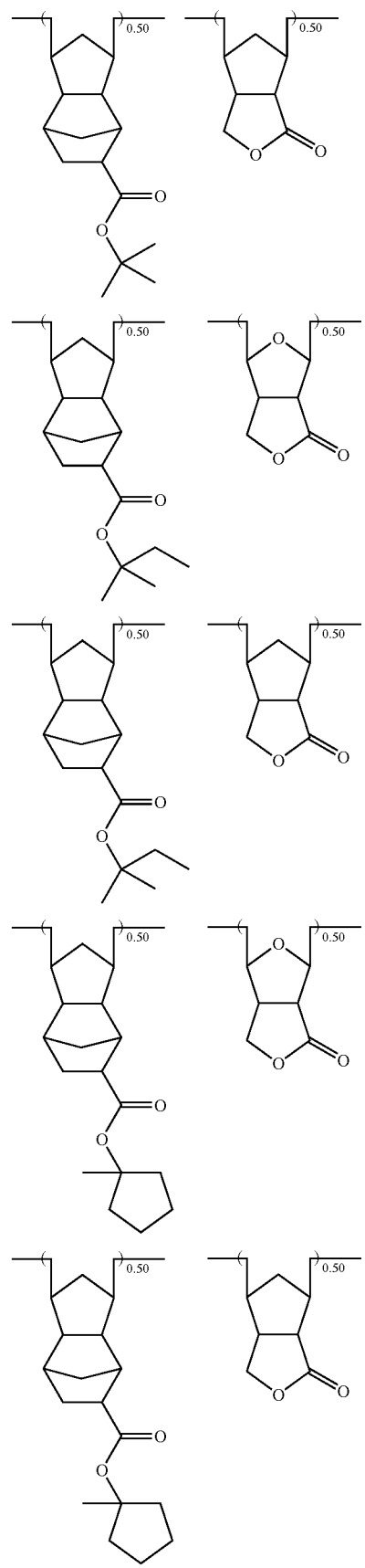

75
-continued
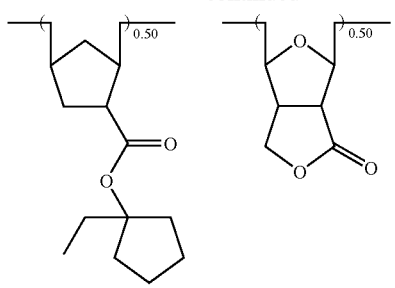
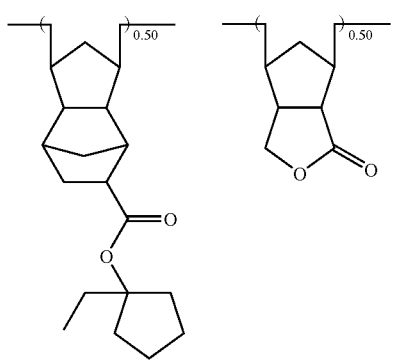
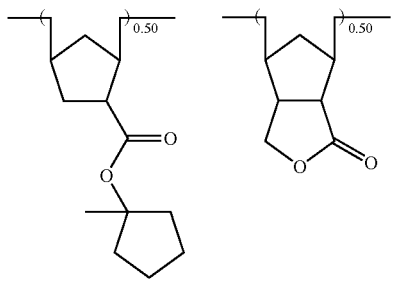
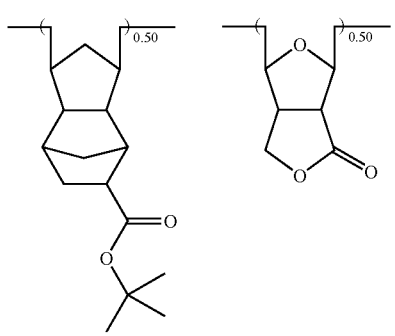
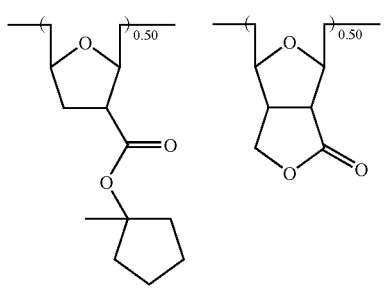
76
-continued
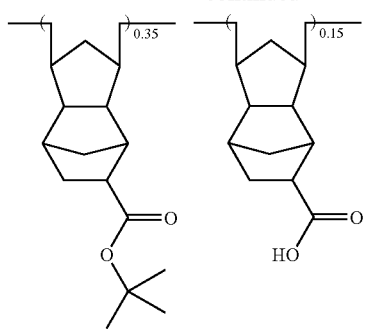
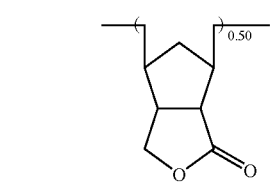
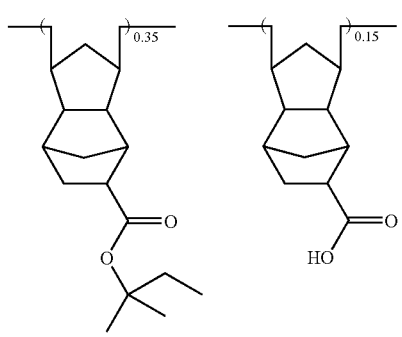
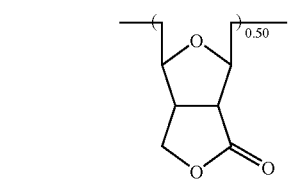
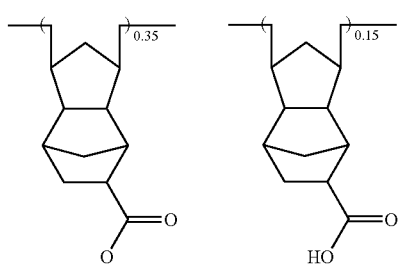
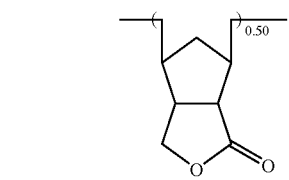

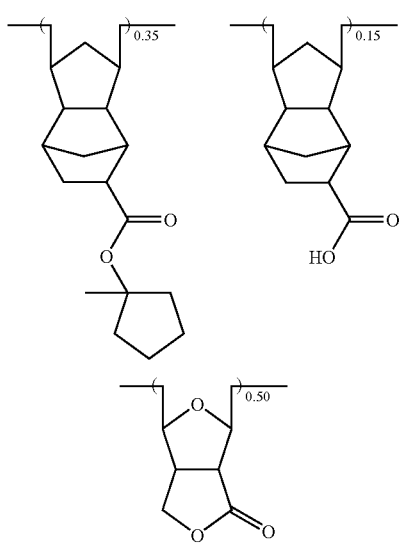
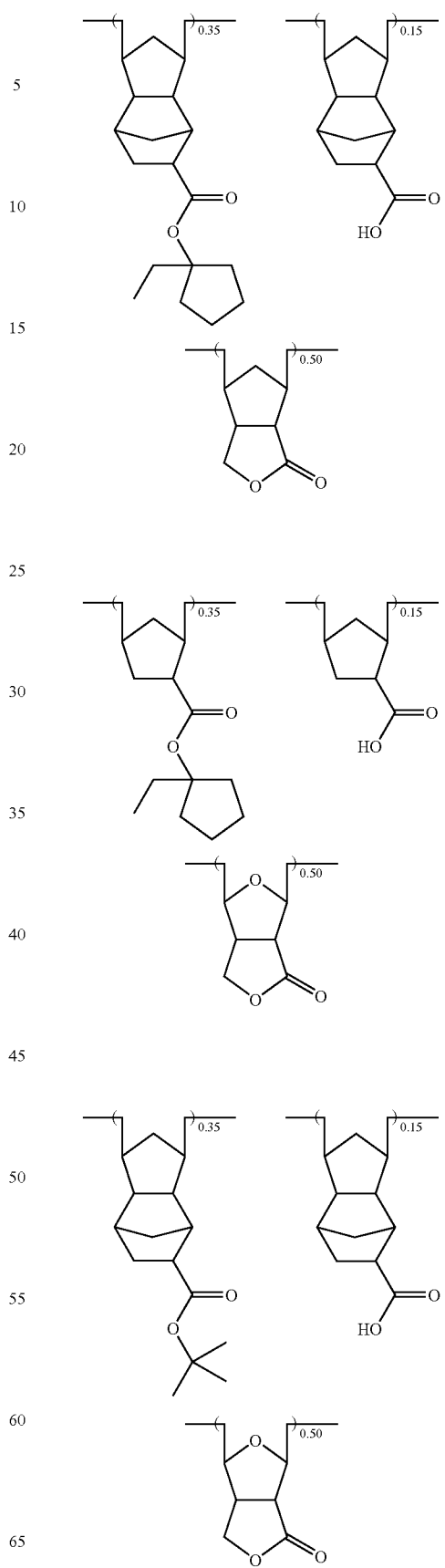

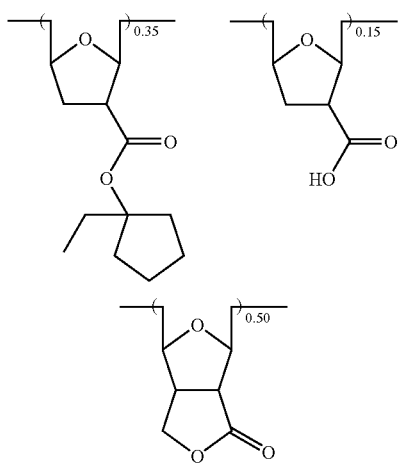

The blending ratio of the polymer usable as the base resin of the resist composition of the present invention to other polymer is in the mass range of preferably 100:0 to 10:90, in particular 100:0 to 20:80. When the blending ratio of the polymer used as the base resin of the resist composition of the present invention is below this range, there may be a case that a suitable performance as the resist composition cannot be obtained. Performance of the resist composition can be controlled by appropriately changing the blending ratio.

Here, not only one kind but also two or more kinds of the polymers can be added. Performance of the resist composition can be controlled by adding a plurality of the polymers.

As to the organic solvent of the (B) component used in the present invention, any organic solvent may be used as far as it can dissolve a base resin, an acid generator, other additive, and so on. Specific examples of the organic solvent are disclosed in paragraphs [0144] to [0145] of Japanese Patent Application Laid-Open No. 2008-111103.

In addition to the photosensitive acid generator of the present invention, an acid generator of the (C) component other than the photosensitive acid generator of the present invention may be used as appropriate. Any compound can be used as the photosensitive acid generator of the (C) component as far as it generates an acid by exposure to a high energy beam. A suitable photosensitive acid generator includes an acid generator with the type of a sulfonium salt, an iodonium salt, a sulfonyl diazomethane, an N-sulonyl oxyimide, and an oxime-O-solufonate, and the like. These may be used singly or as a mixture of two or more kinds. These are elaborated in Japanese Patent Application Laid-Open No. 2008-133448, and so on.

When an acid generator of the (C) component is jointly used with the photosensitive acid generator of the present invention, a particularly preferably used acid generator in the ArF lithography application is the one represented by the following general formula (C)-1.

(C)-1

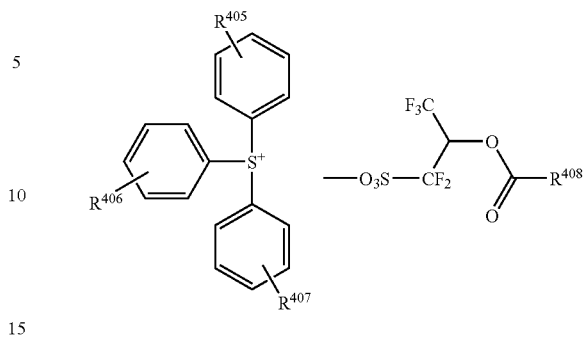

Here, in the formula, each $R^{405}$, $R^{406}$, and $R^{407}$ independently represents a hydrogen atom, or a linear, a branched, or a cyclic monovalent hydrocarbon group, in particular an alkyl group or an alkoxy group, having 1 to 20 carbon atoms optionally containing a hetero atom. Specific examples of the hydrocarbon group optionally containing a hetero atom include a methyl group, an ethyl group, a propyl group, an isopropyl group, a n-butyl group, a sec-butyl group, a tent-butyl group, a tert-amyl group, a n-pentyl group, a n-hexyl group, a cyclopentyl group, a cyclohexyl group, an ethyl cyclopentyl group, a butyl cyclopentyl group, an ethyl cyclohexyl group, a butyl cyclohexyl group, an adamantyl group, an ethyl amadantyl group, a butyl adamantyl group, a group having a hetero atomic group such as —O—, —S—, —SO—, —SO$_2$—, —NH—, —C(=O)—, —C(=O)O—, and —C(=O)NH— between an arbitrary C—C bond in those groups, and a group whose arbitrary hydrogen atom is substituted by a functional group such as —OH, —NH$_2$, —CHO, and —CO$_2$H. $R^{408}$ represents a linear, a branched, or a cyclic monovalent hydrocarbon group having 7 to 30 carbon atoms optionally containing a hetero atom, wherein specific examples include the followings, though are not limited to them.

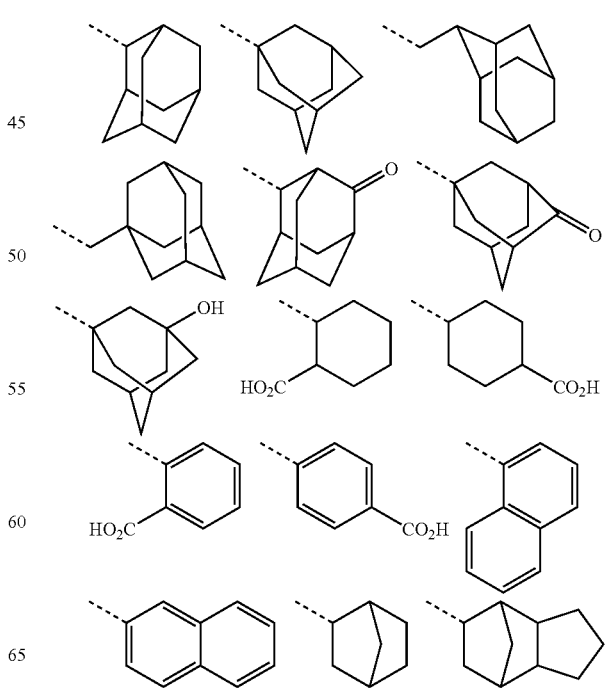

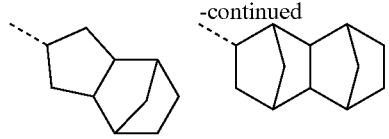
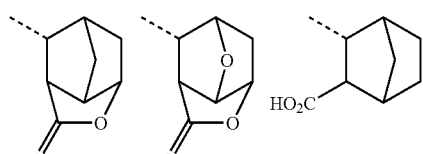
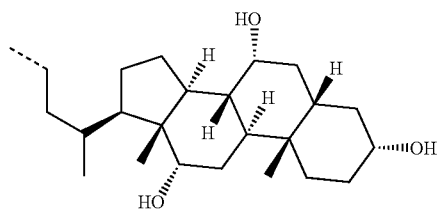
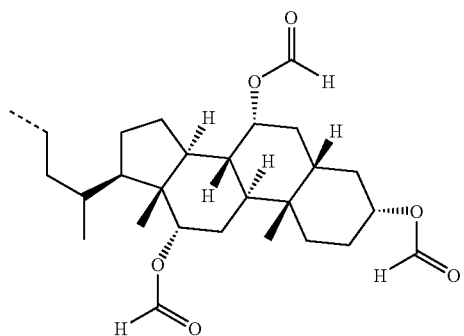
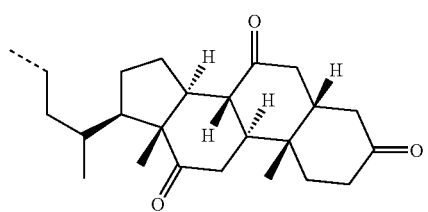
Specific examples of (C)-1 include the followings.
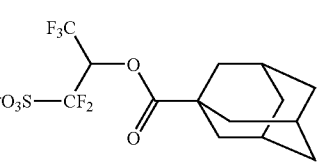
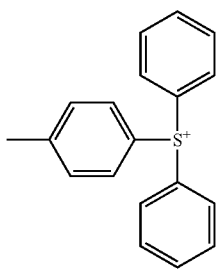
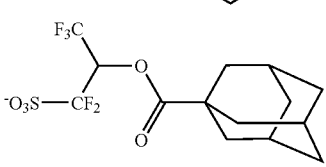
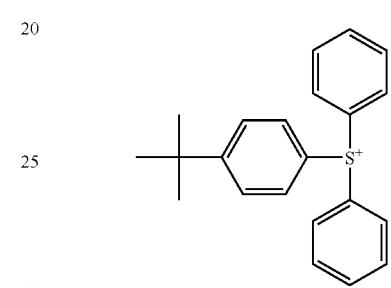
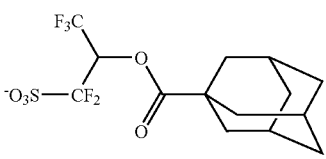
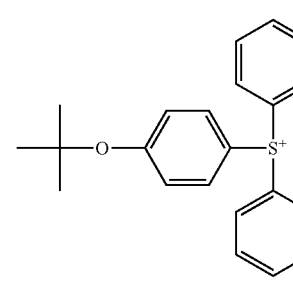
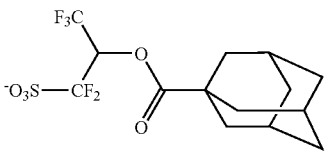
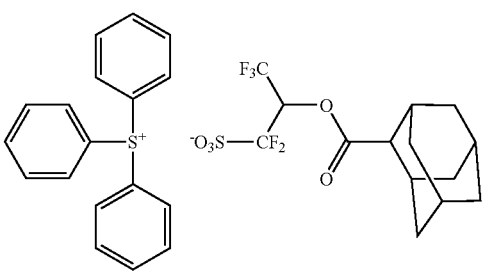

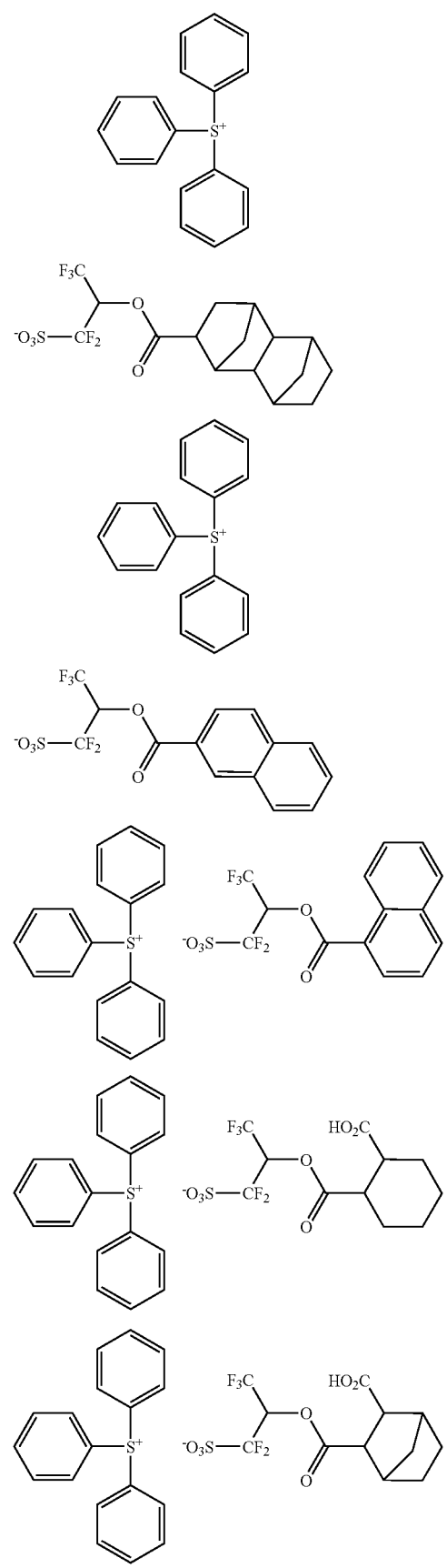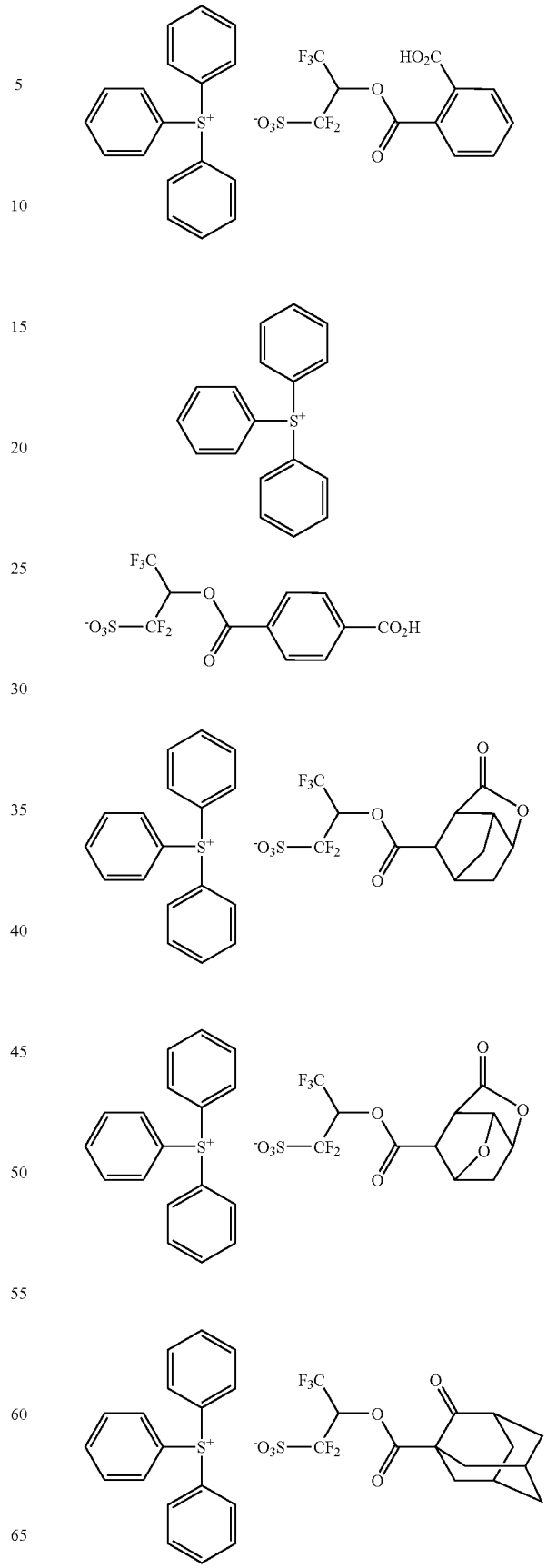

-continued

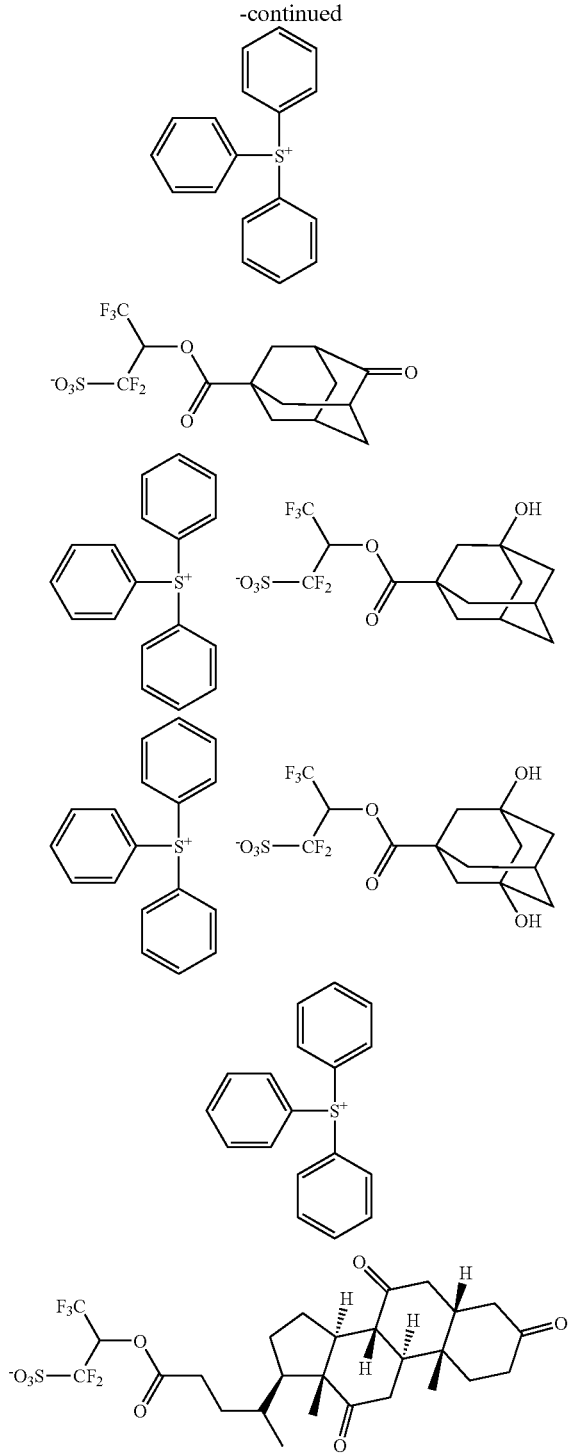

When two or more kinds of the photosensitive acid generators are used and one of them is an onium salt generating a so-called weak acid, the function to control the acid diffusion can also be given. Namely, when a mixture of an onium salt generating a strong acid like a fluorine-substituted sulfonic acid as described before and an onium salt generating a weak acid like a fluorine-unsubstituted sulfonic acid or a carboxylic acid is used, a strong acid generated from the photosensitive acid generator by exposure to a high energy beam collides with the onium salt having an unreacted weak acid thereby releasing the weak acid and forming the onium salt having the strong acid anion by the salt-exchange. In this process, the strong acid is exchanged to the weak acid having a lower catalytic activity, and thus the acid is apparently deactivated thereby enabling to control the acid diffusion.

Here, when the photosensitive acid generator generating a strong acid is an onium salt, the strong acid generated by exposure to a high energy beam can exchange with a weak acid as mentioned above, but a weak acid generated by exposure to a high energy beam cannot undergo the salt exchange by collision with an unreacted onium salt generating a strong acid. These are caused by the phenomenon that an onium cation forms an ion pair more easily with an anion of a more stronger acid.

When the photosensitive acid generator of the present invention is used as a mixture with an acid generator generating an acid like those represented by the general formula (C-1), for example, α,α'-difluorosulfonic acid, the acid strength of the photosensitive acid generator of the present invention is weaker than it. Accordingly, in this case, the photosensitive acid generator of the present invention acts apparently as a quencher by the above-mentioned reasons, and as a result, the acid diffusion can be controlled.

The amount of the photosensitive acid generator added as the component (C) in the chemically amplified resist composition of the present invention other than the photosensitive acid generator of the present invention is not particularly restricted when it is within a range not impairing the effects of the present invention. However, the total adding amount of the photosensitive acid generator of the present invention and the photosensitive acid generator of the component (C) is preferably 0.1 to 10 parts by mass, in particular 0.1 to 5 parts by mass, relative to 100 parts by mass of the base resin in the resist composition. When the ratio of the photosensitive acid generator of the component (C) is too large, there is a possibility of deterioration in resolution and causing a problem of foreign materials at the time of development and resist delamination. The photosensitive acid generator of the component (C) may also be used singly or as a mixture of two or more kinds. In addition, by using a photosensitive acid generator having a low transmittance at the exposure wavelength, transmittance in a resist film can also be controlled by its adding amount.

Furthermore, a compound generating an acid by acidic decomposition (acid proliferation compound) may be added to the resist composition of the present invention. These compounds are disclosed in J. Photopolym. Sci. and Tech., 8. 43-44 and 45-46 (1995) and J. Photopolym. Sci. and Tech., 9. 29-30 (1996).

Examples of the acid proliferation compound include tert-butyl-2-methyl-2-tosyloxymethyl acetoacetate and 2-phenyl-2-(2-tosyloxyethyl)-1,3-dioxolane, but it is not limited to them. Among heretofore known photosensitive acid generators, a compound having a poor stability, especially a poor thermal stability, shows the properties of the acid proliferation compound in many cases.

The adding amount of the acid proliferation compound in the resist composition of the present invention is 2 or less parts by mass, or preferably 1 or less part by mass, relative to 100 parts by mass of the base resin in the resist composition. When the adding amount is too large, control of the diffusion is difficult, leading to possible deterioration of the resolution and the pattern form.

In the resist composition of the present invention, one kind or two or more kinds of the quenchers of the component (D) may be blended.

The term "quencher" is widely used in this technical field, and means a compound that can suppress the diffusion rate of an acid and the like generated from an acid generator into a resist film. By blending a quencher, not only control of the resist sensitivity can be made easier but also the diffusion rate of an acid in the resist film can be suppressed thereby leading to increase in resolution, and this in turn leads to suppressing the sensitivity change after exposure, decreasing dependency on a substrate and an environment, improving the exposure margin and the pattern profile, and the like.

As such quencher, primary, secondary and tertiary aliphatic amines, combined amines, aromatic amines, heterocyclic amine, nitrogen-containing compound having a carboxyl group, a nitrogen-containing compound having sulfonyl group, a nitrogen-containing compound having a hydroxyl group, a nitrogen-containing compound having hydroxyphenyl group, an alcoholic nitrogen-containing compound, amides, imides, carbamates, ammonium salts, etc. are preferably used.

Specific examples of the quencher, it is described in paragraph [0146]-[0163] of a Japanese Patent Laid-Open No. 2008-111103.

Quencher used more preferably is tertiary amines, and specifically tri-n-butylamine, tri-n-pentyl amine, tri-n-hexylamine, tri-n-octylamine, N,N-dimethylaniline, tri(2-methoxyethoxyethyl)amine, triethanolamine, triisopanolamine, tri(2-methoxymethoxyethyl)amine, tri{2-(2-methoxyethoxy)ethyl}amine, tri{2-(2-methoxyethoxymethoxy)ethyl}amine, tri{2-(1-methoxyethoxy)ethy})amine, tri{2-(1-ethoxyethoxy)ethyl}amine, tri{2-(1-ethoxypropoxy)ethyl}amine, tri[2-{2-(2-hydroxyethoxy)ethoxy}ethyl]amine, 4,7,13,16,21,24-hexaoxa-1,10-diazabicyclo[8.8.8]hexacosane, 4,7,13,18-tetraoxa-1,10-diazabicyclo[8.5.5]eicosane, 1,4,10,13-tetraoxa-7,16-diazabicyclooctadecane, 1-aza-12-crown-4,1-aza-15-crown-5,1-aza-18-crown-6, tris(2-formyloxyethyl)amine, tris(2-acetoxyethyl)amine, tris(2-propyonyloxyethyl)amine, tris(2-butyryloxyethyl)amine, tris(2-isobutyryloxyethyl)amine, tris(2-valeryloxyethyl)amine, tris(2-pivaloyloxyethyl)amine, N,N-bis(2-acetoxyethyl)2-(acetoxyacetoxy)ethylamine, tris(2-methoxycarbonyloxyethyl)amine, tris(2-tert-butoxycarbonyloxyethyl)amine, tris[2-(2-oxopropoxy)ethyl]amine, tris[2-(methoxycarbonylmethyl)oxyethyl]amine, tris[2-(tert-butoxycarbonylmethyloxy)ethyl]amine, tris[2-(cyclohexyloxycarbonylmethyloxy)ethyl]amine, tris(2-methoxycarbonylethyl)amine, tris(2-ethoxycarbonylethyl)amine, tris(2-benzoyloxyethyl)amine, tris[2-(4-methoxybenzoyloxy)ethyl]amine, N,N-bis(2-hydroxyethyl)2-(methoxycarbonyl)ethylamine, N,N-bis(2-acetoxyethyl)2-(methoxycarbonyl)ethylamine, N,N-bis(2-hydroxyethyl)2-(ethoxycarbonyl)ethylamine, N,N-bis(2-acetoxyethyl)2-(ethoxycarbonyl)ethylamine, N,N-bis(2-hydroxyethyl)2-(2-methoxyethoxycarbonyl)ethylamine, N,N-bis(2-acetoxyethyl)2-(2-methoxyethoxycarbonyl)ethylamine, N,N-bis(2-hydroxyethyl)2-(2-hydroxyethoxycarbonyl)ethyl amine, N,N-bis(2-acetoxyethyl)2-(2-acetoxyethoxycarbonyl)ethyl amine, N,N-bis(2-hydroxyethyl)2-[(methoxycarbonyl)methoxycarbonyl]ethylamine, N,N-bis(2-acetoxyethyl)2-[(methoxycarbonyl)methoxycarbonyl]ethylamine, N,N-bis(2-hydroxyethyl)2-(2-oxopropoxycarbonyl)ethylamine, N,N-bis(2-acetoxyethyl)2-(2-oxopropoxycarbonyl)ethylamine, N,N-bis(2-hydroxyethyl)2-(tetrahydrofurfuryloxy)carbonyl)ethylamine, N,N-bis(2-acetoxyethyl)2-(tetrahydrofurfuryloxycarbonyl)ethylamine, N,N-bis(2-hydroxyethyl)2-[(2-oxotetrahydrofuran-3-yl)oxycarbonyl]ethylamine, N,N-bis(2-acetoxyethyl)2-[(2-oxotetrahydrofuran-3-yl)oxycarbonyl]ethylamine, N,N-bis(2-hydroxyethyl)2-(4-hydroxybutoxycarbonyl)ethylamine, N,N-bis(2-formyloxyethyl)2-(4-formyloxybutoxycarbonyl)ethylamine, N,N-bis(2-formyloxyethyl)2-(2-formyloxyethoxycarbonyl)ethylamine, N,N-bis(2-methoxyethyl)2-(methoxycarbonyl)ethylamine, N-(2-hydroxyethyl)bis[2-(methoxycarbonyl)ethyl]amine, N-(2-acetoxyethyl)bis[2-(methoxycarbonyl)ethyl]amine, N-(2-hydroxyethyl)bis[2-(ethoxycarbonyl)ethyl]amine, N-(2-acetoxyethyl)bis[2-(ethoxycarbonyl)ethyl]amine, N-(3-hydroxy-1-propyl)bis[2-(methoxycarbonyl)ethyl]amine, N-(3-acetoxy-1-propyl)bis[2-(methoxycarbonyl)ethyl]amine, N-(2-methoxyethyl)bis[2-(methoxycarbonyl)ethyl]amine, N-butylbis[2-(methoxycarbonyl)ethyl]amine, N-butylbis[2-(2-methoxyethoxycarbonyl)ethyl]amine, N-methylbis(2-acetoxyethyl)amine, N-ethylbis(2-acetoxyethyl)amine, N-methylbis(2-pivaloyloxyethyl)amine, N-ethylbis[2-(methoxycarbonyloxy)ethyl]amine, N-ethylbis[2-(tert-butoxycarbonyloxy)ethyl]amine, tris(methoxycarbonylmethyl)amine, tris(ethoxycarbonylmethyl)amine, N-butylbis(methoxycarbonylmethyl)amine, N-hexylbis(methoxycarbonylmethyl)amine, β-(diethylamino)-δ-valerolactone are exemplified.

Furthermore, it is 1-[2-(methoxymethoxy)ethyl]pyrrolidine, 1-[2-(methoxymethoxy)ethyl]piperidine, 4-[2-(methoxymethoxy)ethyl]morpholine, 1-[2-(methoxymethoxy)ethyl]imidazole, 1-[2-(methoxymethoxy)ethyl]Ben imidazole, 1-[2-(methoxymethoxy)ethyl]-2-phenylbenzimidazole, 1-[2-[(2-methoxyethoxy)methoxy]ethyl]pyrrolidine, 1-[2-[(2-methoxyethoxy)methoxy]ethyl]piperidine, 4-[2-[(2-methoxyethoxy)methoxy]ethyl]morpholine, 1-[2-[(2-methoxyethoxy)methoxy]ethyl]imidazole, 1-[2-[(2-methoxyethoxy)methoxy]ethyl]Ben imidazole, 1-[2-[(2-methoxyethoxy)methoxy]ethyl]-2-phenylbenzimidazole, 1-[2-[2-(2-methoxyethoxy)ethoxy]ethyl]pyrrolidine, 1-[2-[2-(2-methoxyethoxy)ethoxy]ethyl]piperidine, 4-[2-[2-(2-methoxyethoxy)ethoxy]ethyl]morpholine, 1-[2-[2-(2-methoxyethoxy)ethoxy]ethyl]imidazole, 1-[2-[2-(2-methoxyethoxy)ethoxy]ethyl]Ben imidazole, 1-[2-[2-(2-methoxyethoxy)ethoxy]ethyl]-2-phenylbenzimidazole, 1-[2-[2-(2-butoxyethoxy)ethoxy]ethyl]pyrrolidine, 1-[2-[2-(2-butoxyethoxy)ethoxy]ethyl]piperidine, 4-[2-[2-(2-butoxyethoxy)ethoxy]ethyl]morpholine, 1-[2-[2-(2-butoxyethoxy)ethoxy]ethyl]imidazole, 1-[2-[2-(2-butoxyethoxy)ethoxy]ethyl]benzimidazole, 1-[2-[2-(2-butoxyethoxy)ethoxy]ethyl]-2-phenylbenzimidazole, 1-[2-[2-[2-(2-methoxyethoxy)ethoxy]ethoxy]ethyl]pyrrolidine, 1-[2-[2-[2-(2-methoxyethoxy)ethoxy]ethoxy]ethyl]piperidine, 4-[2-[2-[2-(2-methoxyethoxy)ethoxy]ethoxy]ethyl]morpholine, 1-[2-[2-[2-(2-methoxyethoxy)ethoxy]ethoxy]ethyl]imidazole, 1-[2-[2-[2-(2-)methoxyethoxy)ethoxy]ethoxy]ethyl]benzimidazole, 1-[2-[2-[2-(2-methoxyethoxy)ethoxy]ethoxy]ethyl]-2-phenylbenzimidazole, 4-[2-[2-[2-(2-butoxyethoxy)ethoxy]ethoxy)ethyl]morpholine, acetic acid 2-(1-pyrrolidinyl)ethyl, acetic acid 2-piperidinoethyl, acetic acid 2-morpholinoethyl, acetic acid 2-(1-imidazolyl)ethyl, acetic acid 2-(1-benzimidazolyl)ethyl, acetic acid 2-(2-phenyl-1-benzimidazolyl)ethyl, morpholino acetic acid 2-methoxyethyl, 2-methoxy acetic acid 2-(1-pyrrolidinyl)ethyl, 2-methoxy acetic acid 2-piperidinoethyl, 2-methoxy acetic acid 2-morpholinoethyl, 2-methoxy acetic acid 2-(1-imidazolyl)ethyl, 2-methoxy acetic acid 2-(1-benzimidazolyl)ethyl, 2-methoxy acetic acid 2-(2-phenyl-1-benzimidazolyl)ethyl, 2-(2-methoxyethoxy)acetic acid 2-(1-pyrrolidinyl)ethyl, 2-(2-methoxyethoxy)acetic acid 2-piperidinoethyl, 2-(2-methoxyethoxy)acetic acid 2-morpholinoethyl, 2-(2-methoxyethoxy)acetic acid 2-(1-imidazolyl)ethyl, 2-(2-methoxyethoxy)acetic acid 2-(1-benzimidazolyl)ethyl, 2-(2-methoxyethoxy)acetic acid 2-(2-phenyl-1-benzimidazolyl)ethyl, 2-[2-(2-methoxyethoxy)ethoxy]acetic acid 2-(1- pyrrolidinyl)ethyl, 2-[2-(2-methoxyethoxy)ethoxy]acetic acid 2-piperidinoethyl, 2-[2-(2-methoxyethoxy)ethoxy]acetic acid 2-morpholinoethyl, 2-[2-(2-methoxyethoxy)ethoxy]acetic acid 2-(1-imidazolyl)ethyl, 2-[2-(2-methoxyethoxy)ethoxy]acetic acid 2-(1-benzimidazolyl)ethyl, 2-[2-(2-methoxyethoxy)ethoxy]acetic acid 2-(2-phenyl-1-benzimidazolyl)ethyl, butyric acid 2-morpholinoethyl, hexanoic acid 2-morpholinoethyl, octane acid 2-morpholinoethyl, decane acid 2-morpholinoethyl, lauric acid 2-morpholinoethyl, myristin acid 2-morpholinoethyl, palmitic acid 2-morpholinoethyl, stearin acid 2-morpholinoethyl, behenic acid 2-morpholinoethyl, cholic acid 2-morpholinoethyl, tris (O-acetyl) call acid 2-morpholino Ethyl, tri(O-formyl)cholic acid 2-morpholinoethyl, dehydrocholic acid 2-morpholinoethyl, cyclopentane carboxylic acid 2-morpholinoethyl, cyclohexanecarboxylic acid 2-morpholinoethyl, 7-oxanorbornane-2-carboxylic acid 2-(1-pyrrolidinyl)ethyl, 7-oxanorbornane-2-carboxylic acid 2-piperidinoethyl, 7-oxanorbornane-2-carboxylic acid 2-morpholinoethyl, 7-oxanorbornane-2-carboxylic acid 2-(1-imidazolyl)ethyl, 7-oxanorbornane-2-carboxylic acid 2-(1-benzimidazolyl)ethyl, 7-oxanorbornane-2-carboxylic acid 2-(2-phenyl-1-benzimidazolyl)ethyl, adamantane carboxylic acid 2-morpholinoethyl, formic acid 2-(1-pyrrolidinyl)ethyl, propione acid 2-piperidinoethyl, acetoxy acetic acid 2-morpholinoethyl, methoxy acetic acid 2-(1-pyrrolidinyl)ethyl, benzoic acid 2-(1-pyrrolidinyl)ethyl, benzoic acid 2-piperidinoethyl, benzoic acid 2-morpholinoethyl, benzoic acid 2-(1-imidazolyl)ethyl, benzoic acid 2-(1-benzimidazolyl)ethyl, benzoic acid 2-(2-phenyl)-1-benzimidazolyl)ethyl, 4-methoxy benzoic acid 2-(1-pyrrolidinyl)ethyl, 4-methoxy benzoic acid 2-piperidinoethyl, 4-methoxy benzoic acid 2-morpholinoethyl, 4-methoxy benzoic acid 2-(1-imidazolyl)ethyl, 4-methoxy benzoic acid 2-(1-benzimidazolyl)ethyl, 4-methoxy benzoic acid 2-(2-phenyl-1-benzimidazolyl)ethyl, 4-phenyl benzoic acid 2-(1-pyrrolidinyl)ethyl, 4-phenyl benzoic acid 2-piperidinoethyl, 4-phenyl benzoic acid 2-morpholinoethyl, 4-phenyl benzoic acid 2-(1-imidazolyl)ethyl, 4-phenyl benzoic acid 2-(1-benzimidazolyl)ethyl, 4-phenyl benzoic acid 2-(2-phenyl-1-benzimidazolyl)ethyl, 1-naphthalene carboxylic acid 2-(1-pyrrolidinyl)ethyl, 1-naphthalene carboxylic acid 2-piperidinoethyl, 1-naphthalene carboxylic acid 2-morpholinoethyl, 1-naphthalene carboxylic acid 2-(1-imidazolyl)ethyl, 1-naphthalene carboxylic acid 2-(1-benzimidazolyl)ethyl, 1-naphthalene carboxylic acid 2-(2-phenyl-1-benzimidazolyl)ethyl, 2-naphthalene carboxylic acid 2-(1-pyrrolidinyl)ethyl, 2-naphthalene carboxylic acid 2-piperidinoethyl, 2-naphthalene carboxylic acid 2-morpholinoethyl, 2-naphthalene carboxylic acid 2-(1-imidazolyl)ethyl, 2-naphthalene carboxylic acid 2-(1-benzimidazolyl)ethyl, 2-naphthalene carboxylic acid 2-(2-phenyl-1-benzimidazolyl)ethyl, 4-[2-(methoxycarbonyloxy)ethyl]morpholine, 1-[2-(tent-butoxycarbonyloxy)ethyl]piperidine, 4-[2-(2-methoxyethoxycarbonyloxy)ethyl]morpholine, 3-(1-pyrrolidinyl)propione acid methyl, 3-piperidinopropione acid methyl, 3-morpholinopropione acid methyl, 3-(thiomorpholino)propione acid methyl, 2-methyl-3-(1-pyrrolidinyl)propione acid methyl, 3-morpholinopropione acid ethyl, 3-piperidinopropione acid methoxycarbonylmethyl, 3-(1-pyrrolidinyl)propione acid 2-hydroxyethyl, 3-morpholinopropione acid 2-acetoxyethyl, 3-(1-pyrrolidinyl)propione acid 2-oxotetrahydrofuran-3-yl, 3-morpholinopropione acid tetrahydrofurfuryl, 3-piperidinopropione acid glycidyl, 3-morpholinopropione acid 2-methoxyethyl, 3-(1-pyrrolidinyl)propione acid 2-(2-methoxyethoxy)ethyl, 3-morpholinopropione acid butyl, 3-piperidinopropione acid cyclohexyl, α-(1-pyrrolidinyl)methyl-γ-butyrolactone, β-piperidino-γ-butyrolactone, β-morpholino-δ-valerolactone, 1-pyrrolidinyl acetic acid methyl, piperidino acetic acid methyl, morpholino acetic acid methyl, thiomorpholino acetic acid methyl, 1-pyrrolidinyl ethyl acetate, etc are exemplified.

Here, the blending amount of the quencher is preferably 0.001 to 5 parts by mass, in particular 0.01 to 3 parts by mass, relative to 100 parts by mass of the total base resins. When the blending amount is less than 0.001 parts by mass, blending effects are not realized, and when the amount is more than 5 parts by mass, there is a case that the sensitivity becomes too low.

In the resist composition of the present invention, in order to improve the coating properties, a conventionally used surfactant (E) may be added as an arbitrary component in addition to the components. Here, the adding amount of the arbitrary component is usual in the range not impairing the effects of the present invention.

Specific examples of the surfactant are disclosed in the paragraphs of [0165] to [0166] of Japanese Patent Application Laid-Open No. 2008-111103. In addition, a surfactant of a partially fluorinated oxetane ring-opened polymer as represented by the following structural formula (surf-1) may also be preferably used.

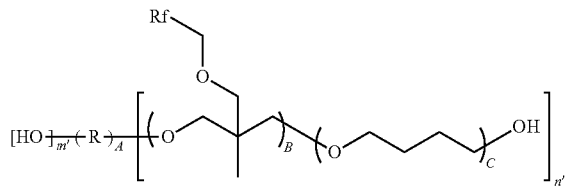

(surf-1)

Here, R, Rf, A, B, C, m', and n' are applied only to the above formula (surf-1) regardless of the description made on substances other than the surfactants. R represents a 2-to 4-valent aliphatic group having 2 to 5 carbon atoms, specifically ethylene, 1,4-butylene, 1,2-propylene, 2,2-dimethyl-1,3-propylene, and 1,5-pentylene and the like, as the divalent group. Examples of the trivalent group and the tetravalent group may be as follows.

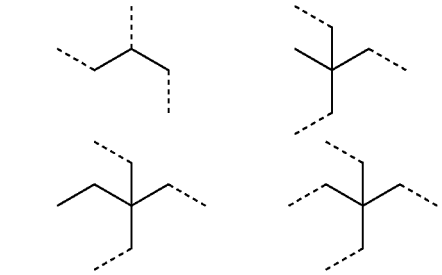

(In the formulae, the dotted lines show bonding hands and each represents a partial structure derived from glycerol, trimethylol ethane, trimethylol propane, and pentaerythritol.)

Among them, 1,4-butylene or 2,2-dimethyl-1,3-propylene is preferably used.

Rf represents a trifluoromethyl group or a pentafluoroethyl group, and preferably a trifluoromethyl group. "m'" represents an integer of 0 to 3 and "n'" represents an integer of 1 to 4, wherein the sum of "m'" and "n'" is the valency of R and is 2 to 4. "A" represents 1, "B" represents an integer of 2 to 25, and "C" represents an integer of 0 to 10. Preferably, "B" represents an integer of 4 to 20 and "C" represents 0 or 1. Each structural unit in the structures does not stipulate the sequence of them, and they may be bonded in blocks or randomly. Manufacturing of the partially fluorinated oxetane ring-opened polymer surfactant is elaborated in the description of U.S. Pat. No. 5,650,483 and so on.

Among the surfactants, FC-4430, Surflon S-381, Surfynol E1004, KH-20, KH-30, and the oxetane ring-opened polymer represented by the structural formula (surf-1) are preferable. These may be used singly or in a combination of two or more kinds.

The adding amount of the surfactant in the chemically amplified resist composition of the present invention is 2 or less parts by mass, or preferably 1 or less parts by mass, and when blended, preferably 0.01 or more part by mass, relative to 100 parts by mass of the base resin in the resist composition.

In the resist composition of the present invention, a surfactant having a function to reduce water penetration and leaching by orientating on the resist surface after spin coating may be added in the case of the immersion exposure using water, especially when a resist top coat is not used. This surfactant is of a polymer type having a property to be dissolved in an alkaline developer but not in water, and in particular the one giving a high water-repellent property with an improved sliding property is preferable. A polymer-type surfactant like the foregoing can be shown as follows.

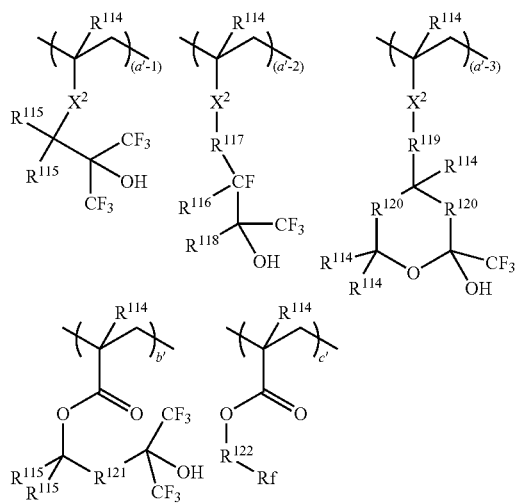

(In the formula, each $R^{114}$ may be the same or different and represents a hydrogen atom, a fluorine atom, a methyl group, or a trifluoromethyl group. Each $R^{115}$ may be the same or different and represents a hydrogen atom, or a linear, a branched, or a cyclic alkyl or fluorinated alkyl group having 1 to 20 carbon atoms, wherein $R^{115}$ in the same monomer may be bonded with each other to form a ring together with the carbon atoms to which they are bonded, and in that case, it represents a linear, a branched, or a cyclic alkylene or fluorinated alkylene group having 2 to 20 total carbon atoms. $R^{116}$ represents a fluorine atom or a hydrogen atom, or may be bonded with $R^{117}$ to form a non-aromatic ring having 3 to 10 total carbon atoms together with the carbon atoms to which they are bonded. $R^{117}$ represents a linear, a branched, or a cyclic alkylene group having 1 to 6 carbon atoms whose one or more hydrogen atom may be substituted by a fluorine atom. $R^{118}$ represents a linear or a branched alkyl group having 1 to 10 carbon atoms whose one or more hydrogen atom is substituted by a fluorine atom, wherein $R^{117}$ and $R^{118}$ may be bonded to form a non-aromatic ring together with the carbon atoms to which they are bonded, and in that case, it represents a trivalent organic group having 2 to 12 total carbon atoms contained in $R^{117}$, $R^{118}$, and the carbon atoms to which these groups are bonded. $R^{119}$ represents a single bond or an alkylene group having 1 to 4 carbon atoms. $R^{120}$ may be the same or different, and represents a single bond, —O—, or —$CR^{114}R^{114}$—. $R^{121}$ represents a linear or a branched alkylene group having 1 to 4 carbon atoms and may be bonded with $R^{115}$ in the same monomer to form a non-aromatic ring having 3 to 6 carbon atoms together with the carbon atoms to which they are bonded. $R^{122}$ represents a 1,2-ethylene group, a 1,3-propylene group, or a 1,4-butylene group. Rf represents a linear perfluoroalkyl group having 3 to 6 carbon atoms, or a 3H-perfluoropropyl group, a 4H-perfluorobutyl group, 5H-perfluoropentyl group, or a 6H-perfluorohexyl group. Each $X^2$ may be the same or different and represents —C(=O)—O—, —O—, or —C(=O)—$R^{123}$—C(=O)—O—. $R^{123}$ represents a linear, a branched, or a cyclic alkylene group having 1 to 10 carbon atoms. Further, the other symbols satisfy the following relationships; $0 \leq (a'-1) < 1$, $0 \leq (a'-2) < 1$, $0 \leq (a'-3) < 1$, $0 < (a'-1)+(a'-2)+(a'-3) < 1$, $0 \leq b' < 1$, $0 \leq c' < 1$, and $0 < (a'-1)+(a'-2)+(a'-3)+b'+c' \leq 1$.)

The adding amount of the polymer-type surfactant is 0.001 to 20 parts by mass, or preferably 0.01 to 10 parts by mass, relative to 100 parts by mass of the base resin of the resist composition. These are elaborated in Japanese Patent Application Laid-Open No. 2007-297590.

When the resist composition of the present invention is used for a chemically amplified negative resist composition, a repeating unit having a crosslinkable substituent by an acid crosslinker is necessary. More specific examples of it include the repeating unit derived from acrylic acid, methacrylic acid, hydroxy styrene (position of substitution is arbitrary), and hydroxy vinylnaphthalene (position of substitution is arbitrary), though it is not limited to them.

In addition, an alkaline-soluble resin other than the polymers may be added.

Examples of the resin include poly(p-hydroxystyrene), poly(m-hydroxystyrene), poly(4-hydroxy-2-methylstyrene), poly(4-hydroxy-3-methylstyrene), poly(α-methyl-p-hydroxystyrene), partially hydrogenated poly(p-hydroxystyrene) copolymer, poly(p-hydroxystyrene-α-methyl-p-hydroxystyrene) copolymer, poly(p-hydroxystyrene-α-methylstyrene) copolymer, poly(p-hydroxystyrene-styrene) copolymer, poly(p-hydroxystyrene-m-hydroxystyrene) copolymer, poly(p-hydroxystyrene-styrene) copolymer, poly(p-hydroxystyrene-acrylic acid) copolymer, poly(p-hydroxystyrene-methacrylic acid) copolymer, poly(p-hydroxystyrene-methyl acrylate) copolymer, poly(p-hydroxystyrene-acrylic acid-methyl methacrylate) copolymer, poly(p-hydroxystyrene-methyl acrylate) copolymer, poly(p-hydroxystyrene-methacrylic acid-methyl methacrylate) copolymer, polymethacrylic acid, polyacylic acid, poly(acrylic acid-methyl acrylate) copolymer, poly(methacrylic acid-methyl methacrylate) copolymer, poly(acrylic acid-maleimide) copolymer, poly(methacrylic acid-maleimide) copolymer, poly(p-hydroxystyrene-acrylic acid-maleimide) copolymer, and poly(p-hydroxystyrene-methacrylic acid-maleimide) copolymer, but it is not limited to these combinations.

The blending ratio of the polymer to the other alkaline-soluble resin is preferably in the range of 100:0 to 10:90, in particular 100:0 to 20:80. When the blending ratio of the polymer is below this range, there is a case that suitable performance as the resist composition is not obtained. By appropriately changing the blending ratio, performance of the resist composition may be controlled.

Meanwhile, the alkaline-soluble resin can be added not only singly but also as a mixture of two or more kinds. By using a plurality of the polymers, performance of the resist composition can be controlled.

The acid crosslinker in the component (F) that forms a crosslinking structure by action of an acid includes a compound having two or more of a hydroxymethyl group, an alkoxymethyl group, an epoxy group, or a vinyl ether group in the molecule. A substituted glycouril derivative, a urea derivative, hexa(methoxymethyl)melamine, and the like can be suitably used as the acid crosslinker of the chemically amplified negative resist composition of the present invention. Examples of the crosslinker include N,N,N',N'-tetramethoxymethyl urea, hexamethoxymethyl melamine, tetrahydroxymethyl-substituted glycolurils, tetraalkoxymethyl-substituted glycolurils such as tetramethoxymethyl glycoluril, substituted or unsubstituted bis-hydroxymethyl phenols, and a condensate of a phenolic compound such as bisphenol A and epichlorohydrin and the like. Particularly preferable crosslinkers include 1,3,5,7-tetraalkoxymethyl glycoluril such as 1,3,5,7-tetramethoxymethyl glycoluril, tetrahydroxymethyl glycoluril, 2,6-dihydroxymethyl-p-cresol, 2,6-dihydroxymethyl phenol, 2,2',6,6'-tetrandyroxymethyl-bisphenol A, 1,4-bis[2-(2-hydroxypropyl)]-benzene, N,N,N', N'-tetramethoxymethyl urea, and hexamethoxymethyl melamine.

The adding amount of the acid crosslinker of the component (F) in the chemically amplified resist composition of the present invention is, though arbitrary, 1 to 20 parts by mass, or preferably 5 to 15 parts by mass, relative to 100 parts by mass of a base resin in the resist composition. These crosslinkers may be used singly or in a combination of two or more kinds.

The basic components in the resist composition of the present invention are the polymer described above (base resin), an acid generator, and an organic solvent, while a quencher may be added as appropriate. In addition to the components, other components such as a surfactant, a crosslinker, a dissolution inhibitor, an acidic compound, a stabilizer, and pigments may also be added as the arbitrary components. Here, the adding amount of these arbitrary components is usual in the range not impairing the effects of the present invention.

Patterning by using the resist composition of the present invention may be carried out with a heretofore known lithography technology. For example, coating is done on a substrate for integrated circuit manufacturing (Si, $SiO_2$, SiN, SiON, TiN, WSi, BPSG, SOG, an organic anti-reflection film, and the like) or on a substrate for mask circuit manufacturing (Cr, CrO, CrON, MoSi, and the like) by a technique such as spin-coating to make the film thickness of 0.05 to 2.0 μm, and then a pre-bake is done on a hot plate at 60 to 150° C. and for 1 to 20 minutes, or preferably at 80 to 140° C. and for 1 to 10 minutes. After that, a high energy beam such as a far-ultraviolet beam, an excimer laser, and an X-ray, or an electron beam is irradiated onto a mask that covers the substrate to form an intended pattern. Alternatively, an electron beam is directly irradiated for drawing without via the mask for patterning. The exposure dose is 1 to 200 $mJ/cm^2$, or preferably about 10 $mJ/cm^2$ to about 100 $mJ/cm^2$ in the case of the light exposure, and is about 0.1 $\mu C/cm^2$ to about 20 $\mu C/cm^2$, or preferably about 3 $\mu C/cm^2$ to about 10 $\mu C/cm^2$ in the case of the electron beam exposure. Exposure is done by a usual exposure method, and as appropriate, an immersion method wherein the space between a mask and a resist is immersed in a liquid can also be used. In that case, a top coat not soluble in water can also be used. After that, a post-exposure bake (PEB) is done on a hot plate at 60 to 150° C. and for 1 to 20 minutes, or preferably at 80 to 140° C. and for 1 to 10 minutes. Further, development is done by using a developer of an alkaline aqueous solution such as tetramethyl ammonium hydroxide (TMAH) with a concentration of 0.1 to 5% by mass, or preferably 2 to 3% by mass, for 0.1 to 3 minutes, or preferably 0.5 to 2 minutes by a usual method such as a dip method, a puddle method, and a spray method to form an intended pattern on the substrate. Meanwhile, the resist composition of the present invention is most suitable, in particular, for fine patterning by a far-ultraviolet beam or an excimer laser with 190 to 250 nm wavelength, an X-ray, and an electron beam, among the high energy beams.

The water-insoluble top coat is used to prohibit dissolution from a resist film and to improve water-repellent properties on the film surface. It can be classified into two types; one is the type in which delamination by an organic solvent not dissolvable a resist film is necessary before the alkaline development, and the other is the alkaline-soluble type in which the top coat is removed together with a resist part dissolvable in an alkaline developer.

In the latter case, in particular, a composition, containing as a base a polymer having a 1,1,1,3,3,3-hexafluoro-2-propanol moiety that is insoluble in water and soluble in an alkaline developer and dissolved in an alcoholic solvent having 4 or more carbon atoms, an ether solvent having 8 to 12 carbon atoms, or a mixture thereof, is preferable.

A composition may also be made by dissolving the surfactant that is insoluble in water and soluble in an alkaline developer into an alcoholic solvent having 4 or more carbon atoms, an ether solvent having 8 to 12 carbon atoms, or a mixture of them.

Further, as the means for the patterning, after formation of the photoresist film, an acid generator and the like may be extracted from the film surface or particles may be washed out by rinsing with pure water (post-soak), or rinsing may be done to remove the water remained on the film after exposure (post-soak).

In manufacturing a photomask by forming the resist pattern on a photomask blanks, especially when used for processing of the photomask blanks having a chromium material on the outermost surface, the resist pattern is not easily affected by the substrate dependency, and thus the patterning process of the present invention can be applied advantageously. Further, also when the resist pattern is formed on the material containing an oxygen-or nitrogen-containing silicone including a molybdenum-silicon compound, a high resolution and a temporal stability can be obtained, and thus a photomask with a high reliability can be manufactured.

The processing of a photomask blanks using a resist pattern as an etching mask may be made by any heretofore known method, but it is general that a chlorine-type dry etching containing an oxygen is done in the case that the outermost surface is made of a chromium compound, and a fluorine-type dry etching is done in the case that the outermost surface is made of a transition metal-silicon compound.

EXAMPLE

Hereinbelow, the present invention will be described specifically by Synthesis Examples, Examples, and Comparative Examples, but the present invention is not restricted by the following Examples.

Synthesis Example 1-1

Synthesis of Triphenylsulfonium Chloride

Diphenyl sulfoxide (40 g, 0.2 mole) was dissolved in 400 g of dichloromethane, and they were stirred under ice-cooling. Into it was added drop-wise 65 g (0.6 mole) of trimethylsilyl chloride at the temperature not exceeding 20° C., and at this temperature the resulted mixture was aged for 30 minutes. Then, a Grignard reagent, prepared separately from 14.6 g (0.6 mole) of a magnesium metal, 67.5 g (0.6 mole) of chlorobenzene, and 168 g of tetrahydrofurane (THF), was added drop-wise at the temperature not exceeding 20° C. After the reaction was aged for one hour, 50 g of water was added at the temperature not exceeding 20° C. to terminate the reaction, and further, 150 g of water, 10 g of 12-N hydrochloric acid, and 200 g of diethyl ether were added.

The resulted aqueous layer was separated and washed by 100 g of diethyl ether to obtain an aqueous solution of triphenylsulfonium chloride. This was used for the subsequent reaction as the aqueous solution without further isolation procedures.

Synthesis Example 1-2

Synthesis of 4-tert-Butylphenyl Diphenyl Sulfonium Bromide

The intended compound was obtained in a similar manner to that of Synthesis Example 1-1 except that 4-tert-butyl bromobenzene was used instead of chlorobenzene and the amount of water was increased at the time of extraction.

Synthesis Example 1-3

Synthesis of 4-tert-Butoxyphenyl Diphenyl Sulfonium Chloride

The intended compound was obtained in a similar manner to that of Synthesis Example 1-1 except that 4-tert-butoxy chlorobenzene was used instead of chlorobenzene, dichloromethane solvent which includes 5% by mass of triethylamine was used as a solvent, and the amount of water was increased at the time of extraction.

Synthesis Example 1-4

Synthesis of Tris(4-methylphenyl)Sulfonium Chloride

The intended compound was obtained in a similar manner to that of Synthesis Example 1-1 except that bis(4-methylphenyl)sulfoxide was used instead of diphenylsulfoxide, 4-chlorotoluene was used instead of chlorobenzene, and the amount of water was increased at the time of extraction.

Synthesis Example 1-5

Synthesis of Tris(4-tert-butylphenyl)Sulfonium Bromide

The intended compound was obtained in a similar manner to that of Synthesis Example 1-1 except that bis (4-tert-butylphenyl)sulfoxide was used instead of diphenylsulfoxide, 4-tert-butyl bromobenzene was used instead of chlorobenzene, and the amount of water was increased at the time of extraction.

Synthesis Example 1-6

Synthesis of Bis(4-tert-butylphenyl)Iodonium Hydrogen Sulfate

A mixture of 84 g (0.5 mole) of tert-butylbenzene, 53 g (0.25 mole) of potassium iodate, and 50 g of acetic anhydride was stirred under ice-cooling, and then a mixture of 35 g of acetic anhydride and 95 g of conc. sulfuric acid was added drop-wise into it at the temperature not exceeding 30° C. Then, after ageing at room temperature for 3 hours, the resulted mixture was ice-cooled again and then added by 250 g of water drop-wise to terminate the reaction. This reaction solution was extracted by 400 g of dichloromethane, and then the organic layer was decolorized by adding 6 g of sodium hydrogen sulfite. This organic layer was washed by 250 g of water for three times, and concentrated under reduced pressure to obtain the intended product. This was used in the subsequent reaction as it was without further purification.

Synthesis Example 1-7

Synthesis of Dimethylphenyl Sulfonium Sulfate

Thioanisol (6.2 g, 0.05 mole) and 6.9 g (0.055 mole) of dimethyl sulfuric acid were stirred at room temperature for 12 hours. Into the reaction solution were added 100 g of water and 50 mL of diethyl ether to separate the water layer to obtain the aqueous solution of the intended dimethylphenyl sulfonium sulfate.

Synthesis Example 1-8

Synthesis of Phenacyl Tetrahydrothiophenium Bromide

Phenacyl bromide (88.2 g, 0.44 mole) and 39.1 g (0.44 mole) of tetrahydrothiophene were dissolved in 220 g of nitromethane, and they were stirred at room temperature for 4 hours. Into the reaction solution were added 800 g of water and 400 g of diethyl ether, and the separated water layer was taken to obtain the aqueous solution of the intended phenacyl tetrahydrothiophenium bromide.

Synthesis Example 1-9

Synthesis of Triphenylsulfonium 3,3,3-Trifluoro-2-hydroxy-2-trifluoromethylpropane-1-sulfonate (PAG-1)

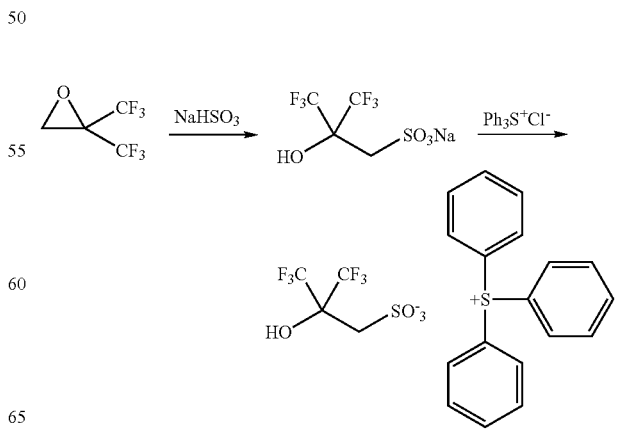

A mixed solution of 18.0 g (0.10 mole) of 2,2-bistrifluoromethyloxylane, 10.4 g (0.10 mole) of sodium hydrogen sulfite, 19.3 g of water, and 0.62 g of 25% sodium hydroxide was stirred at 40° C. for 10 hours to prepare sodium 3,3,3-trifluoro-2-hydroxy-2-trifluoromethylpropane-1-sulfonate. The obtained sodium sulfonate was used in the subsequent reaction without isolation. After sodium 3,3,3-trifluoro-2-hydroxy-2-trifluoromethylpropane-1-sulfonate was prepared, into it were added 290 g (0.10 mole) of the triphenylsulfonium chloride aqueous solution prepared by the method of Synthesis Example 1-1 and 500 g of methylene chloride, and the resulted mixture was stirred at room temperature for 4 hours. After the stirring, the organic layer was separated, washed by water, and then concentrated under reduced pressure. Into the condensed solution was added methyl isobutyl ketone and the resulted mixture was concentrated again under reduced pressure to distil the remaining water out. Into the obtained residue was added diisopropyl ether for recrystallization. The obtained crystals were recovered and dried to obtain the intended triphenylsulfonium 3,3,3-trifluoro-2-hydroxy-2-trifluoromethylpropane-1-sulfonate (40.8 g of white crystals (yield 78%)). The structure of the intended product is shown below.

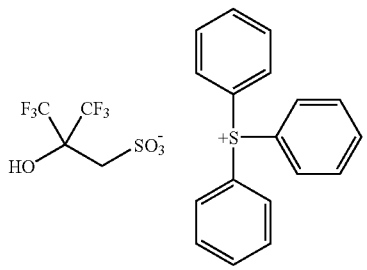

Figure 2:
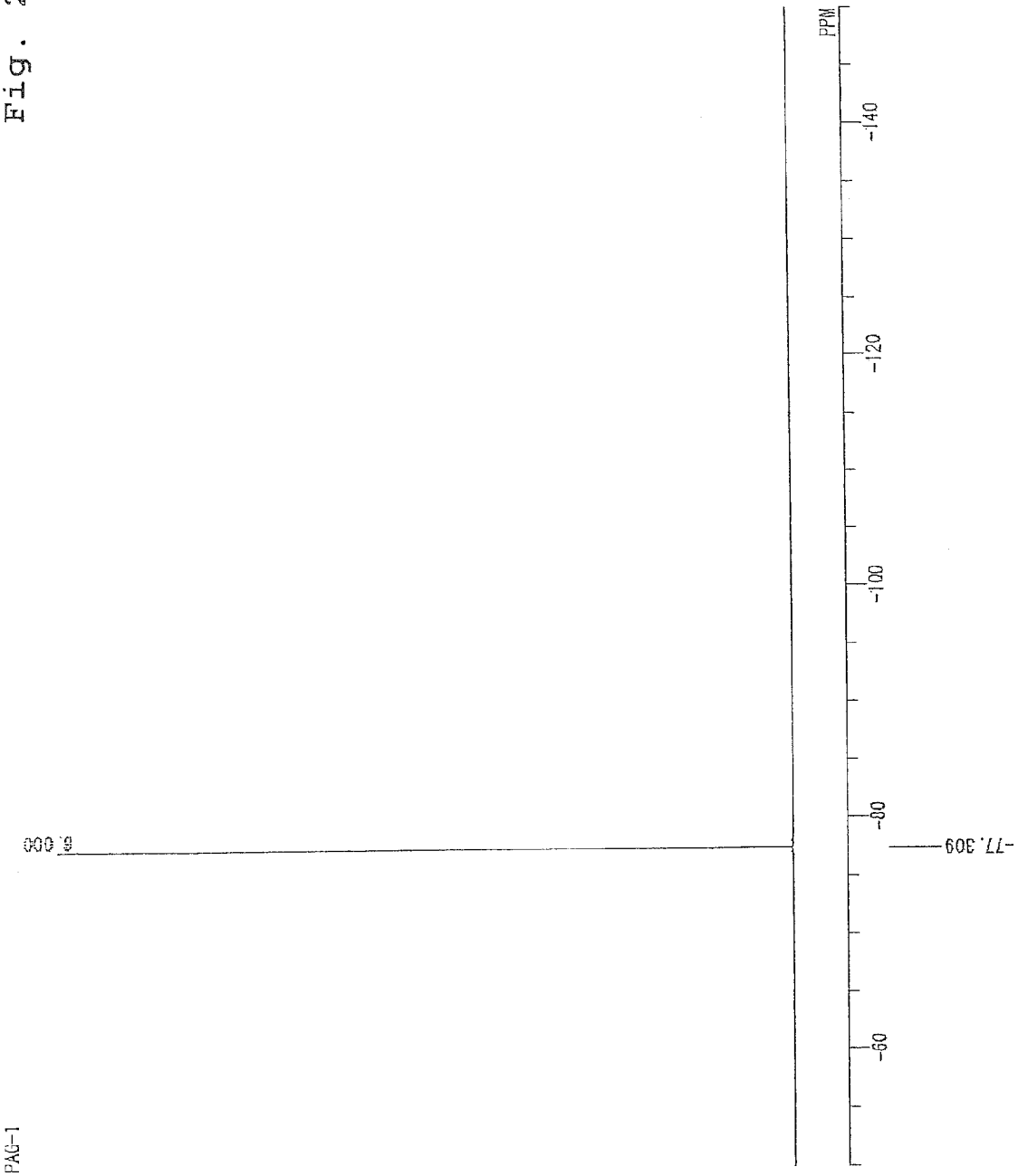
FIG. 2 is a spectrum of $^{19}$F-NMR/DMSO-$d_6$ of PAG-1 in synthesis example 1-9.

Spectrum data of the intended product thus obtained are shown as follows. Results of the nuclear magnetic resonance spectra ($^1$H-NMR, $^{19}$F-NMR/DMSO-$d_6$) are shown in FIG. 1 and FIG. 2, respectively. Meanwhile, trace amounts of residual solvents (diisopropyl ether and water) are detected in $^1$H-NMR.
IR Spectrum (IR(KBr); cm$^{-1}$):
3060, 1476, 1448, 1329, 1253, 1227, 1191, 1145, 1029, 1011, 968, 780, 760, 749, 685, and 497 cm$^{-1}$
Time-of-Flight Mass Spectrum Analysis (TOFMS; MALDI):
POSITIVE: M$^+$ 263 (corresponding to $(C_6H_5)_3S^+$)
NEGATIVE: M$^-$ 261 (corresponding to HO—C(CF$_3$)$_2$—CH$_2$SO$_3^-$)

The cationic species of PAG-1 was exchanged in a similar manner to that of Synthesis Example 1-9 except that the onium salts prepared according to Synthesis Examples 1-2 to 1-8 were used instead of triphenylsulfoniun chloride to synthesize each PAG-1 compound whose cationic species was exchanged to 4-tert-butylphenyl diphenyl sulfonium, 4-tert-butoxyphenyl diphenyl sulfonium, tris(4-methylphenyl)sulfonium, tris(4-tert-butylphenyl)sulfonium, bis(4-tert-butylphenyl)iodonium, dimethylphenyl sulfonium, and phenacyl tetrahydrothiophenium.

Synthesis Example 1-10

Synthesis of Triphenylsulfonium 2-(Adamantane-1-carbonyloxy)-3,3,3-trifluoro-2-trifluoromethylpropane-1-sulfonate (PAG-2)

Into a mixture solution of 5.2 g (10 mmoles) of triphenylsulfonium 3,3,3-trifluoro-2-hydroxy-2-trifluoromethylpropane-1-sulfonate prepared in Synthesis Example 1-9, 1.1 g (11 mmoles) of triethylamine, 0.24 g (2 mmoles) of 4-dimethylaminopyridine, and 21 g of methylene chloride was added 5.5 g (11 mmoles) of a methylene chloride solution of adamantane-1-carbonyl chloride (40% by weight), and they were stirred at room temperature for 2 hours. Thereafter, the reaction was terminated by adding 12 g of 5% hydrochloric acid, and then the organic layer was separated, washed by water, and concentrated under reduced pressure. Into the concentrated solution was added methyl isobutyl ketone, and the resulted mixture was concentrated again under reduced pressure to distil the remaining water out. The obtained residue was washed by diisopropyl ether, and then dried to obtain the intended triphenylsulfonium 2-(adamantane-1-carbonyloxy)-3,3,3-trifluoro-2-trifluoromethylpropane-1-sulfonate (2.7 g of oily substance (yield 39%)). The structure of the intended product is shown below.

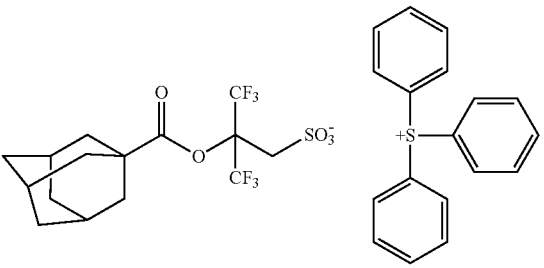

Figure 3:
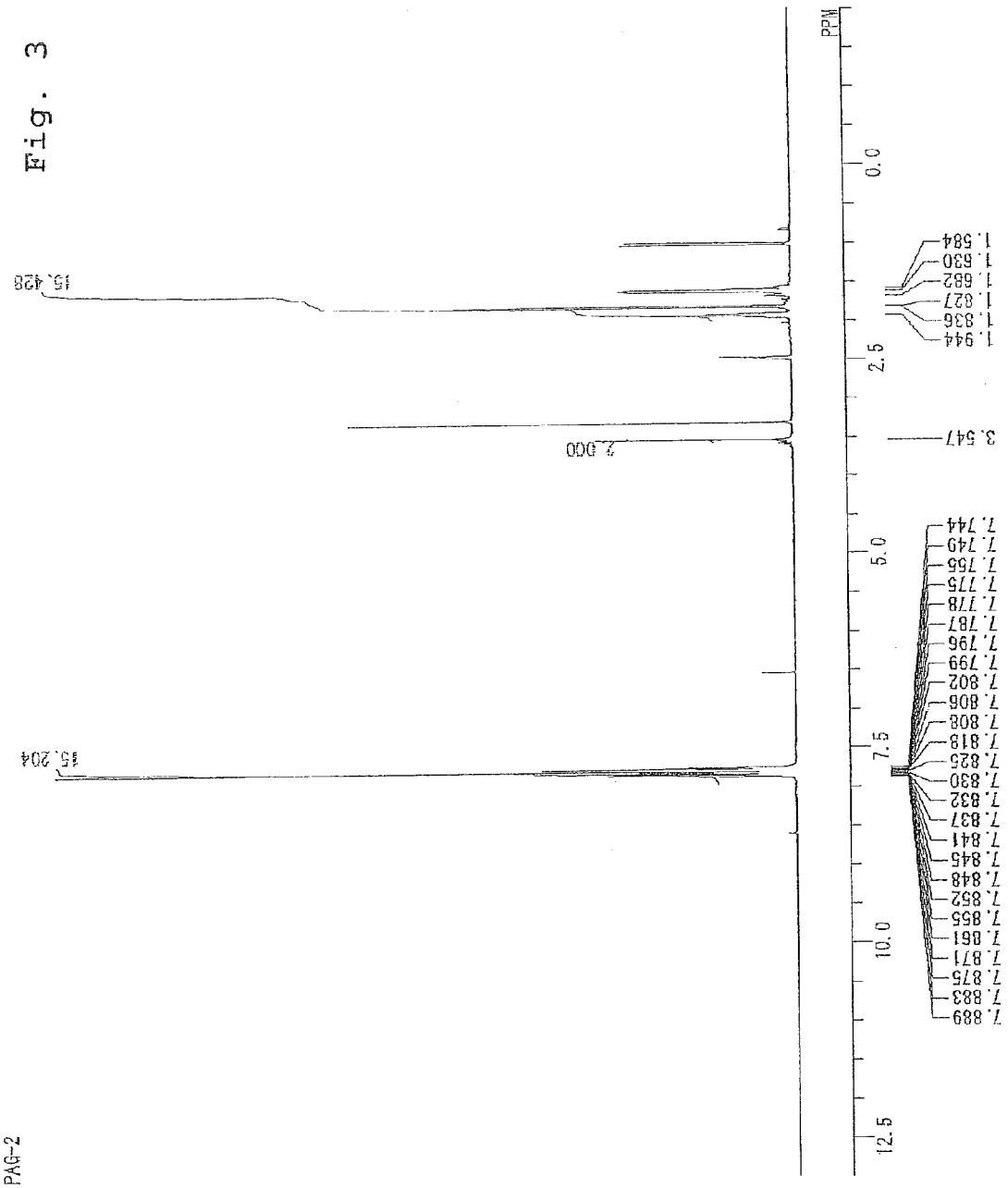
FIG. 3 is a spectrum of $^1$H-NMR/DMSO-$d_6$ of PAG-2 in Synthesis Example 1-10.
Figure 4:
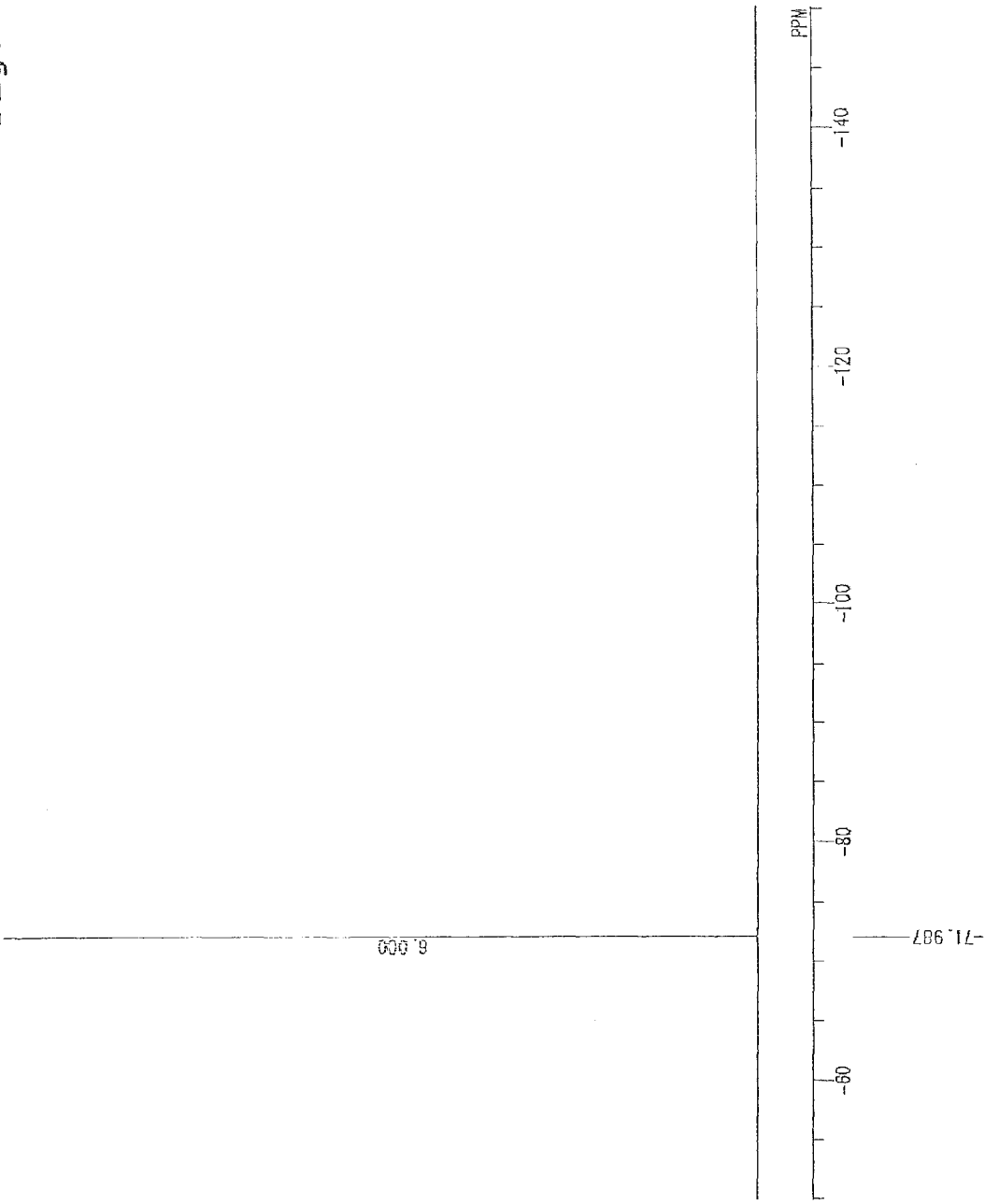
FIG. 4 is a spectrum of $^{19}$F-NMR/DMSO-$d_6$ of PAG-2 in synthesis example 1-10.

Spectrum data of the intended product thus obtained are shown as follows. Results of the nuclear magnetic resonance spectra ($^1$H-NMR, $^{19}$F-NMR/DMSO-$d_6$) are shown in FIG. 3 and FIG. 4, respectively. Meanwhile, trace amounts of residual solvents (diisopropyl ether and water) are detected in $^1$H-NMR.
IR Spectrum (IR(KBr); cm$^{-1}$):
3443, 2908, 2853, 1760, 1477, 1448, 1330, 1297, 1253, 1239, 1220, 1197, 1127, 1062, 1041, 1018, 969, 750, 684, 616, 595, 517, 501 cm$^{-1}$
Time-of-Flight Mass Spectrum Analysis (TOFMS; MALDI):
POSITIVE: M$^+$ 263 (corresponding to $(C_6H_5)_3S^+$)
NEGATIVE: M$^-$ 423 (corresponding to $(C_{10}H_{15}COO)$—C(CF$_3$)$_2$—CH$_2$SO$_3^-$))

By changing the cationic species of triphenylsulfonium 3,3,3-trifluoro-2-hydroxy-2-trifluoromethylpropane-1-sulfonate, the starting raw material, triphenylsulfonium 2-(adamantane-1-carbonyloxy)-3,3,3-trifluoro-2-trifluoromethylpropane-1-sulfonate having the changed cationic species can be synthesized in a similar manner in other procedures.

Synthesis Example 1-11

Synthesis of Triphenylsulfonium 2-(2,2-Dimethylpropionyloxy)-3,3,3-trifluoro-2-trifluoromethylpropane-1-sulfonate (PAG-3)

Into a mixture solution of 2.6 g (5 mmoles) of triphenylsulfonium 3,3,3-trifluoro-2-hydroxy-2-trifluoromethylpropane-1-sulfonate prepared in Synthesis Example 1-9, 0.63 g (6 mmoles) of triethylamine, 0.12 g (1 mmole) of 4-dimethylaminopyridine, and 15 g of methylene chloride was added 0.72 g (6 mmoles) of pivaloyl chloride, and they were stirred at room temperature for 8 hours. Thereafter, the reaction was terminated by adding 11 g of 5% hydrochloric acid, and then the organic layer was separated, washed by water, and concentrated under reduced pressure. Into the concentrated solution was added a mixture solution of methyl isobutyl ketone and methylene chloride, and the resulted mixture was concentrated again under reduced pressure to distil the remaining water out. The obtained residue was recrystallized by adding diisopropyl ether, and then the crystals were recovered and dried to obtain the intended triphenylsulfonium 2-(2,2-dimethylpropionyloxy)-3,3,3-trifluoro-2-trifluoromethylpropane-1-sulfonate (1.8 g of white crystals (yield 58%)). The structure of the intended product is shown below.

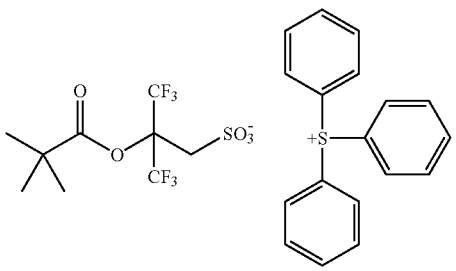

Figure 5:
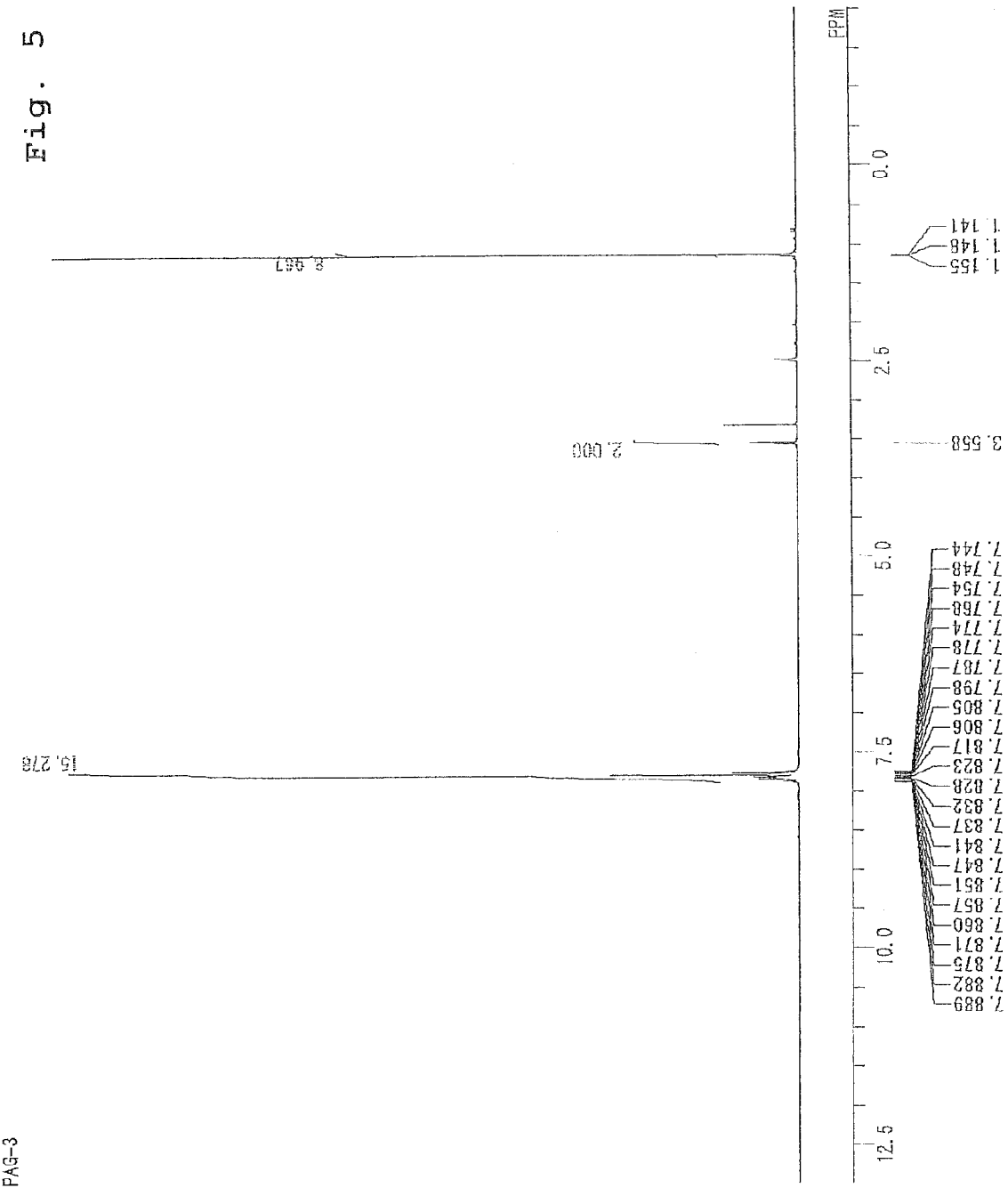
FIG. 5 is a spectrum of $^1$H-NMR/DMSO-$d_6$ of PAG-3 in Synthesis Example 1-11.
Figure 6:
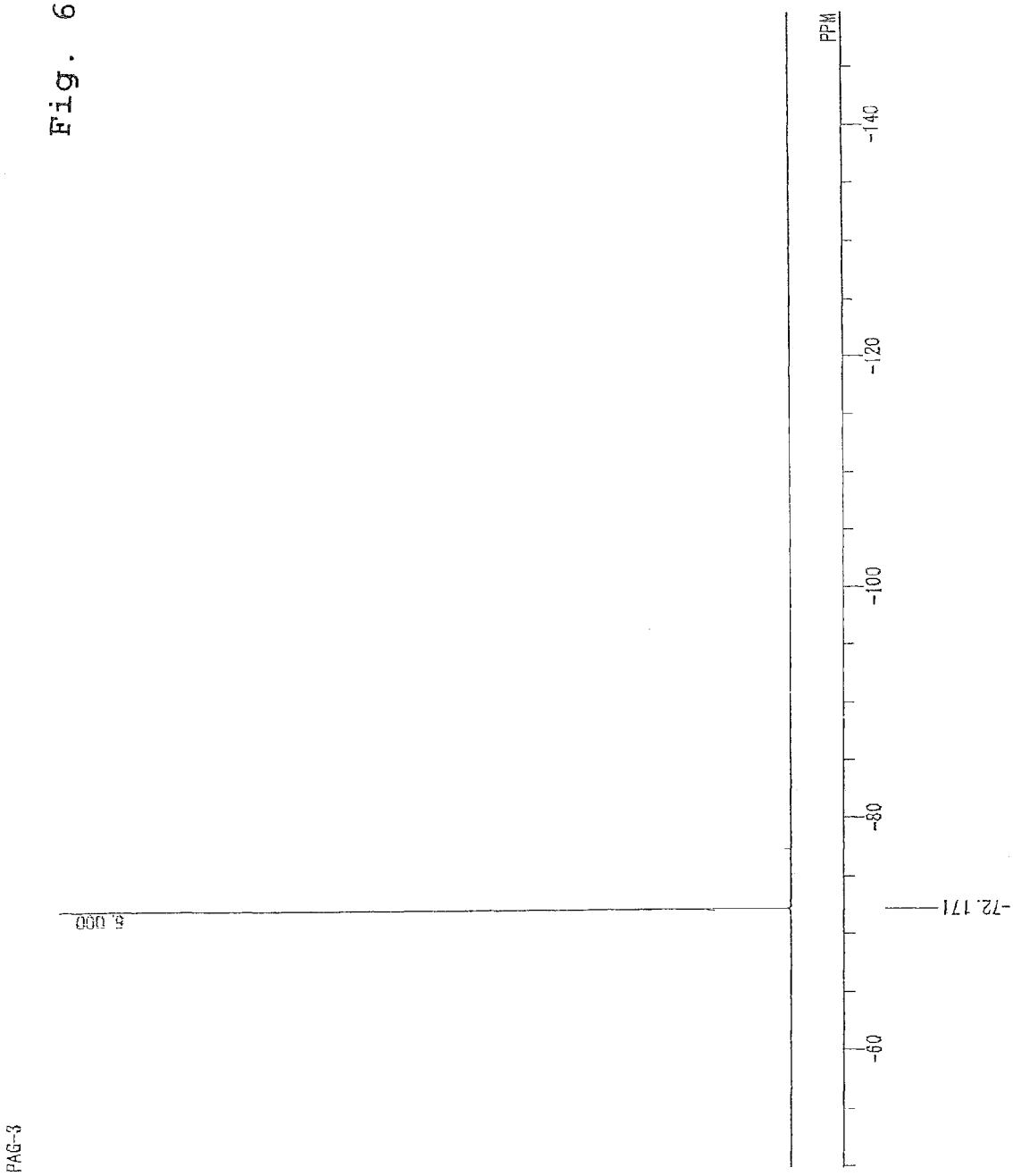
FIG. 6 is a spectrum of $^{19}$F-NMR/DMSO-$d_6$ of PAG-3, in synthesis example 1-11.

Spectrum data of the intended product thus obtained are shown as follows. Results of the nuclear magnetic resonance spectra ($^1$H-NMR, $^{19}$F-NMR/DMSO-$d_6$) are shown in FIG. 5 and FIG. 6, respectively. Meanwhile, trace amounts of residual water is detected in $^1$H-NMR.
IR Spectrum (IR(KBr); cm$^{-1}$):
3059, 2970, 1758, 1477, 1446, 1330, 1245, 1217, 1200, 1131, 1115, 1042, 1025, 971, 764, 748, 682, 620, 598, 505 cm$^{-1}$
Time-of-Flight Mass Spectrum Analysis (TOFMS; MALDI):
POSITIVE: M$^+$ 263 (corresponding to $(C_6H_5)_3S^+$)
NEGATIVE: M$^-$ 345 (corresponding to $(C_4H_9COO)$—C$(CF_3)_2$—$CH_2SO_3^-$))

By changing the cationic species of triphenylsulfonium 3,3,3-trifluoro-2-hydroxy-2-trifluoromethylpropane-1-sulfonate, the starting raw material, triphenylsulfonium 2-(2,2-dimethylpropionyloxy)-3,3,3-trifluoro-2-trifluoromethylpropane-1-sulfonate having the changed cationic species can be synthesized in a similar manner in other procedures.

Synthesis Example 1-12

Synthesis of Triphenylsulfonium 2-(2-Adamantane-1-yl-acetoxy)-3,3,3-trifluoro-2-trifluoromethylpropane-1-sulfonate (PAG-4)

Into a mixture solution of 2.6 g (5 mmoles) of triphenylsulfonium 3,3,3-trifluoro-2-hydroxy-2-trifluoromethylpropane-1-sulfonate prepared in Synthesis Example 1-9, 1.3 g (6 mmoles) of 1-adamantaneacetyl chloride, and 15 g of methylene chloride was added a mixture solution of 0.63 g (6 mmoles) of triethylamine, 0.12 g (1 mmole) of 4-dimethylaminopyridine, and 5 g of methylene chloride, and they were stirred at room temperature for 5 days. Thereafter, the reaction was terminated by adding 7 g of 5% hydrochloric acid, and then the organic layer was separated, washed by water, and concentrated under reduced pressure. Into the concentrated solution was added methyl isobutyl ketone, and the resulted mixture was concentrated again under reduced pressure to distil the remaining water out. The obtained residue was recrystallized by adding diisopropyl ether, and then the crystals were recovered and dried to obtain the intended triphenylsulfonium 2-(2-adamantane-1-yl-acetoxy)-3,3,3-trifluoro-2-trifluoromethylpropane-1-sulfonate (1.7 g of white crystals (yield 48%)). The structure of the intended product is shown below.

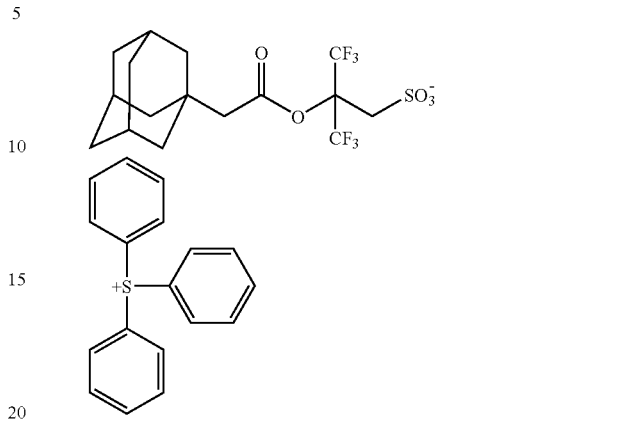

Figure 7:
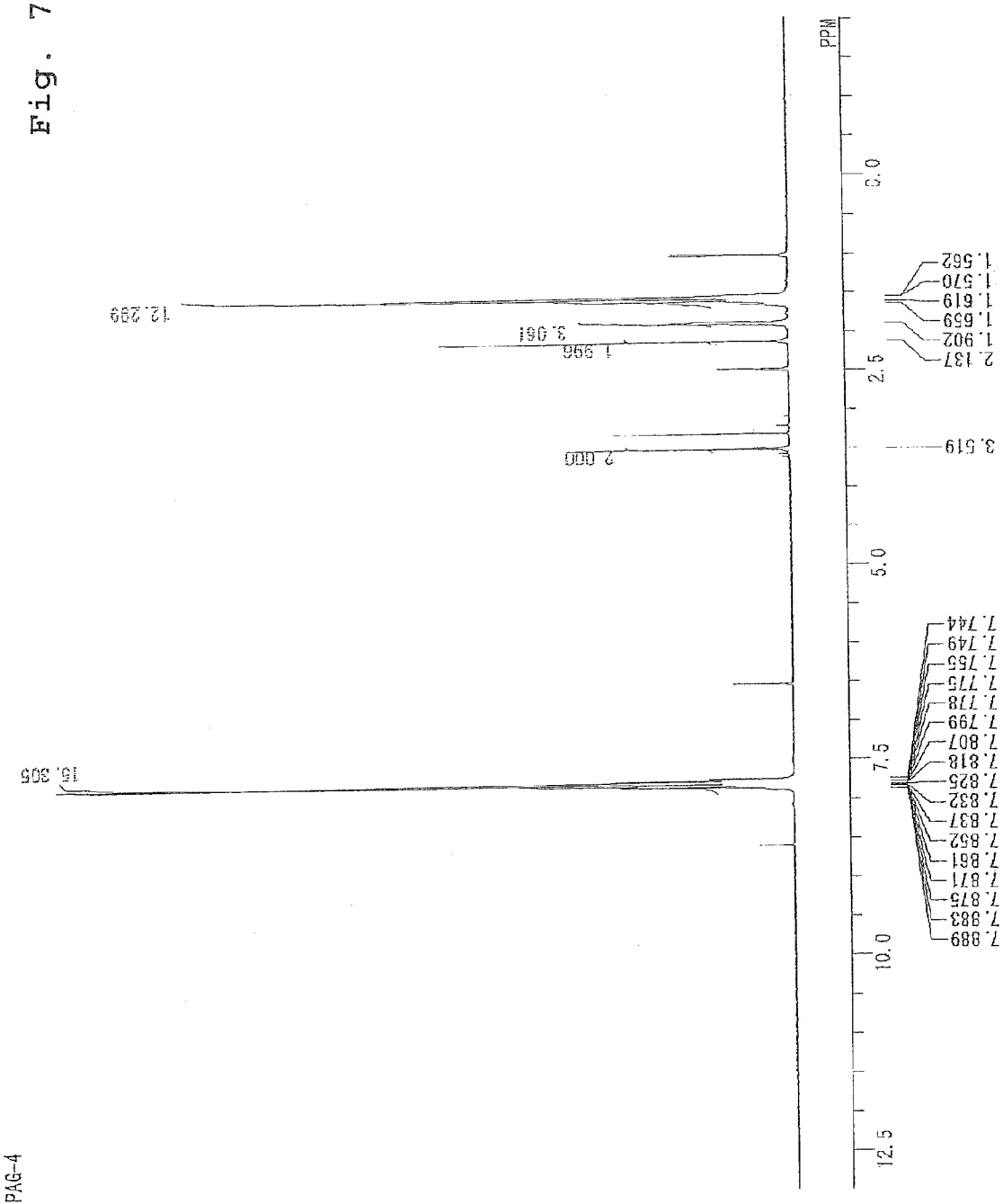
FIG. 7 is a spectrum of $^1$H-NMR/DMSO-$d_6$ of PAG-4 in Synthesis Example 1-12.
Figure 8:
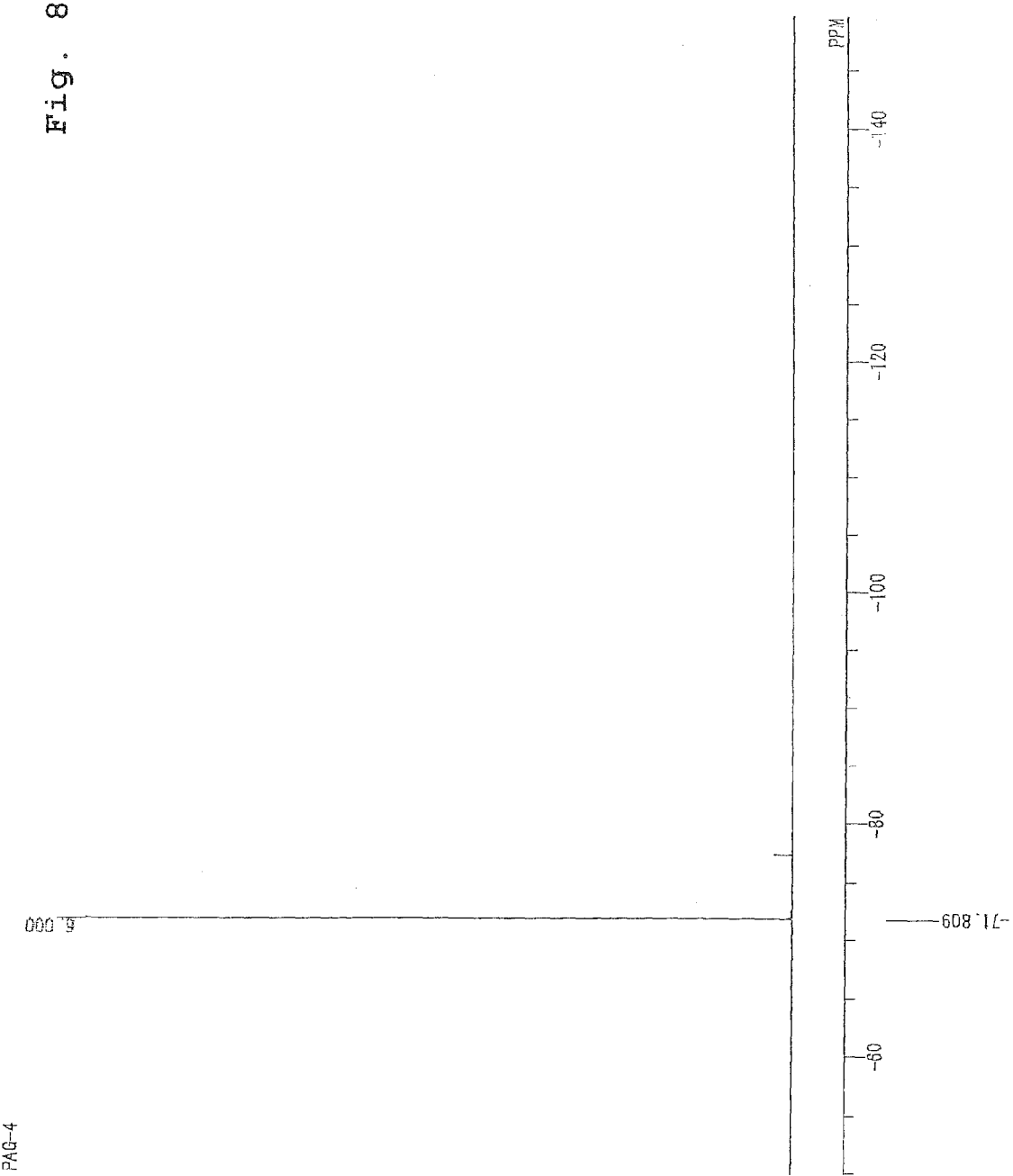
FIG. 8 is a spectrum of $^{19}$F-NMR/DMSO-$d_6$ of PAG-4 in synthesis example 1-12.

Spectrum data of the intended product thus obtained are shown as follows. Results of the nuclear magnetic resonance spectra ($^1$H-NMR, $^{19}$F-NMR/DMSO-$d_6$) are shown in FIG. 7 and FIG. 8, respectively. Meanwhile, trace amounts of residual solvents (diisopropyl ether and water) are detected in $^1$H-NMR.
IR Spectrum (IR(KBr); cm$^{-1}$):
3441, 2905, 2850, 1767, 1448, 1329, 1256, 1239, 1214, 1200, 1121, 1097, 1043, 970, 750, 682, 601, 512, 503 cm$^{-1}$
Time-of-Flight Mass Spectrum Analysis (TOFMS; MALDI):
POSITIVE: M$^+$ 263 (corresponding to $(C_6H_5)_3S^+$)
NEGATIVE: M$^-$ 437 (corresponding to $(C_{11}H_{17}COO)$—C$(CF_3)_2$—$CH_2SO_3^-$))

By changing the cationic species of triphenylsulfonium 3,3,3-trifluoro-2-hydroxy-2-trifluoromethylpropane-1-sulfonate, the starting raw material, triphenylsulfonium 2-(2-adamantane-1-yl-acetoxy)-3,3,3-trifluoro-2-trifluoromethylpropane-1-sulfonate having the changed cationic species can be synthesized in a similar manner in other procedures.

In addition to the above, the acid generator obtained according to the present invention may be exemplified by, for example, those shown in following Synthesis Examples 1-13 and 1-14.

Synthesis Example 1-13

Synthesis of Bis(4-tert-butylphenyl)iodonium 3,3,3-Trifluoro-2-hydroxy-2-trifluoromethylpropane-1-sulfonate (PAG-5)

Bis(4-tert-butylphenyl)iodonium hydrogen sulfate (0.02 mole equivalent) prepared in Synthesis Example 1-6, 0.024 mole equivalent of the aqueous solution of sodium 3,3,3-trifluoro-2-hydroxy-2-trifluoromethylpropane-1-sulfonate prepared in Synthesis Example 1-9, and 70 g of methylene chloride were mixed and agitated at room temperature for 1 hour. After the agitation, the organic layer was separated, washed by water, and then concentrated under reduced pressure. The residue was recrystallized by adding diisopropyl ether, and then the obtained crystals were recovered and dried to obtain the intended bis(4-tert-butylphenyl)iodonium 3,3,3-trifluoro-2-hydroxy-2-trifluoromethylpropane-1-sulfonate (9.4 g of white crystals (yield 72%)). The structure of the intended product is shown below.

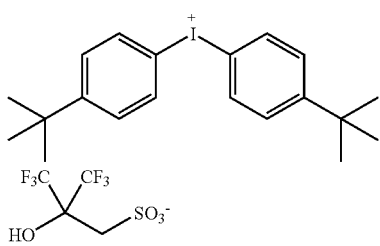

Figure 9:
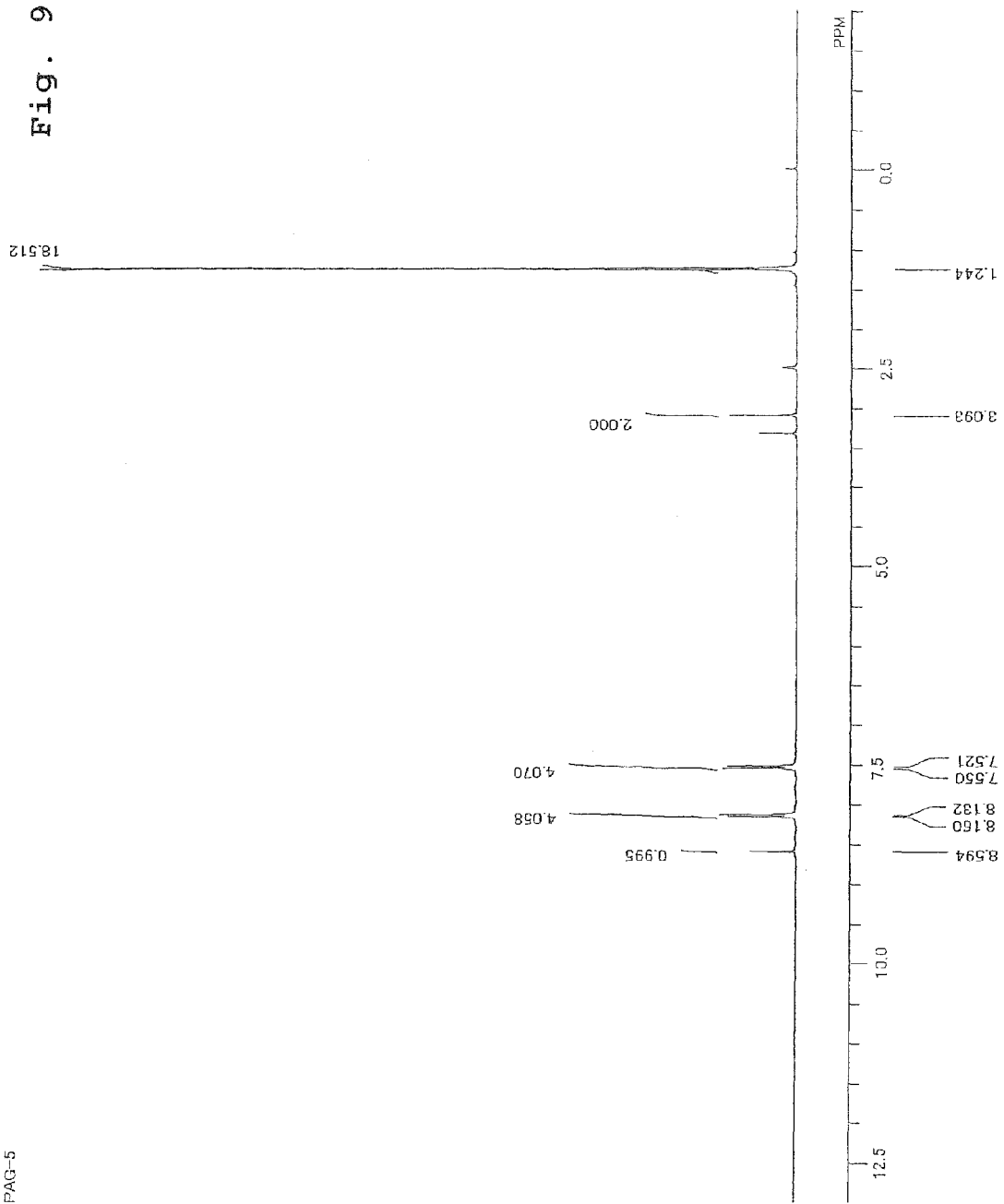
FIG. 9 is a spectrum of $^1$H-NMR/DMSO-$d_6$ of PAG-5 in Synthesis Example 1-13.
Figure 10:
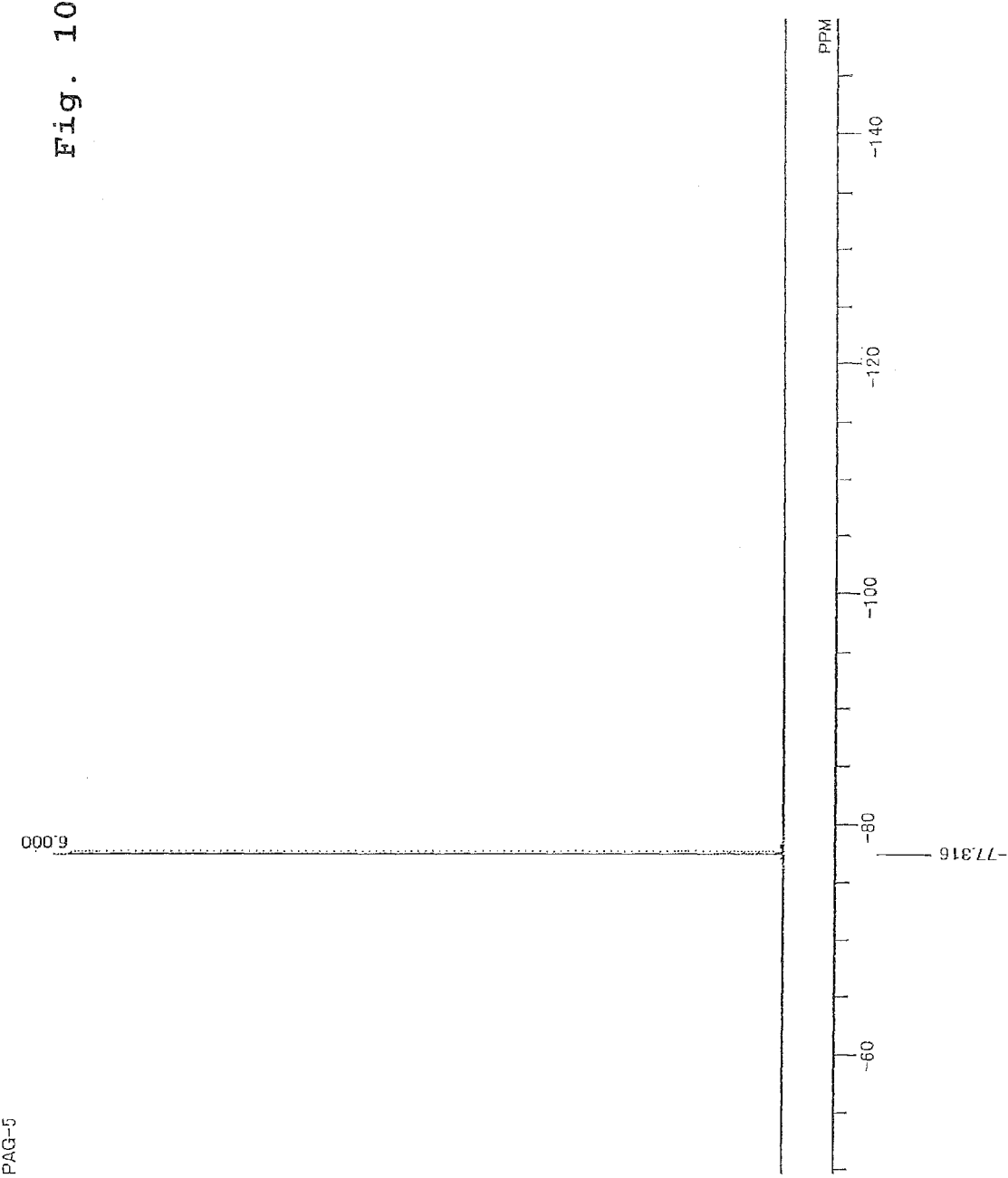
FIG. 10 is a spectrum of $^{19}$F-NMR/DMSO-$d_6$ of PAG-5 in synthesis example 1-13.

Spectrum data of the intended product thus obtained are shown as follows. Results of the nuclear magnetic resonance spectra ($^1$H-NMR, $^{19}$F-NMR/DMSO-d$_6$) are shown in FIG. 9 and FIG. 10, respectively. Meanwhile, trace amounts of water is detected in $^1$H-NMR.

IR Spectrum (IR(D-ATR); cm$^{-1}$):
2967, 1481, 1396, 1329, 1261, 1219, 1188, 1147, 1106, 1037, 1027, 1012, 994, 964, 818, 601 cm$^{-1}$
Time-of-Flight Mass Spectrum Analysis (TOFMS; MALDI):
POSITIVE: M$^+$ 393 (corresponding to (C$_{20}$H$_{26}$)$_2$I$^+$)
NEGATIVE: M$^-$ 261 (corresponding to (HO—C(CF$_3$)$_2$—CH$_2$SO$_3^-$))

Synthesis Example 1-14

Synthesis of Bis(4-tert-butylphenyl)iodonium 2-(2,2-Dimethylpropionyloxy)-3,3,3-trifluoro-2-trifluoromethylpropane-1-sulfonate (PAG-6)

Into a mixture solution of 6.5 g (0.010 mole) of bis(4-tert-butylphenyl)iodonium 3,3,3-trifluoro-2-hydroxy-2-trifluoromethylpropane-1-sulfonate prepared in Synthesis Example 1-13, 2.2 g (0.022 mole) of triethylamine, 0.2 g (0.002 mole) of 4-dimethylaminopyridine, and 25 g of methylene chloride was added 2.4 g (0.020 mole) of pivaloyl chloride, and they were stirred at room temperature for 8 hours. Thereafter, the reaction was terminated by adding 22 g of 5% hydrochloric acid, and then the organic layer was separated, washed by water, and concentrated under reduced pressure. Into the concentrated solution was added methyl isobutyl ketone, and the resulted mixture was concentrated again under reduced pressure to distil the remaining water out. The obtained residue was recrystallized by adding diisopropyl ether, and then the crystals were recovered and dried to obtain the intended bis (4-tert-butylphenyl)iodonium 2-(2,2-Dimethylpropionyloxy)-3,3,3-trifluoro-2-trifluoromethylpropane-1-sulfonate (1.8 g of white crystals (yield 23%)). The structure of the intended product is shown below.

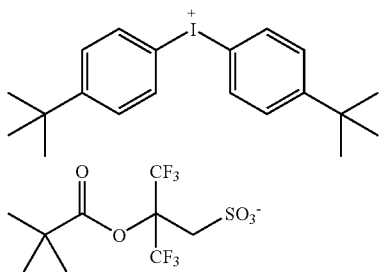

Figure 11:
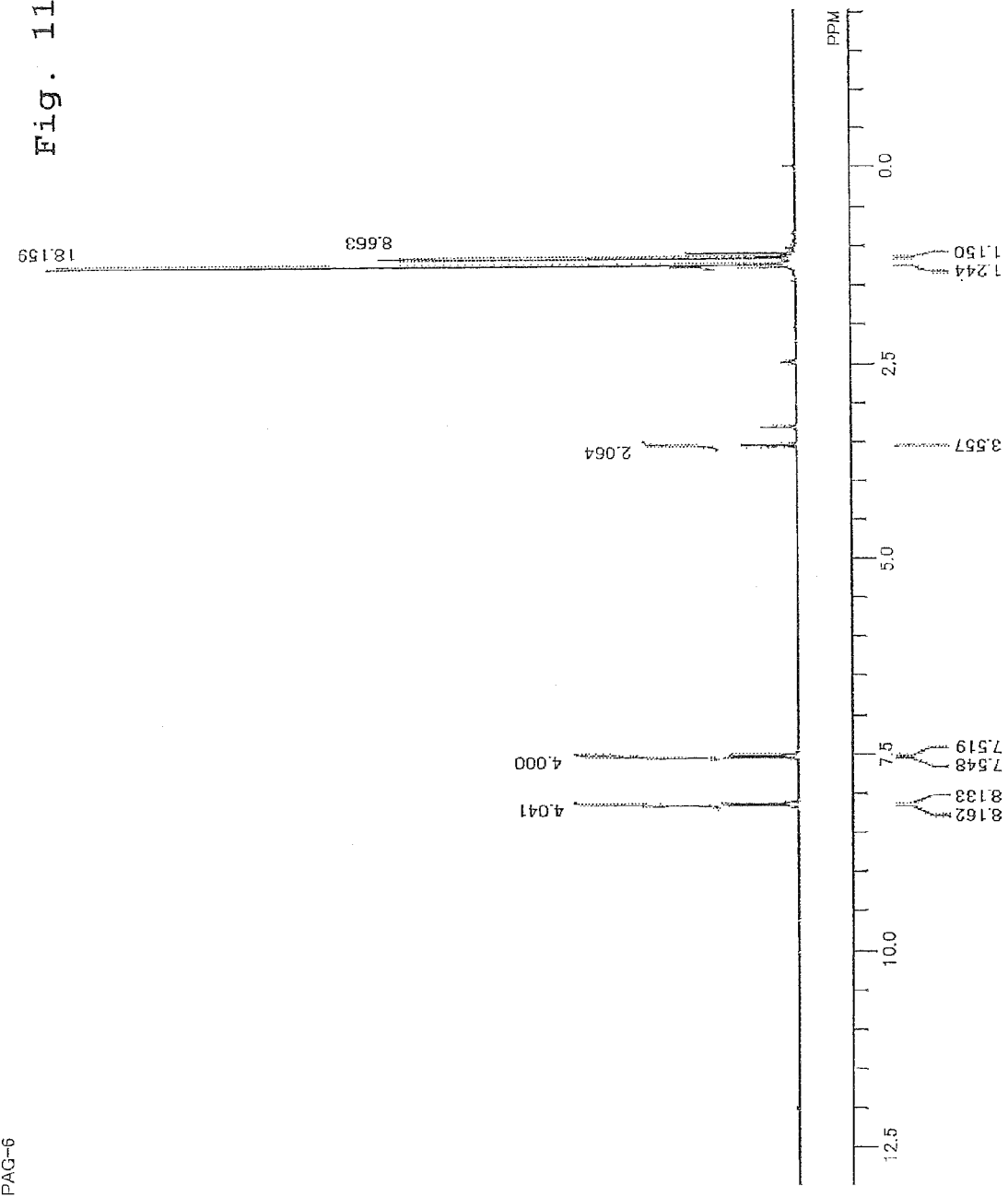
FIG. 11 is a spectrum of $^1$H-NMR/DMSO-$d_6$ of PAG-6 in Synthesis Example 1-14.
Figure 12:
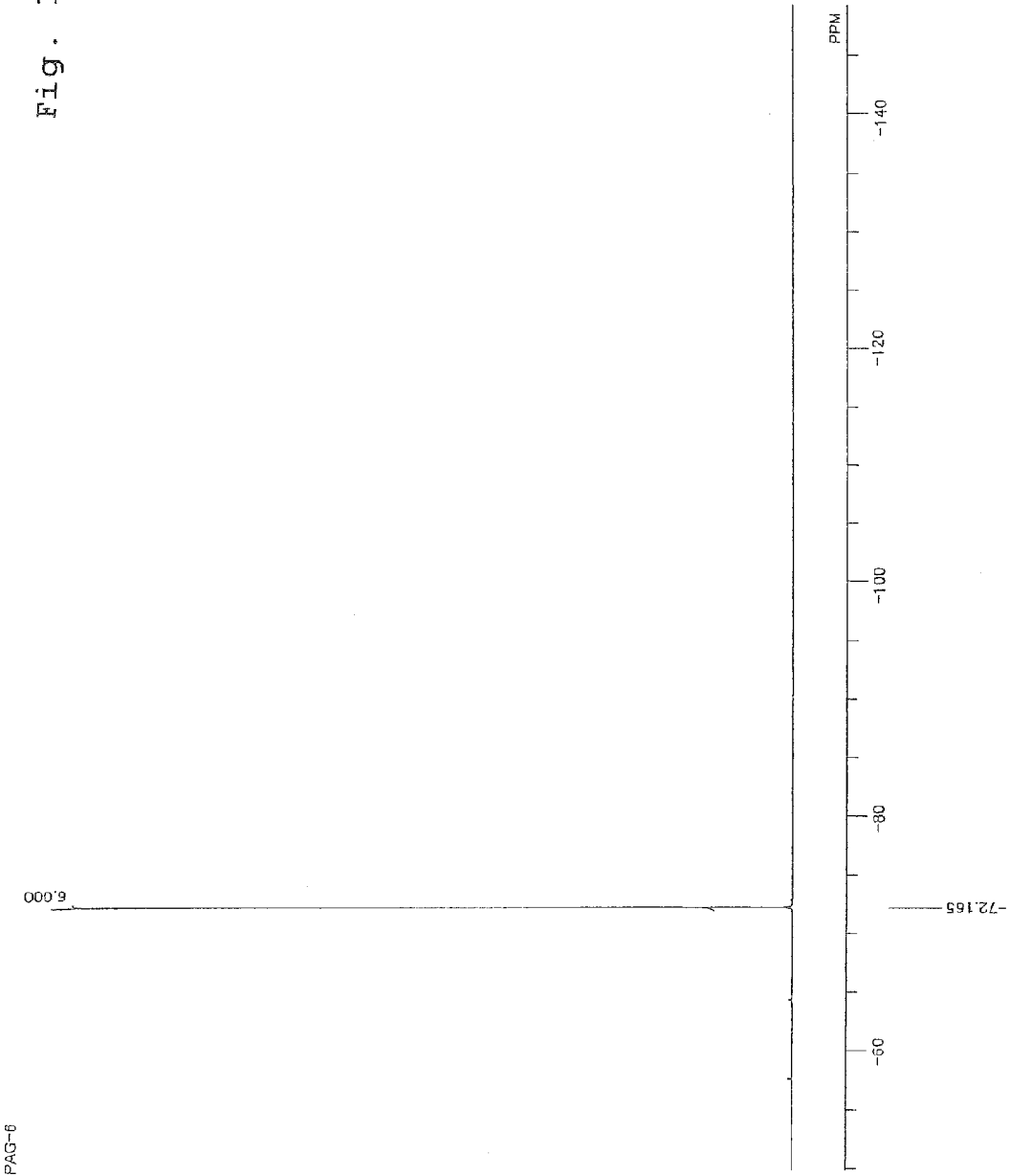
FIG. 12 is a spectrum of $^{19}$F-NMR/DMSO-$d_6$ of PAG-6 in synthesis example 1-14.

Spectrum data of the intended product thus obtained are shown as follows. Results of the nuclear magnetic resonance spectra ($^1$H-NMR, $^{19}$F-NMR/DMSO-d$_6$) are shown in FIG. 11 and FIG. 12, respectively. Meanwhile, trace amounts of water and pivalinic acid are detected in $^1$H-NMR.

IR Spectrum (IR(D-ATR); cm$^{-1}$):
2968, 1765, 1721, 1482, 1397, 1329, 1238, 1200, 1156, 1147, 1131, 1113, 1033, 1024, 994, 972, 827, 618, 596, 584 cm$^{-1}$
Time-of-Flight Mass Spectrum Analysis (TOFMS; MALDI):
POSITIVE: M$^+$ 393 (corresponding to (C$_{20}$H$_{26}$)$_2$I$^+$)
NEGATIVE: M$^-$ 345 (corresponding to (C$_4$H$_9$COO)—C(CF$_3$)$_2$—CH$_2$SO$_3^-$)

Polymers used as the base resin of the present invention were synthesized according to the following prescriptions.

Synthesis Example 2-1

Synthesis of Polymer 1

Under a nitrogen atmosphere, 114 g of acetoxy styrene, 11.7 g of indene, 38.5 g of ethoxyethoxy styrene, and 8.2 g of 2,2'-azobisisobutyronitrile were dissolved in 550 g of toluene, and the solution thus prepared was stirred under a nitrogen atmosphere at 50° C. for 50 hours. After cooled to a room temperature, 475 g of methanol and 75 g of water were added to the polymer solution, and then the lower layer of the separated solution in the lower layer was taken and concentrated under reduced pressure. The concentrated solution thus obtained was used as it was in the subsequent hydrolysis reaction.

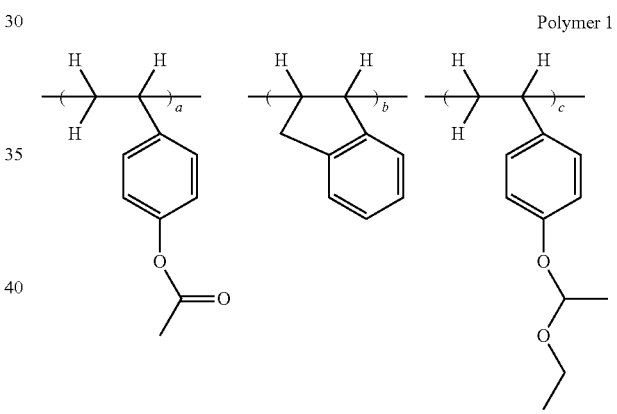

Polymer 1

$a = 0.70, b = 0.10, c = 0.20$

Synthesis Examples 2-2 to 2-11

Synthesis of Polymers 2 to 11

Polymers 2 to 11 were synthesized in a similar manner to that of Synthesis Example 2-1 except that each monomer and their blending ratios were changed.

Synthesis Example 2-12

Synthesis of Polymer 12

Into the concentrated solution containing Polymer 1 prepared as mentioned above were added 290 g of tetrahydrofurane, 260 g of methanol, 90 g of triethylamine, and 18 g of water, and the resulted mixture was stirred at 60° C. for 40 hours. Thereafter, the reaction solution was concentrated, and then 290 g of methanol, 60 g of acetone, and 470 g of hexane were added into it. The lower layer of the separated solution in the lower layer was taken and concentrated under reduced pressure. Into the concentrated solution thus obtained was added 550 g of ethyl acetate, the layer of which was then washed successively by 15% aqueous acetic acid, 25% aqueous pyridine, and water, and then concentrated under reduced pressure. After 300 g of acetone was added to the concentrated solution, the resulted mixture was added drop-wise into 2 liters of water to crystallize the polymer out. The polymer thus crystallized was collected by filtration, and then dried under vacuum at 40° C. for 20 hours to obtain the polymer as the white powder solid shown by the following Polymer 12. The yield was 106 g (65%). Here, Mw is shown by the polystyrene-equivalent weight-average molecular weight measured by a GPC.

Polymer 12

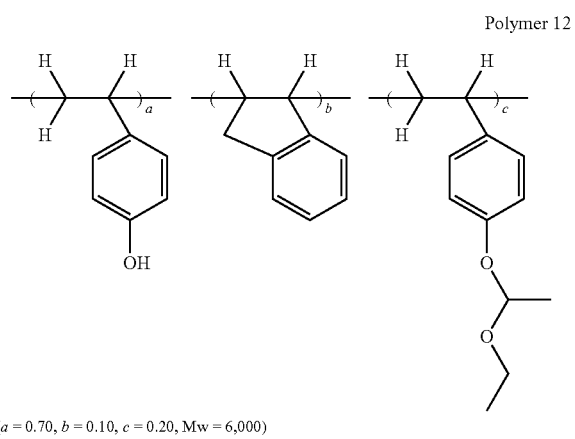

$(a = 0.70, b = 0.10, c = 0.20, \text{Mw} = 6,000)$

Synthesis Examples 2-13 to 2-22

Synthesis of Polymers 13 to 22

Polymers 13 to 22 were synthesized in a similar manner to that of Synthesis Example 2-12 except that each monomer and their blending ratios were changed (see Table 1).

Syhthesis Example 2-23

Synthesis of Polymer 23

Into 50 g of Polymer 21, the copolymer of hydroxystyrene: indene0.90:0.10 (mol ratio) obtained by the above-mentioned method, were added 500 g of tetrahydrofurane and 26 g of triethylamine. Into this mixture solution was added drop-wise 7.8 g of 1-chloro-1-methoxy-2-methylpropane, and then they were stirred at room temperature for 2 hours. After the stirring, 150 g of water was added to separate the organic layer, which was then concentrated under reduced pressure. Into the concentrated solution thus obtained was added 270 g of ethyl acetate, the layer of which was then successively washed by 15% aqueous acetic acid, 25% aqueous pyridine, and water, and then concentrated under reduced pressure. After 150 g of acetone was added to the concentrated solution, the resulted mixture was added drop-wise into 2 liters of water to crystallize the polymer out. The polymer thus crystallized was collected by filtration, and then dried under vacuum at 40° C. for 20 hours to obtain the polymer as the white powder solid shown by the following Polymer 23. The yield was 45 g (87%). Here, Mw is shown by the polystyrene-equivalent weight-average molecular weight measured by a GPC.

Polymer 23

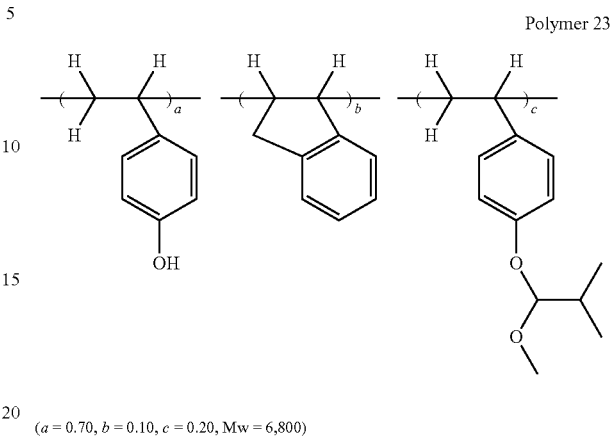

$(a = 0.70, b = 0.10, c = 0.20, \text{Mw} = 6,800)$

Synthesis Examples 2-24 to 2-26

Synthesis of Polymers 24 to 26

Polymers 24 to 26 were synthesized in a similar manner to that of Synthesis Example 2-23 except that each monomer and their blending ratios were changed (see Table 1).

Deprotection and protection of the polyhydroxy styrene derivatives in Synthesis Examples 2-12 to 2-26 are elaborated in Japanese Patent Application Laid-Open No. 2004-115630, Japanese Patent Application Laid-Open No. 2005-8766, and so on.

Synthesis Example 2-27

Synthesis of Polymer 27

Under a nitrogen atmosphere, 5.9 g of methacrylic acid=3-hydroxy-1-adamantyl, 7.5 g of methacrylic acid=adamantane-2-yloxymethyl, 10.1 g of methacrylic acid=4,8-dioxatricyclo[4.2.1.0$^{3,7}$]nonane-5-one-2-yl, and 0.9 g of 2,2'-azobis(isobutyric acid)dimethyl were dissolved in 54.2 g of methyl ethyl ketone. Thus prepared solution was added drop-wise into 27.1 g of methyl ethyl ketone over 4 hours with agitation under a nitrogen atmosphere at 80° C. After the drop-wise addition, the agitation was continued for 2 hours with keeping the temperature at 80° C. After cooled to room temperature, the polymer solution was added drop-wise into 250 g of hexane. The deposited solid was collected by filtration, washed by a solvent mixture of 27 g methyl ethyl ketone and 117 g of hexane for two times, and then dried under vacuum at 50° C. for 20 hours to obtain the polymer as the white powder solid shown by the following Polymer 27. The yield was 21.6 g (92%). Here, Mw is shown by the polystyrene-equivalent weight-average molecular weight measured by a GPC.

Polymer 27

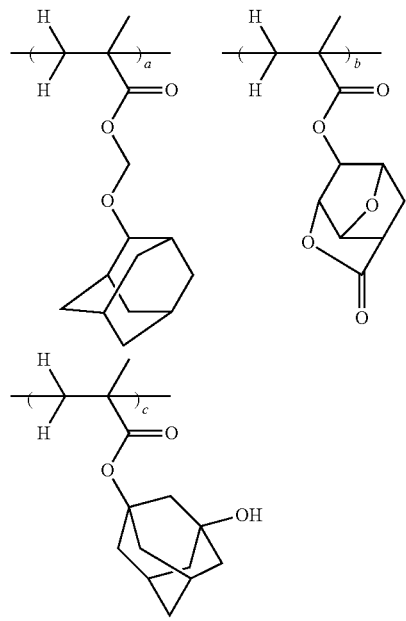

($a$ = 0.30, $b$ = .45, $c$ = 0.25, Mw =8,000)

Synthesis Examples 2-28 to 2-30

Synthesis of Polymers 28 to 30

Polymers 28 to 30 were synthesized in a similar manner to that of Synthesis Example 2-27 except that each monomer and their blending ratios were changed (see Table 1).

The synthesized resins are shown in the following Table 1. Here, the introduction ratio is shown by the mole ratio. The structures of each unit in Table 1 are shown in the following Table 2 and Table 3.

TABLE 1

|  | Resin | Unit 1 (introduction ratio) | Unit 2 (introduction ratio) | Unit 3 (introduction ratio) |
| --- | --- | --- | --- | --- |
| Synthesis Example 2-1 | Polymer 1 | A-2 (0.70) | A-9 (0.10) | A-3 (0.20) |
| Synthesis Example 2-2 | Polymer 2 | A-2 (0.70) | A-10 (0.10) | A-3 (0.20) |
| Synthesis Example 2-3 | Polymer 3 | A-2 (0.70) | A-9 (0.10) | A-4 (0.20) |
| Synthesis Example 2-4 | Polymer 4 | A-2 (0.70) | A-10 (0.10) | A-4 (0.20) |
| Synthesis Example 2-5 | Polymer 5 | A-2 (0.70) | A-9 (0.10) | A-5 (0.20) |
| Synthesis Example 2-6 | Polymer 6 | A-2 (0.70) | A-10 (0.10) | A-5 (0.20) |
| Synthesis Example 2-7 | Polymer 7 | A-2 (0.80) | A-9 (0.10) | A-8 (0.10) |
| Synthesis Example 2-8 | Polymer 8 | A-2 (0.85) | B-4M (0.15) | — |
| Synthesis Example 2-9 | Polymer 9 | A-2 (0.80) | A-10 (0.10) | B-4M (0.10) |
| Synthesis Example 2-10 | Polymer 10 | A-2 (0.90) | A-9 (0.10) | — |
| Synthesis Example 2-11 | Polymer 11 | A-2 (0.90) | A-10 (0.10) | — |
| Synthesis Example 2-12 | Polymer 12 | A-1 (0.70) | A-9 (0.10) | A-3 (0.20) |
| Synthesis Example 2-13 | Polymer 13 | A-1 (0.70) | A-10 (0.10) | A-3 (0.20) |
| Synthesis Example 2-14 | Polymer 14 | A-1 (0.70) | A-9 (0.10) | A-4 (0.20) |
| Synthesis Example 2-15 | Polymer 15 | A-1 (0.70) | A-10 (0.10) | A-4 (0.20) |
| Synthesis Example 2-16 | Polymer 16 | A-1 (0.70) | A-9 (0.10) | A-5 (0.20) |
| Synthesis Example 2-17 | Polymer 17 | A-1 (0.70) | A-10 (0.10) | A-5 (0.20) |
| Synthesis Example 2-18 | Polymer 18 | A-1 (0.80) | A-9 (0.10) | A-8 (0.10) |
| Synthesis Example 2-19 | Polymer 19 | A-1 (0.85) | B-4M (0.15) | — |
| Synthesis Example 2-20 | Polymer 20 | A-1 (0.80) | A-10 (0.10) | B-4M (0.10) |
| Synthesis Example 2-21 | Polymer 21 | A-1 (0.90) | A-9 (0.10) | — |
| Synthesis Example 2-22 | Polymer 22 | A-1 (0.90) | A-10 (0.10) | — |
| Synthesis Example 2-23 | Polymer 23 | A-1 (0.70) | A-9 (0.10) | A-6 (0.20) |
| Synthesis Example 2-24 | Polymer 24 | A-1 (0.70) | A-10 (0.10) | A-6 (0.20) |
| Synthesis Example 2-25 | Polymer 25 | A-1 (0.70) | A-9 (0.10) | A-7 (0.20) |
| Synthesis Example 2-26 | Polymer 26 | A-1 (0.70) | A-10 (0.10) | A-7 (0.20) |
| Synthesis Example 2-27 | Polymer 27 | B-8M (0.30) | B-4M (0.25) | B-5M (0.45) |
| Synthesis Example 2-28 | Polymer 28 | B-3M (0.50) | B-4M (0.20) | B-5M (0.30) |
| Synthesis Example 2-29 | Polymer 29 | B-1M (0.50) | B-4M (0.10) | B-5M (0.40) |
| Synthesis Example 2-30 | Polymer 30 | B-2M (0.50) | B-4M (0.10) | B-5M (0.40) |

TABLE 2

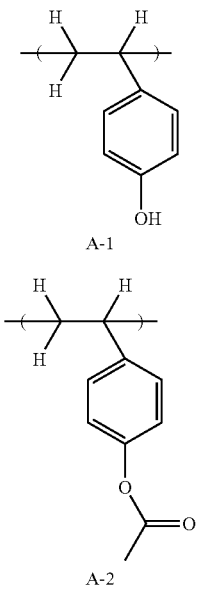

TABLE 2-continued
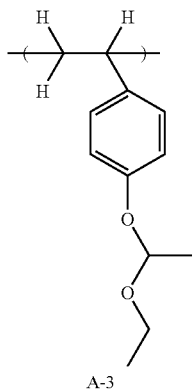
A-3
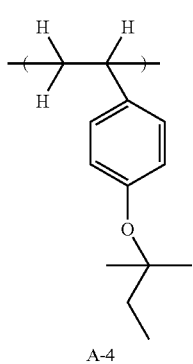
A-4
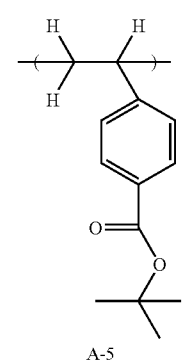
A-5
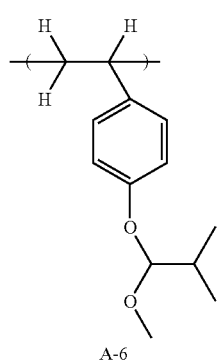
A-6
TABLE 2-continued
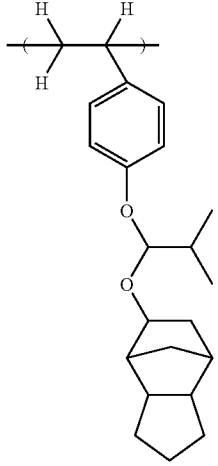
A-7
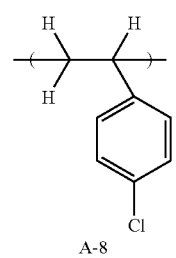
A-8
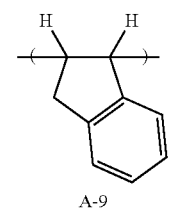
A-9
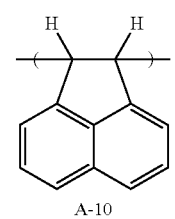
A-10
TABLE 3
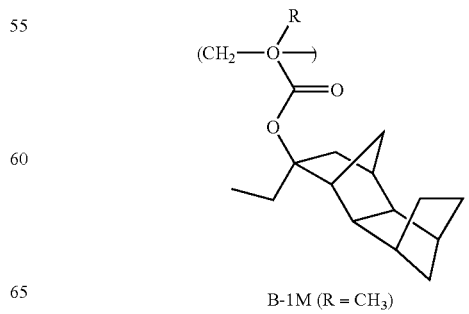
B-1M (R = CH$_3$)

TABLE 3-continued

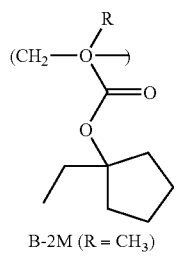

B-2M (R = CH₃)

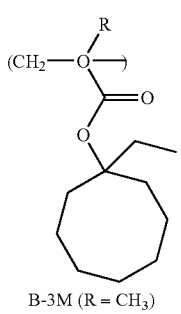

B-3M (R = CH₃)

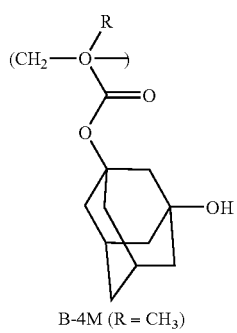

B-4M (R = CH₃)

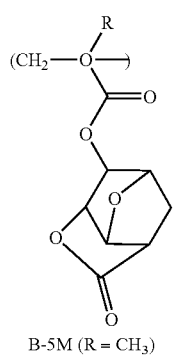

B-5M (R = CH₃)

TABLE 3-continued

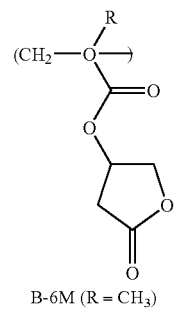

B-6M (R = CH₃)

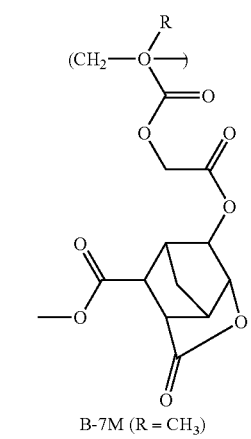

B-7M (R = CH₃)

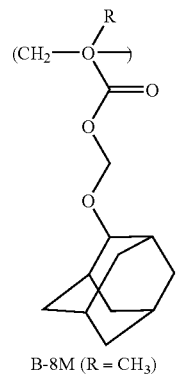

B-8M (R = CH₃)

Preparation of Resist Compositions

Examples 1-1 to 1-19 and Comparative Examples 1-1 to 1-6

Each of the resins used as the base resin and prepared as described above (Polymers 12 to 20 and 23 to 30 for Examples, and Polymers 20, 25, 27, and 29 for Comparative Examples), an acid generator, an additive (a base or a crosslinker), and a solvent were added according to the composition shown in the following Table 4. After they were mixed and dissolved, the resulted solution was filtrated by a filter (pore diameter of 0.2 μm) made of Teflon (registered trade mark) to obtain each resist composition (R-01 to R-19 for Examples, and R-20 to R-25 for Comparative Examples). Here, the solvent containing 0.01% by mass of the surfactant (surfactant-1) manufactured by Omnova Inc., which will be mentioned later, was used in all of the compositions.

TABLE 4

| | Resist | Resin (parts by weight) | | Acid Generator (parts by weight) | | Additive (parts by weight) | | Solvent 1 (parts by weight) | | Solvent 2 (parts by weight) | |
|---|---|---|---|---|---|---|---|---|---|---|---|
| Example 1-1 | R-01 | Polymer 12 | (80) | PAG-2 | (9.9) | Base-1 | (1.10) | PGMEA | (540) | EL | (1280) |
| Example 1-2 | R-02 | Polymer 12 | (80) | PAG-3 | (8.8) | Base-1 | (1.10) | PGMEA | (540) | EL | (1280) |
| Example 1-3 | R-03 | Polymer 12 | (80) | PAG-4 | (10.1) | Base-1 | (1.10) | PGMEA | (540) | EL | (1280) |
| Example 1-4 | R-04 | Polymer 13 | (80) | PAG-4 | (10.1) | Base-1 | (1.10) | PGMEA | (540) | EL | (1280) |
| Example 1-5 | R-05 | Polymer 14 | (80) | PAG-4 | (10.1) | Base-1 | (1.10) | PGMEA | (540) | EL | (1280) |
| Example 1-6 | R-06 | Polymer 15 | (80) | PAG-4 | (10.1) | Base-1 | (1.10) | PGMEA | (540) | EL | (1280) |
| Example 1-7 | R-07 | Polymer 16 | (80) | PAG-4 | (10.1) | Base-1 | (1.10) | PGMEA | (540) | EL | (1280) |
| Example 1-8 | R-08 | Polymer 17 | (80) | PAG-4 | (10.1) | Base-1 | (1.10) | PGMEA | (540) | EL | (1280) |
| Example 1-9 | R-09 | Polymer 18 | (80) | PAG-4 | (10.1) | Base-1 TMGU | (1.10) (10) | PGMEA | (540) | EL | (1280) |
| Example 1-10 | R-10 | Polymer 19 | (80) | PAG-4 | (10.1) | Base-1 | (1.10) | PGMEA | (540) | EL | (1280) |
| Example 1-11 | R-11 | Polymer 20 | (80) | PAG-4 | (10.1) | Base-1 | (1.10) | PGMEA | (540) | EL | (1280) |
| Example 1-12 | R-12 | Polymer 23 | (80) | PAG-4 | (10.1) | Base-1 | (1.10) | PGMEA | (540) | EL | (1280) |
| Example 1-13 | R-13 | Polymer 24 | (80) | PAG-4 | (10.1) | Base-1 | (1.10) | PGMEA | (540) | EL | (1280) |
| Example 1-14 | R-14 | Polymer 25 | (80) | PAG-4 | (10.1) | Base-1 | (1.10) | PGMEA | (540) | EL | (1280) |
| Example 1-15 | R-15 | Polymer 26 | (80) | PAG-4 | (10.1) | Base-1 | (1.10) | PGMEA | (540) | EL | (1280) |
| Example 1-16 | R-16 | Polymer 27 | (80) | PAG-2 | (7.0) | Base-2 | (1.23) | PGMEA | (896) | CyHO | (364) |
| Example 1-17 | R-17 | Polymer 28 | (80) | PAG-2 | (7.0) | Base-2 | (1.23) | PGMEA | (896) | CyHO | (364) |
| Example 1-18 | R-18 | Polymer 29 | (80) | PAG-2 PAG-III | (5.3) (7.6) | — | — | PGMEA | (896) | CyHO | (364) |
| Example 1-19 | R-19 | Polymer 30 | (80) | PAG-2 PAG-III | (5.3) (7.6) | — | — | PGMEA | (896) | CyHO | (364) |
| Comparative Example 1-1 | R-20 | Polymer 20 | (80) | PAG-I | (7.2) | Base-1 | (1.10) | PGMEA | (540) | EL | (1280) |
| Comparative Example 1-2 | R-21 | Polymer 20 | (80) | PAG-II | (7.9) | Base-1 | (1.10) | PGMEA | (540) | EL | (1280) |
| Comparative Example 1-3 | R-22 | Polymer 25 | (80) | PAG-I | (7.2) | Base-1 | (1.10) | PGMEA | (540) | EL | (1280) |
| Comparative Example 1-4 | R-23 | Polymer 25 | (80) | PAG-II | (7.9) | Base-1 | (1.10) | PGMEA | (540) | EL | (1280) |
| Comparative Example 1-5 | R-24 | Polymer 27 | (80) | PAG-III | (6.0) | Base-2 | (1.23) | PGMEA | (896) | CyHO | (364) |
| Comparative Example 1-6 | R-25 | Polymer 29 | (80) | PAG-III | (6.0) | Base-2 | (1.23) | PGMEA | (896) | CyHO | (364) |

In Table 4, acid generators, additives (a base or bridging agent), and solvents shown in a cable address represent as follows respectively.
PAG-2 to 4: acid generators obtained in the Synthesis Example.
PAG-I: triphenylsulfonium camphorsulfonate
PAG-II: triphenylsulfonium 2,4,6-triisopropylbenzenesulfonate
PAG-III: triphenylsulfonium 2-(adamantane-1-carbonyloxy)-1,1,3,3,3-pentafuluoropropane-1-sulfonate (a compound described in a Japanese Patent Laid-Open No. 2007-145797)
Base-1: Tri(2-methoxymethoxyethyl)amine
Base-2: lauric acid 2-morpholinoethyl
TMGU: 1,3,4,6-tetramethoxymethyl glycoluril
PGMEA: Propylene glycol monomethyl ether acetate
CyHO: cyclohexanone
EL: ethyl lactate
surface active agent-1: 3-methyl-3-(2,2,2-trifluoroethoxymethyl)oxwtabne.tetrahydrofuran.2,2-dimethyl-1,3-propanedioar copolymer (manufactured by Omnova Inc.)
Evaluation of Resolution, Depth of focus, and Pattern Form: KrF Exposure Examples 2-1 to 2-14 and Comparative Examples 2-1 to 2-4

Each resist composition of the present invention (R-01 to R-08 and R-10 to R-15) and of Comparative Examples (R-20 to R-23) was applied by spin coating to give the thickness of 0.33 μm on a 8-inch silicon wafer laminated with a 0.02-μm silicon oxide. Coating and the below-mentioned baking, and development procedures were made with a Coater Developer Clean Track Act 8 (manufactured by Tokyo Electron Ltd.).

Subsequently, this silicon wafer was baked on a hot plate at 110° C. for 90 seconds, exposed (normal illumination) by using an excimer laser scanner (NSR-S203B NA=0.68, manufactured by Nikon Corp.), baked at 110° C. for 90 seconds (PEB: post exposure bake), and then developed by an aqueous tetramethyl ammonium hydroxide solution (2.38% by mass) to obtain a positive pattern (Examples 2-1 to 2-14, and Comparative Examples 2-1 to 2-4).

The exposure dose to resolve the top and the bottom of the line-and-space with 0.18 μm at 1:1 was taken as the optimum exposure dose (sensitivity: Eop), and the minimum line width of the line-and-space separated at this exposure dose was taken as the resolution of the resist for evaluation. The resolved resist pattern form was observed on the resist's cross section view by using a scanning electron microscope. Line width of the isolated line of the 1:10 line-and-space with the same exposure dose was measured, and the value obtained by subtracting the line width of the isolated line from the line width of the group line was taken as the dimensional difference (I/G bias) between the isolated pattern and the dense pattern. Further, when the resist pattern form keeps its rectangular shape with the displaced focus while at the same time the resist pattern keeps 80% of its film thickness (relative to the case of the matched focus), it was judged as valid and the depth of focus was measured. The results of the foregoing are shown in the following Table 5.

TABLE 5

|  | Resist | Eop (mJ/cm²) | Resolution (μm) | DOF with 0.18 μm (μm) | I/G bias (nm) | Pattern Profile |
|---|---|---|---|---|---|---|
| Example 2-1 | R-1 | 33 | 0.17 | 0.6 | 28 | rectangle |
| Example 2-2 | R-2 | 30 | 0.17 | 0.6 | 45 | rectangle |
| Example 2-3 | R-3 | 32 | 0.17 | 0.6 | 33 | rectangle |
| Example 2-4 | R-4 | 32 | 0.17 | 0.7 | 32 | rectangle |
| Example 2-5 | R-5 | 31 | 0.17 | 0.7 | 33 | rectangle |
| Example 2-6 | R-6 | 33 | 0.16 | 0.6 | 30 | rectangle |
| Example 2-7 | R-7 | 33 | 0.17 | 0.6 | 34 | rectangle |
| Example 2-8 | R-8 | 32 | 0.17 | 0.7 | 29 | rectangle |
| Example 2-9 | R-10 | 34 | 0.17 | 0.6 | 32 | rectangle |
| Example 2-10 | R-11 | 32 | 0.17 | 0.6 | 30 | rectangle |
| Example 2-11 | R-12 | 31 | 0.16 | 0.7 | 32 | rectangle |
| Example 2-12 | R-13 | 31 | 0.17 | 0.7 | 36 | rectangle |
| Example 2-13 | R-14 | 30 | 0.16 | 0.7 | 35 | rectangle |
| Example 2-14 | R-15 | 31 | 0.16 | 0.7 | 29 | rectangle |
| Comparative Example 2-1 | R-20 | 35 | 0.18 | 0.4 | 42 | rather rounding profile |
| Comparative Example 2-2 | R-21 | 34 | 0.18 | 0.5 | 46 | rather rounding profile |
| Comparative Example 2-3 | R-22 | 36 | 0.18 | 0.4 | 44 | rather rounding profile |
| Comparative Example 2-4 | R-23 | 35 | 0.18 | 0.5 | 43 | rather rounding profile |

From the results of Examples in Table 5, it was confirmed that, in the KrF excimer exposure, the resist composition added with the acid generator of the present invention is excellent in the resolution performance, and at the same time, excellent in the depth of focus, small in the I/G bias, and good in the pattern form as well.

Evaluation of Resolution: EB Exposure

Examples 3-1 to 3-14, and Comparative Examples 3-1 to 3-4

Each resist composition of the present invention (R-01 to R-08 and R-10 to R-15) and of Comparative Examples (R-20 to R-23) was applied by spin coating to give the thickness of 0.15 μm on a silicon wafer whose surface was laminated with Cr as the photomask blanks model.

Subsequently, this silicon wafer was baked on a hot plate at 110° C. for 4 minutes, exposed by using an electron beam exposure instrument (HL-800D, acceleration voltage of 50 KeV, manufactured by Hitachi High-Technologies Corp.), baked at 110° C. for 4 minutes (PEB: post exposure bake), and developed by an aqueous tetramethyl ammonium hydroxide solution (2.38% by mass) to obtain a positive pattern.

The resist patterns obtained were evaluated as follows. The exposure dose to resolve the top and the bottom of the line-and-space with 0.20 μm at 1:1 was taken as the optimum exposure dose (sensitivity: Eop), and the minimum line width of the line-and-space separated at this exposure dose was taken as the resolution of the resist for evaluation. The resolved resist pattern form was observed on the resist's cross section view by using a scanning electron microscope. The PED (Post Exposure Delay) in vacuum was evaluated as follows; after exposed by an electron beam exposure instrument, the resist was allowed to stand in an instrument under vacuum for 24 hours, and thereafter PEB and development were carried out. The line width of the obtained line-and-space with 0.20 μm at Eop was compared with the line width obtained at the time of baking immediately after exposure, and the difference (nm) between them was shown.

TABLE 6

|  | Resist | Eop (μC/cm²) | Resolution (nm) | PED under vacuum (nm) | Pattern Profile |
|---|---|---|---|---|---|
| Example 3-1 | R-1 | 9.1 | 75 | 5.1 | rectangle |
| Example 3-2 | R-2 | 9.5 | 85 | 6.4 | rectangle |
| Example 3-3 | R-3 | 8.8 | 80 | 5.0 | rectangle |
| Example 3-4 | R-4 | 8.7 | 80 | 5.1 | rectangle |
| Example 3-5 | R-5 | 8.4 | 80 | 5.4 | rectangle |
| Example 3-6 | R-6 | 9.3 | 75 | 5.3 | rectangle |
| Example 3-7 | R-7 | 8.6 | 75 | 5.8 | rectangle |
| Example 3-8 | R-8 | 8.8 | 80 | 5.1 | rectangle |
| Example 3-9 | R-10 | 9.0 | 80 | 5.5 | rectangle |
| Example 3-10 | R-11 | 9.1 | 80 | 5.3 | rectangle |
| Example 3-11 | R-12 | 8.3 | 75 | 6.1 | rectangle |
| Example 3-12 | R-13 | 7.9 | 75 | 5.8 | rectangle |
| Example 3-13 | R-14 | 8.2 | 70 | 6.0 | rectangle |
| Example 3-14 | R-15 | 7.7 | 70 | 6.2 | rectangle |
| Comparative Example 3-1 | R-20 | 10.7 | 110 | 7.2 | rather rounding profile |
| Comparative Example 3-2 | R-21 | 10.2 | 100 | 7.0 | rather rounding profile |
| Comparative Example 3-3 | R-22 | 9.6 | 100 | 7.8 | rather rounding profile |
| Comparative Example 3-4 | R-23 | 9.7 | 95 | 6.8 | rather rounding profile |

From the results in Table 6, it was confirmed that, in the EB exposure, in the resist composition of the present invention, the resolution performance is excellent even though on the Cr film, the change in line width and the deterioration of the form are small even with a prolonged PED, the pattern form is also excellent, and thus the resist composition of the present invention can be applied advantageously to the mask blanks formed of a chromium compound film.

Evaluation of Resolution, Exposure Margin, and Line Width Roughness (LWR): ArF Exposure Examples 4-1 to 4-4, and Comparative Examples 4-1 to 4-2

A solution for an anti-reflection film (ARC-29A, manufactured by Nissan Chemical Industries, Ltd.) was applied on a silicon substrate and baked at 200° C. for 60 seconds to obtain an anti-reflection film (film thickness of 78 nm). On it, each resist composition of the present invention (R-16 to R-19) and of Comparative Examples (R-24 and R-25) was applied by spin coating and baked on a hot plate at 100° C. for 60 seconds to obtain a resist film with the film thickness of 100 nm. This was exposed by using an ArF excimer laser scanner (NSR-S307E, NA=0.85, 4/5 annular illumination, and 6% half tone phase shift mask, manufactured by Nikon, Corp.), baked at 100° C. for 60 seconds (PEB: post exposure bake), and then developed by an aqueous tetramethyl ammonium hydroxide solution (2.38% by mass) for 60 seconds.

The resists were evaluated as follows; the exposure dose to resolve the line-and-space with the 80 nm group at 1:1 was taken as the optimum exposure dose (Eop, mJ/cm$^2$), and the minimum line width (nm) of the line-and-space separated at this exposure dose was taken as the resolution of the resist for evaluation. The exposure margin was evaluated as follows; the exposure dose range to allow the pattern size change within 80 nm±10% with the change of the optimum exposure dose was obtained, and this value was divided by the optimum exposure dose and then expressed by the percentage. The performance change is smaller and the exposure margin is better with larger the percentage value. The line width roughness (LWR) of the line-and-space with 80 nm was measured by the length measuring SEM (S-9380, manufactured by Hitachi High-Technologies Corp.). The results are shown in the following Table 7.

TABLE 7

| | Resist | Optimum exposure dose (mJ/cm$^2$) | Limit to resolution (nm) | Exposure margin (%) | LWR (nm) |
|---|---|---|---|---|---|
| Example 4-1 | R-16 | 38 | 80 | 13.8 | 5.9 |
| Example 4-2 | R-17 | 38 | 80 | 13.9 | 5.8 |
| Example 4-3 | R-18 | 30 | 75 | 14.3 | 5.2 |
| Example 4-4 | R-19 | 29 | 80 | 14.5 | 5.1 |
| Comparative Example 4-1 | R-24 | 40 | 80 | 12.9 | 7.3 |
| Comparative Example 4-2 | R-25 | 37 | 80 | 12.7 | 7.5 |

From the results of Examples in Table 7, it was confirmed that, in the resist composition of the present invention, in the ArF excimer exposure too, the resolution performance is excellent, and at the same time the exposure margin is excellent, and the value of the line width roughness is small.

What is claimed is:

1. A sulfonate represented by the following general formula (1):

$$HO-C(CF_3)_2-CH_2SO_3^- M^+ \tag{1}$$

wherein, M$^+$ represents a cation.

2. The sulfonate according to claim 1, wherein the M$^+$ is any of a lithium ion, a sodium ion, a potassium ion, an ammonium ion, an iodonium ion, and a sulfonium ion.

3. A method for manufacturing the sulfonate according to claim 1 by reacting 2,2-bistrifluoromethyloxylane with a sulfur compound in water.

4. A sulfonate represented by the following general formula (2):

$$R^1-COOC(CF_3)_2-CH_2SO_3^- M^+ \tag{2}$$

wherein, R$^1$ represents a linear, a branched, or a cyclic monovalent hydrocarbon group having 1 to 50 carbon atoms optionally containing a hetero atom; and M$^+$ represents a cation.

5. The sulfonate according to claim 4, wherein the M$^+$ is any of a lithium ion, a sodium ion, a potassium ion, an ammonium ion, an iodonium ion, and a sulfonium ion.

6. The sulfonate according to claim 4, wherein the sulfonate is a sulfonium salt of sulfonic acid represented by the following general formula (3):

$$R^1-COOC(CF_3)_2-CH_2SO_3^- R^2R^3R^4S^+ \tag{3}$$

wherein, R$^1$ represents the same as before; each R$^2$, R$^3$, and R$^4$ independently represents a linear or a branched alkyl, alkenyl, or oxoalkyl group, substituted or unsubstituted, having 1 to 10 carbon atoms, a substituted or an unsubstituted aryl, aralkyl, or aryl oxoalkyl group having 6 to 18 carbon atoms, or any two or more of R$^2$, R$^3$, and R$^4$ may be bonded with each other to form a ring together with a sulfur atom in the formula.

7. The sulfonate according to claim 6, wherein the sulfonium salt of sulfonic acid is the one represented by the following general formula (4):

$$R^1-COOC(CF_3)_2-CH_2SO_3^-(R^5(O)_n)_m Ph'S^+Ph_2 \tag{4}$$

wherein, R$^1$ represents the same as before; R$^5$ represents a linear, a branched, or a cyclic alkyl or alkenyl group, substituted or unsubstituted, having 1 to 20 carbon atoms, or a substituted or an unsubstituted aryl group having 6 to 14 carbon atoms; "m" represents an integer of 1 to 5; "n" represents 0 or 1; Ph represents a phenyl group; Ph' represents a phenyl group whose "m" hydrogen atoms are substituted by a R$^5$(O)$_n$— group.

8. The sulfonate according to claim 4, wherein the sulfonate is an iodonium salt of sulfonic acid represented by the following general formula (5):

$$R^1-COOC(CF_3)_2-CH_2SO_3^-((R^5(O)_n)_m Ph')_2 I^+ \tag{5}$$

wherein, R$^1$ represents the same as before; R$^5$ represents a linear, a branched, or a cyclic alkyl or alkenyl group, substituted or unsubstituted, having 1 to 20 carbon atoms, or a substituted or an unsubstituted aryl group having 6 to 14 carbon atoms; "m" represents an integer of 1 to 5; "n" represents 0 or 1; Ph' represents a phenyl group whose "m" hydrogen atoms are substituted by a R$^5$(O)$_n$— group.

9. A photosensitive acid generator for use in a chemically amplified resist composition generating, by responding to a high energy beam, a sulfonic acid represented by the following general formula (6):

$$R^1-COOC(CF_3)_2-CH_2SO_3^- H^+ \tag{6}$$

wherein, R$^1$ represents a linear, a branched, or a cyclic monovalent hydrocarbon group having 1 to 50 carbon atoms optionally containing a hetero atom.

10. The photosensitive acid generator according to claim 9, wherein the photosensitive acid generator comprises any one of the sulfonates represented by the following general formulae (3) to (5), $$R^1-COOC(CF_3)_2-CH_2SO_3^- R^2R^3R^4S^+ \tag{3}$$

$$R^1-COOC(CF_3)_2-CH_2SO_3^-(R^5(O)_n)_m Ph'S^+Ph_2 \tag{4}$$

$$R^1-COOC(CF_3)_2-CH_2SO_3^-((R^5(O)_n)_m Ph')_2 I^+ \tag{5}$$

wherein, R$^1$ represents the same as before;
each R$^2$, R$^3$, and R$^4$ independently represents a linear or a branched alkyl, alkenyl, or oxoalkyl group, substituted or unsubstituted, having 1 to 10 carbon atoms, a substituted or an unsubstituted aryl, aralkyl, or aryl oxoalkyl group having 6 to 18 carbon atoms, or any two or more of $R^2$, $R^3$, and $R^4$ may be bonded with each other to form a ring together with a sulfur atom in the formula;

$R^5$ represents a linear, a branched, or a cyclic alkyl or alkenyl group, substituted or unsubstituted, having 1 to 20 carbon atoms, or a substituted or an unsubstituted aryl group having 6 to 14 carbon atoms;

"m" represents an integer of 1 to 5;

"n" represents 0 or 1;

Ph represents a phenyl group; and

Ph' represents a phenyl group whose "m" hydrogen atoms are substituted by a $R^5(O)_n$—group.

11. A resist composition comprising a base resin, an acid generator, and an organic solvent, wherein the acid generator is the photosensitive acid generator according to claim 9.

12. A resist composition comprising a base resin, an acid generator, and an organic solvent, wherein the acid generator is the photosensitive acid generator according to claim 10.

13. The resist composition according to claim 11, wherein the resist composition is a chemically amplified positive resist composition, wherein the base resin contained in the resist composition is not soluble or sparingly soluble in a developer but soluble in the developer by an acid.

14. The resist composition according to claim 12, wherein the resist composition is a chemically amplified positive resist composition, wherein the base resin contained in the resist composition is not soluble or sparingly soluble in a developer but soluble in the developer by an acid.

15. The resist composition according to claim 11, wherein the resist composition contains further a basic compound.

16. The resist composition according to claim 14, wherein the resist composition contains further a basic compound.

17. A patterning process comprising at least a step of coating the resist composition according to claim 11 onto a substrate; a step of pattern-exposing by using a high energy beam via a photomask after a heat-treatment; and, after the heat-treatment as appropriate, a step of developing by using a developer.

18. A patterning process comprising at least a step of coating the resist composition according to claim 16 onto a substrate; a step of pattern-exposing by using a high energy beam via a photomask after a heat-treatment; and, after the heat-treatment as appropriate, a step of developing by using a developer.

19. A photomask blank, wherein the resist composition according to claim 11 is formed on a chrome compound layer.

20. A photomask blank, wherein the resist composition according to claim 16 is formed on a chrome compound layer.

* * * * *